US006300487B1

(12) United States Patent
Leung et al.

(10) Patent No.: US 6,300,487 B1
(45) Date of Patent: Oct. 9, 2001

(54) MAMMALIAN LYSOPHATIDIC ACID ACYLTRANSFERASE

(75) Inventors: David W. Leung, Mercer Island; Daniel Adourel, Woodinville; David Hollenback, Seattle, all of WA (US)

(73) Assignee: Cell Therapuetics, Inc., Seattle, WA (US)

( * ) Notice: Subject to any disclaimer, the term of this patent is extended or adjusted under 35 U.S.C. 154(b) by 0 days.

(21) Appl. No.: 09/215,252

(22) Filed: Dec. 18, 1998

Related U.S. Application Data

(63) Continuation-in-part of application No. 08/618,651, filed on Mar. 19, 1996, now abandoned.

(51) Int. Cl.$^7$ .......................... C07H 21/04; C07H 21/02; C12N 9/10
(52) U.S. Cl. ........................ 536/23.2; 536/23.1; 435/193
(58) Field of Search ................................. 536/23.2, 23.1; 435/193

(56) References Cited

U.S. PATENT DOCUMENTS 5,888,793 * 3/1999 Hillman et al. ...................... 435/193
6,001,620 * 12/1999 Hillman et al. ...................... 435/193

OTHER PUBLICATIONS

Sigma Catalog (1993) Catalog No. A3147. p. 48, Jan., 1994.*

Aguado et al.; "Characterization of a Human Lysophosphatidic Acid Acyltransferase That Is Encoded by a Gene Located in the Class III Region of the Human Major Histocompatibility Complex"; J. Biol. Chem; vol. 273, No. 7; Feb. 13, 1998; pp. 4096–4105.

West et al.; "Cloning and Expression of Two Human Lysophosphatidic Acid Acyltransferase cDNAs That Enhance Cytokine–Induced Signaling Responses in Cells"; Biology; vol. 16, No. 6; Jun. 1997; pp. 691–701.

Eberhardt et al.; "Human Lysophosphatidic Acid Acyltransferase"; J. Biol. Chem; vol. 272, No. 32; Aug. 8, 1997; pp. 20299–20305.

Sigma Catalog 1995, Sigma Chemical Company, St. Louis, Missouri, pp. 320, 322, 323 and 327.

Brown et al., Plant Molecular Biology, vol. 26: 211–223 (1994), "Isolation and characterization of a maize cDNA that complements a 1–acyl sn–glyerol–3 phosphate acyltransferase mutant of *Escherichia coli* and encodes a protein which has similarities to other acyltransferases".

Brown et al., Plant Molecular Biology, vol. 29:267–278(1995), "Identification of a cDNA that encodes a 1–acyl–sn–glycerol–3–phosphate acyltransferase from *Limnathes douglasii*".

Coleman et al., Mol Gen Genet, vol. 232: 295–303 (1992), "Characterization of the *Escherichia coli* gene for 1–acyl–sn–glycerol–3–phosphate acyltransferase (plsC)".

Hanke et al., Eur. J. Biochem, vol. 232: 806–810(1995), A plant acyltransferase involved in triacylglycerol biosynthesis compliments an *Escherichia coli* sn–1–acylglycerol–3–phosphate acyltransferase mutant.

Knutzon et al., Plant Physiol, vol. 109:999–1006(1995), "Cloning of a Coconut Endosperm cDNA Encoding a 1–Acyl–sn–Glycerol–3–Phosphate Acyltransferase that accepts Medium–Chain–Length Substrates".

Lassner et al., Plant Physiol., vol. 109: 1389–1394(1995), "Lysophosphatidic Acid Acyltransferase from Meadowfoam Mediates Insertion of Euric Acid at the sn–2 Position of Triacylglcerol in transgenic Rapeseed Oil".

Nagiec et al., *The Journal of Biological Chemistry*, vol. 268(29): 22156–22163(1993), "A Suppressor Gene that enables *Saccharomyces cerevisiae* to grow without making sphingolipids Encodes a Protein That Resembles an *Escherichia coli* Fatty Acyltransferase".

West et al., *DNA and Cell Biology*, "Cloning and Expression of Two Human Lysophosphatidic Acid Acyltransferase cDNAs that Enhance Cytokine–Induce Signaling Responses in Cells"., vol. 16:6 691–701, 1997.

Swartley et al., *Molecular Microbiology*, vol. 188(3): 401–412(1995), "Membrane glycerphospholipid biosynthesis in Neisseria meningitidis and Neisseria gonorrhoea: identification, characterization and mutagenesis of a lysophosphatidic acid acyltransferase".

* cited by examiner

*Primary Examiner*—Rebecca E. Prouty
*Assistant Examiner*—David J Steadman
(74) *Attorney, Agent, or Firm*—Foley & Lardner

(57) ABSTRACT

Polypeptides are obtained, for example, via expression of encoding cDNA sequences, that have the activity of the enzyme lysophosphatidic acid acyltransferase (LPAAT), also known as 1-acyl sn-glycerol-3-phosphate acyltransferase.

10 Claims, 33 Drawing Sheets

FIG. 1A

```
  1  GGAAGTCAGCAGGCGTTGGGGTGGCGGGAATAGCGGGGCAGC
 51  AGCCCCAGCCCTCAGAGACAGCAGAAAGGAGGAGGGGTGCTGG
101  GGGGACAGCCCCCCACCATTCCTACCCGCTATGGGCCAACTCCCCACTCC
151  CACCTCCCCCTCCCCATCGGCCGGGCTAGGACACCCCAAATCCCGTCGCCC
201  CCTTGGCACCACCCGACAGAGACAGAGACACAGCCATCCGCCACCA
251  CCGCTGCCGCCAGCCTGGGGAGCCCAGCCCCCCAGCCCCCCTAC
301  CCCTCTGAGGTGGCCAGA ATG GAT TTG TGG CCA GGG GCA TGG
                       Met Asp Leu Trp Pro Gly Ala Trp
343  ATG CTG CTG CTG CTC TTC CTG CTG CTC TTC C
     Met Leu Leu Leu Leu Phe Leu Leu Leu Phe L
                         10                       20
380  TG CTG CCC ACC CTG TGG TTC TGC AGC CCC AGT GCC AAG
     eu Leu Pro Thr Leu Trp Phe Cys Ser Pro Ser Ala Lys
                                           30
```

FIG. 1B

```
418  TAC TTC TTC AAG ATG GCC TTC TAC AAT GGC TGG ATC C
     Tyr Phe Phe Lys Met Ala Phe Tyr Asn Gly Trp Ile L
                                40

455  TC TTC CTG GCT GTG CTC GCC ATC CCT GTG TGT GCC GTG
     eu Phe Leu Ala Val Leu Ala Ile Pro Val Cys Ala Val
                              50

493  CGA GGA CGC AAC GTC GAG AAC ATG AAG ATC TTG CGT C
     Arg Gly Arg Asn Val Glu Asn Met Lys Ile Leu Arg L
                         60              70

530  TA ATG CTG CTC CAC ATC AAA TAC CTG TAC GGG ATC CGA
     eu Met Leu Leu His Ile Lys Tyr Leu Tyr Gly Ile Arg
                                          80
```

FIG. 1C

```
568  GTG GAG GTG CGA GGG GCT CAC CAC TTC CCT CCC TCG C
     Val Glu Val Arg Gly Ala His His Phe Pro Pro Ser G
                          90

605  AG CCC TAT GTT GTT GTC TCC AAC CAC CAG AGC TCT CTC
     ln Pro Tyr Val Val Val Ser Asn His Gln Ser Ser Leu
                         100

643  GAT CTG CTT GGG ATG ATG GAG GTA CTG CCA GGC CGC T
     Asp Leu Leu Gly Met Met Glu Val Leu Pro Gly Arg C
              110                           120

680  GT GTG CCC ATT GCC AAG CGC GAG CTA CTG TGG GCT GGC
     ys Val Pro Ile Ala Lys Arg Glu Leu Leu Trp Ala Gly
                                              130
```

FIG. 1D

```
718  TCT GCC GGG CTG GCC TGC TGG CTG GCA GGA GTC ATC T
     Ser Ala Gly Leu Ala Cys Trp Leu Ala Gly Val Ile P
                                     140

755  TC ATC GAC CGG AAG CGC ACG GGG GAT GCC ATC AGT GTC
     he Ile Asp Arg Lys Arg Thr Gly Asp Ala Ile Ser Val
                              150

793  ATG TCT GAG GTC GCC CAG ACC CTG CTC ACC CAG GAC G
     Met Ser Glu Val Ala Gln Thr Leu Leu Thr Gln Asp V
                     160

830  TG AGG GTC TGG GTG TTT CCT GAG GGA ACG AGA AAC CAC
     al Arg Val Trp Val Phe Pro Glu Gly Thr Arg Asn His
                                              170
                                                      180
```

FIG. 1E

```
868  AAT GGC TCC ATG CTG CCC TTC AAA CGT GGC GCC TTC C
     Asn Gly Ser Met Leu Pro Phe Lys Arg Gly Ala Phe H
                              190

905  AT CTT GCA GTG CAG GCC CAG GTT CCC ATT GTC CCC ATA
     is Leu Ala Val Gln Ala Gln Val Pro Ile Val Pro Ile
                              200

943  GTC ATG TCC TCC TAC CAA GAC TTC TAC TGC AAG AAG G
     Val Met Ser Ser Tyr Gln Asp Phe Tyr Cys Lys Lys G
                  210                          220

980  AG CGT CGC TTC ACC TCG GGA CAA TGT CAG GTG CGG GTG
     lu Arg Arg Phe Thr Ser Gly Gln Cys Gln Val Arg Val
                              230
```

FIG. 1F

```
1018  CTG CCC CCA GTG CCC ACG GAA GGG CTG ACA CCA GAT G
      Leu Pro Pro Val Pro Thr Glu Gly Leu Thr Pro Asp A
                              240

1055  AC GTC CCA GCT CTG GCT GAC AGA GTC CGG CAC TCC ATG
      sp Val Pro Ala Leu Ala Asp Arg Val Arg His Ser Met
                              250

1093  CTC ACT GTT TTC CGG GAA ATC TCC ACT GAT GGC CGG G
      Leu Thr Val Phe Arg Glu Ile Ser Thr Asp Gly Arg G
                              260

1130  GT GGT GGT GAC TAT CTG AAG AAG CCT GGG GGC GGT GGG
      ly Gly Gly Asp Tyr Leu Lys Lys Pro Gly Gly Gly 280
                                              270

1168  TGA ACCCTGGCTCTGAGCTCTCCTCCCATCTGTCCCTCTTCCTCCC

1216  CACACCTTACCCACCCAGTGGCCCTGAAGCAGGGCCAAACCCTCTTCCTT

1266  GTCTCCCCCTCCCCCACTTATTCTCCTCTTTGGAATCTTCAACTTCTGAA
```

FIG. 1G

```
1316  GTGAATGTGGATACAGCGCCACTCCTGCCCCTCTTGGCCCCATCCATGG
1366  ACTCTTGCCTCGGTGCAGTTTCCACTCTTGACCCCACCTCCTACTGTCT
1416  TGTCTGTGGGACAGTTGCCTCCCCCCAGTGACTCTCCAGCCTACAC
1466  AAGGGAGGGAACATTCCATCCCCAGTGGAGTCTCTTCCTATGTGGTCTT
1516  CTCTACCCCTCTACCCCCACATTGGCCAGTGGACTCATCCATTCTTTGGA
1566  ACAAATCCCCCCCACTCCAAAGTCCATGGATTCAATGGACTCATCCATT
1616  TGTGAGGAGGACTTCTCGCCCTCTGGCTGGAAGCTGATACCTGAAGCACT
1666  CCCAGGCTCATCCTGGGAGCTTTCCTCAGCACCTTCACCTTCCCTCCCAG
1716  TGTAGCCTCCTGTCAGTGGGGCTGGACCCCTTCTAATTCAGAGGTCTCAT
1766  GCCTGCCCCTTGCCCCAGATGCCCAGGTCGTGCACTCTCTGGGATACCAGT
1816  TCAGTCTCCACATTTCTGGTTTCTGTCCCCATAGTACAGTTCTTCAGTG
1866  GACATGACCCCACCCAGCCCTGCTGACCATCTCACCAGAC
1916  ACAAGGGGAAGAAGCAGACATCAGGTGCTGCACTCACTTCTGCCCCTGG
1966  GGAGTTGGGAAAGGAACGAACCCTGGCTGGAGGGGATAGGAGGGCTTTT
```

FIG. 1H

```
2016 AATTTATTCTTTTCTGTTGAGGCTTCCCCTCTCTGAGCCAGTTTTCA
2066 TTTCTTCCTGGTGGCATTAGCCACTCCCTGCTCTCACTCCCAGACCTGTT
2116 CCCACAACTGGGGAGGTAGGCTGGGAGCAAAGGAGAGGGTGGGACCCAG
2166 TTTTGCGTGGTTGGTTTTTATTAATTATCTGGATAACAGCAAAAAACTG
2216 AAAATAAAGAGAGAGAGAAAAAAAAA
```

FIG. 2A

```
                   10         20         30         40         50
Human LPAAT     1  MDLWPGAWM- ----LLLLLF LL-LLFLLPT LWFCSPSAKY F-----FKMA
Yeast LPAAT     1  MSV-IGRFLY YLRSVL-VVL AL-AG----- ---C------ ---------G
E.coli LPAAT    1  M--------- ---------- ----LYIF   RL-IITVIYS ILVCVFGSIY ----------
Maize LPAAT     1  MAI------- ---PLVLVVL PLGLLFLLSG LIVNAIQAVL FVTIRPFSKS
                   60         70         80         90         100
Human LPAAT    51  FYNGWILFLA VLAIPVCAVR GRNVENMKIL RIMLLHIKYL -YGIRVEVRG
Yeast LPAAT    51  FY-------G VIASILCTLI GKQHLAQWIT ARCFYHVMKL MLGLDV----K
E.coli LPAAT   51  --------- ----CLFS   PRNPKHVATF GHMFGRLAPL -FGLKVECRK
Maize LPAAT    51  FYRRINRFLA EL-------- --------L  WLQLVWVDW  WAGVKVQLHA
                   110        120        130        140        150
Human LPAAT   101  AHHF-PPSQ- -PYVVVSNHQ SSLDLLGMME VL--PGRC-- -VPI-AKREL
Yeast LPAAT   101  VVGE-ENLAK KPYIMIANHQ STLDIFMLGR IF--PPGCT- ---VTAKKSL
E.coli LPAAT  101  PTDA-ESYG- -NAIYIANHQ NNYDMVTASN IVQ-PP---- TVTV-GKKSL
Maize LPAAT   101  DEETYRSMGK EHALIISNHR SDIDWL-IGW ILAQRSGCLG STLAVMKKSS
                   160        170        180        190        200
Human LPAAT   151  LWAGSAGLAC W---LAGVIF IDRKRTGDAI SVMSEVAQTL LTQDVRVWV-
Yeast LPAAT   151  KYVPFLG--- WFMALSGTYF LDRSKRQEAI DTLNKGLENV KKNKRALWV-
E.coli LPAAT  151  LWIPFFGQLY W---LTGNLL IDRNNRTKAH GTIAEVVNHF KKRRISIWM-
Maize LPAAT   151  KFLPVIGWSM WF---AEYLF LERS-WAKDE KTLKWGLQRL KDFPRPFWLA
                   210        220        230        240        250
Human LPAAT   201  -FPEGTRNHN GS-------- ---------- MLPFKRGAFH LAVQAQVPIV
Yeast LPAAT   201  -FPEGTRSYT SEL------- ---------- MLPFKKGAFH LAQQGKIPIV
E.coli LPAAT  201  -FPEGTRSRG RGL------- --------T  -LPFKTGAFH AAIAAGVPII
Maize LPAAT   201  LFVEGTRFTP AKLLAAQEYA ASQGLPAPRN VLIPRTKGFV SAVSIMRDFV
```

FIG. 2B

```
                        260         270         280         290         300
Human LPAAT   251  PIVMSSYQDF  YCKKERRFTS  GQCQVRVLPP  VPTEGLTPDD  VPALADR---
Yeast LPAAT   251  PVVVSNTSTL  VSPKYGVFNR  GCMIVRILKP  ISTENLTKDK  IGEFAEK---
E.coli LPAAT  251  PVCVSTTSNK  I--NLNRLHN  GLVIVEMLPP  IDVSQYGKDQ  VRELAAH---
Maize LPAAT   251  PAIYDTT--V  IVPKDSPQPT  MLRILKGQSS  VIHVRMKRHA  MSEMPKSDED 310         320         330         340         350
Human LPAAT   301  ----------  VRHSMLTV-F  REISTDGRGG  GDYLKKPGGG  G*........
Yeast LPAAT   301  ----------  VRDQMVDT-L  KEIGYSPAIN  DTTLPPQ---  ----------
E.coli LPAAT  301  ----------  CRSIMEQK-I  AELDKEVAE-  ----REAAGK  V*........
Maize LPAAT   301  VSKWCKDIFV  AKDALLDKHL  ATGTFDEEIR  PIGRPVKSLL  VTLFWSCLLL 360         370         380         390         400
Human LPAAT   351  ..........  ..........  ..........  ..........  ..........
Yeast LPAAT   351  --AIEY---A  AL------Q  HDKKVNKKIK  NEPVPSVSIS  NDVNTHNEGS
E.coli LPAAT  351  ..........  ..........  ..........  ..........  ..........
Maize LPAAT   351  FGAIEFFKWT  QLLSTWRGVA  FTAAGMALVT  GVMHVFIMFS  QA-----ERS 410         420         430         440         450
Human LPAAT   401  ..........  ..........  ..........  ..........  ..........
Yeast LPAAT   401  S-------V  KKMH*.....  ..........  ..........  ..........
E.coli LPAAT  401  ..........  ..........  ..........  ..........  ..........
Maize LPAAT   401  SSARAARNRV  KKE*......  ..........  ..........  ..........
```

FIG. 3A

```
         10         20         30         40         50         60
GGAGCGAGCT GGCGGCGCCG TCGGGGCCCG GGCCGGGCCA TGGAGCTGTG GCCGTGTCTG 70         80         90        100        110        120
GCCGCGGCGC TGCTGTTGCT GCTGCTGCTG GTGCAGCTGA GCCGGCGGGC CGAGTTCTAC 130        140        150        160        170        180
GCCAAGGTCG CCCTGTACTG CGCGCTGTGC TTCACGGTGT CCGCCGTGGC CTCGCTCGTC 190        200        210        220        230        240
TGCCTGCTGT GCCACGGCGG CCGGACGGTG GAGAACATGA GCATCATCGG CTGGTTCGTG 250        260        270        280        290        300
CGAAGCTTCA AGTACTTTTA CGGGCTCCGC TTCGAGGTGC GGGACCCCGC CAGGCTGCAG 310        320        330        340        350        360
GAGGCCCGTC CCTGTGTCAT CGTCTCCAAC CACCAGAGCA TCCTGGACAT GATGGGCCTC 370        380        390        400        410        420
ATGGAGGTCC TTCCGGAGCG CTGCGTGCAG ATCGCCAAGC GGGAGCTGCT CTTCCTGGGG 430        440        450        460        470        480
CCCGTGGGGC TCATCATGTA CCTCGGGGGC GTCTTCTTCA TCAACCGGCA GCGCTCTAGC 490        500        510        520        530        540
ACTGCCATGA CAGTGATGGC CGACCTGGGC GAGGCGCATG GTCAGGGAGAA CCTCAAAGTG
```

FIG. 3B

```
550        560        570        580        590        600
TGGATCTATC CCGAGGGTAC TCGCAACGAC AATGGGGACC TGCTGCCTTT TAAGAAGGGC
          610        620        630        640        650        660
GCCTTCTACC TGGCAGTCCA GGCACAGGTG CCCATCGTCC CCGTGGTGTA CTCTTCCTTC
          670        680        690        700        710        720
TCCTCCTTCT ACAACACCAA GAAGAAGTTC TTCACTTCAG GAACAGTCAC AGTGCAGGTG
          730        740        750        760        770        780
CTGGAAGCCA TCCCCACCAG CGGCCTCACT TCCCTGCGCT CGTGGACACC
          790        800        810        820        830        840
TGCCACCGGG CCATGAGGAC CACCTTCCTC CACATCTCCA AGACCCCCCA GGAGAACGGG
          850        860        870        880        890        900
GCCACTGCGG GGTCTGGCGT GCAGCCGGCC CAGTAGCCCA GACCACGGCA GGGCATGACC
          910        920        930        940        950        960
TGGGGAGGGC AGGTGGAAGC CGATGGCTGG AGGATGGGCA GAGGGGACTC CTCCCGGCTT
          970        980        990        1000       1010       1020
CCAAATACCA CTCTGTCCGG CTCCCCCAGC TCTCACTCAG CCCGGGAAGC AGGAAGCCCC
          1030       1040       1050       1060       1070       1080
TTCTGTCACT GGTCTCAGAC ACAGGCCCCT GGTGTCCCCT GCAGGGGGCT CAGCTGGACC
```

FIG. 3C

```
     1090        1100        1110        1120        1130        1140
CTCCCCGGGC  TCGAGGGCAG  GGACTCGCGC  CCACGGCACC  TCTGGGNGCT  GGGNTGATAA 1150        1160        1170        1180        1190        1200
AGATGAGGCT  TGCGGCTGTG  GCCCGCTGGT  GGGCTGAGCC  ACAAGGCCCC  CGATGGCCCA 1210        1220        1230        1240        1250        1260
GGAGCAGATG  GGAGGACCCC  GAGGCCAGGA  GTCCCAGACT  CACGCCACCT  GGGCCACAGG 1270        1280        1290        1300        1310        1320
GAGCCGGGAA  TCGGGGCCTG  CTGCTCCTGC  TGGCCTGAAG  AATCTGTGGG  GTCAGCACTG 1330        1340        1350        1360        1370        1380
TACTCCGTTG  CTGTTTTTTT  ATAAACACAC  TCTTTGGAAAA  AAAAAAAAA  AAAAAAAAA 1390        1400        1410        1420        1430        1440
AAA.......  ..........  ..........  ..........  ..........  ..........
```

FIG. 4A

```
        10         20         30         40         50
GGAGCGAGCCGCCGGGCCGCCGTCGGGGGCCGCGGGGCC ATG GAG CTG TGG CCG
                                        Met Glu Leu Trp Pro 60         70         80         90        100
TGT CTG GCC GCG GCG CTG CTG TTG CTG CTG CTG CTG CAG CTG
Cys Leu Ala Ala Ala Leu Leu Leu Leu Leu Leu Leu Gln Leu
                      10                              20

100        110        120        130        140
AGC CGC GCG GCC GAG TTC TAC GCC AAG GTC GCC CTG TAC TGC GCG
Ser Arg Ala Ala Glu Phe Tyr Ala Lys Val Ala Leu Tyr Cys Ala
                                             30

150        160        170        180
CTG TGC TTC ACG GTG TCC GCC GTG GCC TCG CTC GTC TGC CTG CTG
Leu Cys Phe Thr Val Ser Ala Val Ala Ser Leu Val Cys Leu Leu
                   40                                     50

190        200        210        220        230
TGC CAC GGC GGC CGG ACG GTG GAG AAC ATG AGC ATC ATC GGC TGG
Cys His Gly Gly Arg Thr Val Glu Asn Met Ser Ile Ile Gly Trp
                                         60
```

FIG. 4B

```
        240             250             260             270
TTC GTG CGA AGC TTC AAG TAC TTT TAC GGG CTC CGC TTC GAG GTG
Phe Val Arg Ser Phe Lys Tyr Phe Tyr Gly Leu Arg Phe Glu Val
                         70                               80

280             290             300             310             320
CGG GAC CCG CGC AGG CTG CAG GAG GCC CGT CCC TGT GTC ATC GTC
Arg Asp Pro Arg Arg Leu Gln Glu Ala Arg Pro Cys Val Ile Val
                                         90

330             340             350             360
TCC AAC CAC CAG AGC ATC CTG GAC ATG ATG GGC CTC ATG GAG GTC
Ser Asn His Gln Ser Ile Leu Asp Met Met Gly Leu Met Glu Val
                100                                      110

370             380             390             400             410
CTT CCG GAG CGC TGC GTG CAG ATC GCC AAG CGG GAG CTG CTC TTC
Leu Pro Glu Arg Cys Val Gln Ile Ala Lys Arg Glu Leu Leu Phe
                                        120

420             430             440             450
CTG GGG CCC GTG GGC CTC ATC ATG TAC CTC GGG GGC GTC TTC TTC
Leu Gly Pro Val Gly Leu Ile Met Tyr Leu Gly Gly Val Phe Phe
                130                                      140

460             470             480             490             500
ATC AAC CGG CAG CGC TCT AGC ACT GCC ATG ACA GTG ATG GCC GAC
Ile Asn Arg Gln Arg Ser Ser Thr Ala Met Thr Val Met Ala Asp
                                        150
```

FIG. 4C

```
     510            520            530            540
CTG GGC GAG CGC ATG GTC AGG GAG AAC CTC AAA GTG TGG ATC TAT
Leu Gly Glu Arg Met Val Arg Glu Asn Leu Lys Val Trp Ile Tyr
             160                               170

550            560            570            580            590
CCC GAG GGT ACT CGC AAC GAC AAT GGG GAC CTG CTG CCT TTT AAG
Pro Glu Gly Thr Arg Asn Asp Asn Gly Asp Leu Leu Pro Phe Lys
                                    180

600            610            620            630
AAG GGC GCC TTC TAC CTG GCA GTC CAG GCA CAG GTG CCC ATC GTC
Lys Gly Ala Phe Tyr Leu Ala Val Gln Ala Gln Val Pro Ile Val
             190                               200

640            650            660            670            680
CCC GTG GTG TAC TCT TCC TTC TCC TAC AAC ACC AAG AAG
Pro Val Val Tyr Ser Ser Phe Ser Tyr Asn Thr Lys Lys
                                    210

690            700            710            720
AAG TTC ACT TCA GGA ACA GTC ACA GTG CAG GTG CTG GAA GCC
Lys Phe Thr Ser Gly Thr Val Thr Val Gln Val Leu Glu Ala
             220                               230
```

FIG. 4D

```
730                   740                   750                   760                   770
ATC CCC ACC AGC GGC CTC ACT GCG GCG GAC GTC CCT GCG CTC GTG
Ile Pro Thr Ser Gly Leu Thr Ala Ala Asp Val Pro Ala Leu Val
                                                          240

780                   790                   800                   810
GAC ACC TGC CAC CGG GCC ATG AGG ACC ACC TTC CTC CAC ATC TCC
Asp Thr Cys His Arg Ala Met Arg Thr Thr Phe Leu His Ile Ser
                250                                                       260

820                   830                   840                   850                   860
AAG ACC CCC CAG GAG AAC GGG GCC ACT GCG GGG TCT GGC GTG CAG
Lys Thr Pro Gln Glu Asn Gly Ala Thr Ala Gly Ser Gly Val Gln
                                                          270

870                   880                   890                   900                   910                   920
CCG GCC CAG TAG CCCAGACCACGGCCAGGGCCATGACCTGGGGAGGGCAGGTGGAAGC
Pro Ala Gln ***

930
        940        950        960        970        980
CGATGGCTGGAGGATGGGCAGAGGGACTCCTCCCGGCTTCCAAATACCACTCTGTCCGG 990
        1000       1010       1020       1030       1040
CTCCCCCCAGTCTCACTCAGCCCGGGAAGCAGGAAGCCCCCTTCTGTCACTGGTCTCAGAC
        1050       1060       1070       1080       1090       1100
ACAGGCCCCTGTGTCCCCTGCAGCCCTGGACCCTGGACCCCTCCCCCGGCTCGAGGGCAG
```

FIG. 4E

```
       1120       1130       1140       1150       1160
1110 GGACTCGCGCCCACGGCCACCTCTGGGNGCTGGGNTGATAAAGATGAGGCTTGCGGCTGTG 1180       1190       1200       1210       1220
1170 GCCCGCTGGTGGGCTGAGCCACAAGGCCCCGATGGCCCAGGAGCAGATGGGGAGGACCCC 1240       1250       1260       1270       1280
1230 GAGGCCAGGAGAGTCCCAGACTCACGCACCCTGGGCCACAGGCCGGGAATCGGGGCCTG 1300       1310       1320       1330       1340
1290 CTGCTCCTGCTGGCCTGAAGAATCTGTGGGTCAGCACTGTACTCCGTTGCTGTGTTTTTT 1360       1370       1380
1350 ATAAACACACTCTTGGAAAAAAAAAAAAAAAAAAAAA
```

Alignment of LPAAT Sequences.

FIG. 5B

```
                  110         120         130         140         150
Human LPAAT-β  101 GWFVRSFKY- --FYGIRFEV RDPRRLQEAR PCVIVSNHQS ILDMMGIMEV
Human LPAAT-α  101 RLMLHIKY-- ---LYGIRVEV RGAHHFPPSQ PYVVVSNHQS SLDLLGVMEV
Yeast LPAAT    101 CFY-HVMKL- -MLGLDVKV  VGEENAK-K  PYIMIANHQS TLDIFMGRI
E.coli LPAAT   101 GHMFGRL--- APLFGLKVEC RKPTDAESYG NAIYIANHQN NYDMVTASNI
H.influenzae   101 ARWFGRL-FT YPLFGLKVEH RIPQDQKQIS RAIYIGNHQN NYDMVTISYM
S.typhimuriu   101 GHMFGRL-FT APLFGLKVEC RKPADAENYG NAIYIANHQN NYDMVTAANI
L.douglassi    101 GHIIGGLV-- IMIYGIPIKI QGSEHIKKRA IFTYISNHAS PIDAFFVML
C.nucifera     101 GHVIGRMLFT MWILGNPITI EGSEFSNIRA I--YIQNHAS LVDIFIIMWL 160         170         180         190         200
Human LPAAT-β  151 LPERCVQIAK RELLFLGPV- -GLIMYLGGV FFINRQRSST AMT--VMAIL
Human LPAAT-α  151 LPGRCVPIAK RELLWAGSA- -GLACWLAGV IFIDRKRIGD AIS--VMSEV
Yeast LPAAT    151 FPPGCIVIAK KSLKVPFL-- -GWFMALSGT YFLDRSKRQE AID--TINKG
E.coli LPAAT   151 VQPPIVTVGK KSLIWIPFF- --GQLYWLTGN LLIDRNNRTK AHG--TIAEV
H.influenzae   151 VQPRIVSVGK KSLIWIPFF  TGILYWTGN  IFLDRENRTK AHN--TMSQL
S.typhimuriu   151 VQPPIVTVGK KSLIWIPFF  TGQLYWLTGN LLIDRNNRAK AHS--TIAAV
L.douglassi    151 APIGTVGVAK KEVIWYPILG Q--LYTLAH  IRIDRSNPAA AIQSFIMKEA
C.nucifera     151 IPKGTVTIAK KEIIWYPLFG QFTLYVLANH QRIDRSNPSA AIES--IKEV
```

FIG. 5C

|  |  | 210 | 220 | 230 | 240 | 250 |
|---|---|---|---|---|---|---|
| Human LPAAT-β | 201 | GERMRENLK | VWIYPEGTRN | DNGDL—LPF | KKGAFYL—A | VQAQVPIVPV |
| Human LPAAT-α | 201 | AQILLIQDVR | VWVFPEGTRN | HNGSM—LPF | KRGAFHL—A | VQAQVPIVPI |
| Yeast LPAAT | 201 | LENVKKNKRA | LWVFPEGTRS | YTSELIMLPF | KKGAFHL—A | QQKIPIVPV |
| E.coli LPAAT | 201 | VNHFKKRRLS | IWMFPEGTRS | RGRGL—LPF | KTGAF—HAA | IAAGVPIIPV |
| H.influenzae | 201 | ARRINDNLS | IWMFPEGTRN | RGRGL—LPF | KTGAFIFHAA | ISAGVPIIPV |
| S.typhimuriu | 201 | VNHFKKRRLS | IWMFPEGTRS | RGRGL—LPF | KIGAFIFHAA | IAAGVPIIPV |
| L.douglassi | 201 | VRVITEKNLS | LIMFPEGTRS | GDGRL—LPF | KKGFVHL—A | LQSLPIVPM |
| C.nucifera | 201 | ARAWKKNLS | LIIFPEGTRS | KTGRL—LPF | KKGFIHFTIA | LQIRLPIVPM |

|  |  | 260 | 270 | 280 | 290 | 300 |
|---|---|---|---|---|---|---|
| Human LPAAT-β | 251 | VYSSFSS—F | YNTKKKFFTS | GIVIVQVLFA | IPTSGLTAAD | VPALVDICR |
| Human LPAAT-α | 251 | VMSSYQD—F | YCKKERRFTS | GQQVRVLPP | VPTEGITPDD | VPALADRVRH |
| Yeast LPAAT | 251 | VVSNIST—L | VSPKYGVFNR | GCMIVRLLKP | ISTENLITKDK | IGEFAEKVRD |
| E.coli LPAAT | 251 | CVSTTS—— | NKINLNRIHN | GLVIVEMLPP | IDVSQYGKDQ | VRELAAHCR— |
| H.influenzae | 251 | VCSSTH—— | NKINLNRWDN | GKVICEIMDP | IDVSGYTKDN | VRDLAAYCHF |
| S.typhimuriu | 251 | CVSNIS—— | NKVNLNRINN | GLVIVEMLPP | VDVSEYGKDQ | VRELAAHCRF |
| L.douglassi | 251 | ILIGTHLAWF | TRKGIFRVRP | VPITVKYLPP | INTDDWTVDK | IDDYVKMIHD |
| C.nucifera | 251 | VLIGTHLAW— | —RKNSLRVRP | APITVKYFSP | IKTDDWEEK | INHYVEMIHF |

FIG. 5D

```
                        310         320         330         340         350
Human LPAAT-β    301  AMRTIFIHIS KTPQENGATA GSGVQPAQ*  ---------- ----------
Human LPAAT-α    301  SMLTVFREIS TDGRGGDYL  KKPGQGG*   ---------- ----------
Yeast LPAAT      301  QMVDILKEIG YSPAINDTTL PPQAIEYAAL QHDKKVNKKI KNEPVPSVSI
E.coli LPAAT     301  -SIMEQKIAE LDKEVA--ER EAAGKV*    ---------- ----------
H.influenzae     301  TDLMEKRIAE LDEEIA---- --KGN*     ---------- ----------
S.typhimuriu     301  TALMEQKIAE LDKEVA--ER EATGKV*    ---------- ----------
L.douglassi      301  IYVRNLPASQ KPLGS--TNR ---S-K*    ---------- ----------
C. nucifera      301  TALYVDHLPE SQKPLVSKGR DASGRSNS*  ---------- ----------

360         370         380         390
Human LPAAT-β    351  ---------- ---------- ---------- ..........
Human LPAAT-α    351  ---------- ---------- ---------- ..........
Yeast LPAAT      351  SNDVNTHNEG SSVKKMH*    ---------- ..........
E.coli LPAAT     351  ---------- ---------- ---------- ..........
H.influenzae     351  ---------- ---------- ---------- ..........
S.typhimuriu     351  ---------- ---------- ---------- ..........
L.douglassi      351  ---------- ---------- ---------- ..........
C. nucifera      351  ---------- ---------- ---------- ..........
```

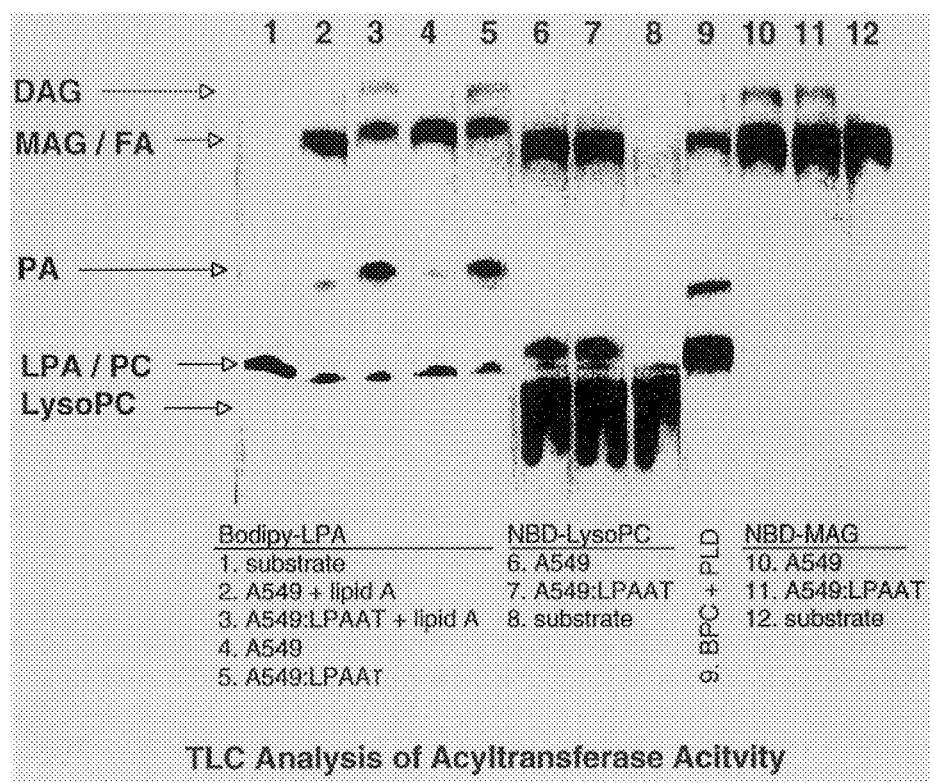

Induction of TNF in A549 LPAAT or A549 cells stimulated with mTNF and IL-1

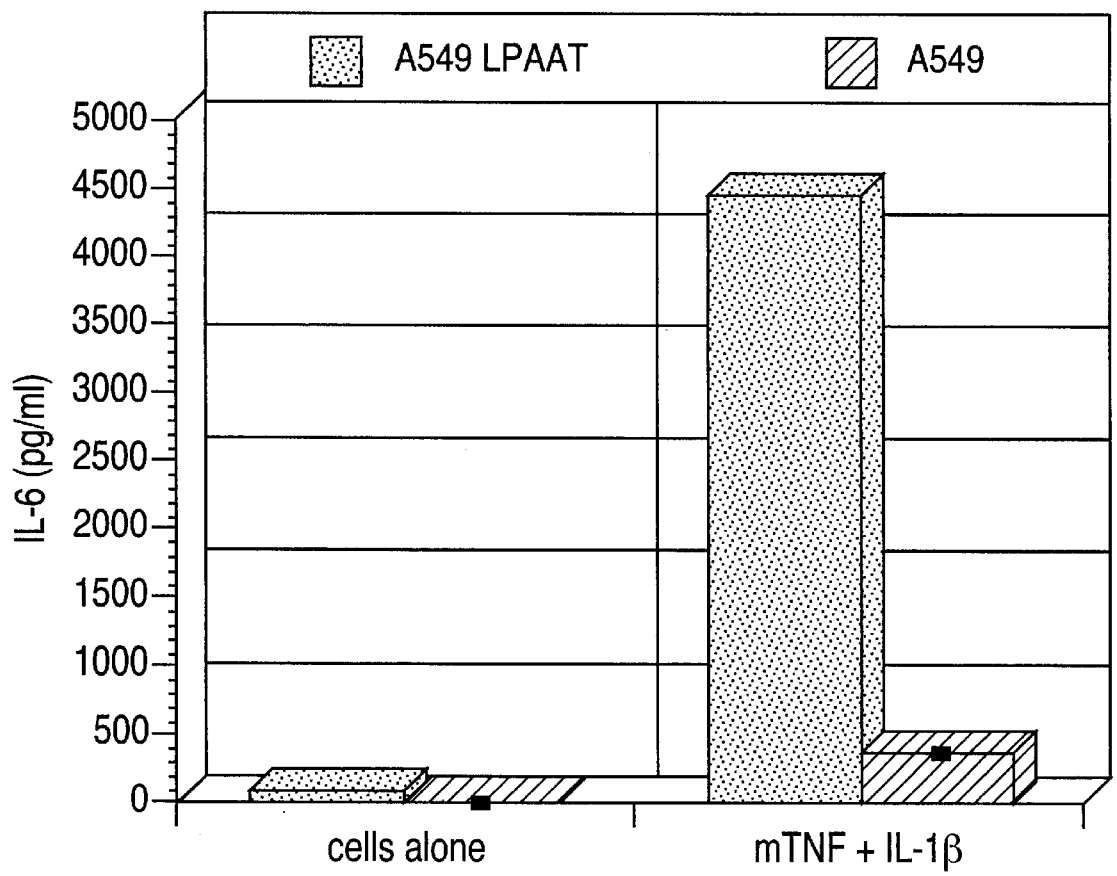
FIG. 8  Induction of IL-6 in A549 LPAAT or A549 cells stimulated with mTNF and IL-1

FIG. 9A
Translated sequence of human LPAAT-γ1

```
TCTATGAAACCAACATACATGGCGTTTGCATCACAGTTGGAGTCAGATGTGAGCCCGGAG     60
GGCAGGTGTCTGGCTTGTCCACCCGGAAGCCCTGAGGGCAGCTGTTCCCACTGGCTCTGC    120
TGACCTTGTGCCTTGGACGGCTGTCCTCAGCGAGGGGCCGTGCACCCGCTCCTGAGCAGC    180
GCC ATG GGC CTG CTG GCC TTC CTG AAG ACC CAG TTC GTG CTG CAC      225
    Met Gly Leu Leu Ala Phe Leu Lys Thr Gln Phe Val Leu His
            5                       10
CTG CTG GTC GGC TTT GTC TTC GTG GTG AGT GGT CTG GTC ATC AAC      270
Leu Leu Val Gly Phe Val Phe Val Val Ser Gly Leu Val Ile Asn
15                  20                  25
TTC GTC CAG CTG TGC ACG CTG GCG CTC TGG CCG GTC AGC AAG CAG      315
Phe Val Gln Leu Cys Thr Leu Ala Leu Trp Pro Val Ser Lys Gln
30                  35                  40
CTC TAC CGC CGC CTC AAC TGC CGC CTC GCA TAC TCA CTC TGG AGC      360
Leu Tyr Arg Arg Leu Asn Cys Arg Leu Ala Tyr Ser Leu Trp Ser
45                  50                  55
CAA CTG GTC ATG CTG CTG GAG TGG TGG TCC TGC ACG GAG TGT ACA      405
Gln Leu Val Met Leu Leu Glu Trp Trp Ser Cys Thr Glu Cys Thr
60                  65                  70
CTG TTC ACG GAC CAG GCC ACG GTA GAG CGC TTT GGG AAG GAG CAC      450
Leu Phe Thr Asp Gln Ala Thr Val Glu Arg Phe Gly Lys Glu His
75                  80                  85
GCA GTC ATC ATC CTC AAC CAC AAC TTC GAG ATC GAC TTC CTC TGT      495
Ala Val Ile Ile Leu Asn His Asn Phe Glu Ile Asp Phe Leu Cys
90                  95                  100
GGG TGG ACC ATG TGT GAG CGC TTC GGA GTG CTG GGG AGC TCC AAG      540
Gly Trp Thr Met Cys Glu Arg Phe Gly Val Leu Gly Ser Ser Lys
105                 110                 115
GTC CTC GCT AAG AAG GAG CTG CTC TAC GTG CCC CTC ATC GGC TGG      585
Val Leu Ala Lys Lys Glu Leu Leu Tyr Val Pro Leu Ile Gly Trp
120                 125                 130
ACG TGG TAC TTT CTG GAG ATT GTG TTC TGC AAG CGG AAG TGG GAG      630
Thr Trp Tyr Phe Leu Glu Ile Val Phe Cys Lys Arg Lys Trp Glu
135                 140                 145
GAG GAC CGG GAC ACC GTG GTC GAA GGG CTG AGG CGC CTG TCG GAC      675
Glu Asp Arg Asp Thr Val Val Glu Gly Leu Arg Arg Leu Ser Asp
150                 155                 160
TAC CCC GAG TAC ATG TGG TTT CTC CTG TAC TGC GAG GGG ACG CGC      720
Tyr Pro Glu Tyr Met Trp Phe Leu Leu Tyr Cys Glu Gly Thr Arg
165                 170                 175
TTC ACG GAG ACC AAG CAC CGC GTT AGC ATG GAG GTG GCG GCT GCT      765
Phe Thr Glu Thr Lys His Arg Val Ser Met Glu Val Ala Ala Ala
180                 185                 190
AAG GGG CTT CCT GTC CTC AAG TAC CAC CTG CTG CCG CGG ACC AAG      810
Lys Gly Leu Pro Val Leu Lys Tyr His Leu Leu Pro Arg Thr Lys
195                 200                 205
GGC TTC ACC ACC GCA GTC AAG TGC CTC CGG GGG ACA GTC GCA GCT      855
Gly Phe Thr Thr Ala Val Lys Cys Leu Arg Gly Thr Val Ala Ala
210                 215                 220
GTC TAT GAT GTA ACC CTG AAC TTC AGA GGA AAC AAG AAC CCG TCC      900
Val Tyr Asp Val Thr Leu Asn Phe Arg Gly Asn Lys Asn Pro Ser
225                 230                 235
CTG CTG GGG ATC CTC TAC GGG AAG AAG TAC GAG GCG GAC ATG TGC      945
Leu Leu Gly Ile Leu Tyr Gly Lys Lys Tyr Glu Ala Asp Met Cys
240                 245                 250
GTG AGG AGA TTT CCT CTG GAA GAC ATC CCG CTG GAT GAA AAG GAA      990
Val Arg Arg Phe Pro Leu Glu Asp Ile Pro Leu Asp Glu Lys Glu
255                 260                 265
GCA GCT CAG TGG CTT CAT AAA CTG TAC CAG GAG AAG GAC GCG CTC     1035
```

FIG. 9B

```
Ala Ala Gln Trp Leu His Lys Leu Tyr Gln Glu Lys Asp Ala Leu
270             275                 280
CAG GAG ATA TAT AAT CAG AAG GGC ATG TTT CCA GGG GAG CAG TTT     1080
Gln Glu Ile Tyr Asn Gln Lys Gly Met Phe Pro Gly Glu Gln Phe
285                 290                 295
AAG CCT GCC CGG AGG CCG TGG ACC CTC CTG AAC TTC CTG TCC TGG     1125
Lys Pro Ala Arg Arg Pro Trp Thr Leu Leu Asn Phe Leu Ser Trp
300                 305                 310
GCC ACC ATT CTC CTG TCT CCC CTC TTC AGT TTT GTC TTG GGC GTC     1170
Ala Thr Ile Leu Leu Ser Pro Leu Phe Ser Phe Val Leu Gly Val
315                 320                 325
TTT GCC AGC GGA TCA CCT CTC CTG ATC CTG ACT TTC TTG GGG TTT     1215
Phe Ala Ser Gly Ser Pro Leu Leu Ile Leu Thr Phe Leu Gly Phe
330                 335                 340
GTG GGA GCA GCT TCC TTT GGA GTT CGC AGA CTG ATA GGA GTA ACT     1260
Val Gly Ala Ala Ser Phe Gly Val Arg Arg Leu Ile Gly Val Thr
345                 350                 355
GAG ATA GAA AAA GGC TCC AGC TAC GGA AAC CAA GAG TTT AAG AAA     1305
Glu Ile Glu Lys Gly Ser Ser Tyr Gly Asn Gln Glu Phe Lys Lys
360                 365                 370
AAG GAA TAA TTAATGGCTGTGACTGAACACACGCGGCCCTGACGGTGGTATCCAGTT    1362
Lys Glu ***
AACTCAAAACCAACACACAGAGTGCAGGAAAAGACAATTAGAAACTATTTTTCTTATTAA   1422
CTGGTGACTAATATTAACAAAACTTGAGCCAAGAGTAAAGAATTCAGAAGGCCTGTCAGG   1482
TGAAGTCTTCAGCCTCCCACAGCGCAGGGTCCCAGCATCTCCACGCGCGCCCGTGGGAGG   1542
TGGGTCCGGCCGGAGAGGCCTCCCGCGGACGCCGTCTCTCCAGAACTCCGCTTCCAAGAG   1602
GGACCTTTGGCTGCTTTCTCTCCTTAAACTTAGATCAAATTTTAAAAAAAAAAAAAAA    1660
```

FIG. 10A
Translated sequence of LPAAT-γ2 cDNA

```
CACGCTGGCGCTCTGGCCGGTCAGCAAGCAGCTCTACCGCCGCCTCAACTGCCGCCTCGCC        61
TACTCACTCTGGAGCCTAGCACAAAACTAGAAGCAACCCAAGCACCTGTCACTGGAGACT        121
AATTATGCGGCACCCATACAGGGACCCTCTGCGGCCATCATGGAGAGCCTTCATCTTGCC        181
CGTACAGTTTTAAGCGAAAAGGAAGTATACAACAAAGTCCATAACTGGTC ATG CTG         238
                                                   Met Leu
```

| | | | | | | | | | | | | |
|---|---|---|---|---|---|---|---|---|---|---|---|---|
| CTG | GAG | TGG | TGG | TCC | TGC | ACG | GAG | TGT | ACA | CTG | TTC | ACG GAC CAG | 283
| Leu | Glu | Trp | Trp | Ser | Cys | Thr | Glu | Cys | Thr | Leu | Phe | Thr Asp Gln |
| | | 5 | | | | | 10 | | | | | 15 |

```
GCC ACG GTA GAG CGC TTT GGG AAG GAG CAC GCA GTC ATC ATC CTC        328
Ala Thr Val Glu Arg Phe Gly Lys Glu His Ala Val Ile Ile Leu
         20                  25                  30
AAC CAC AAC TTC GAG ATC GAC TTC CTC TGT GGG TGG ACC ATG TGT        373
Asn His Asn Phe Glu Ile Asp Phe Leu Cys Gly Trp Thr Met Cys
         35                  40                  45
GAG CGC TTC GGA GTG CTG GGG AGC TCC AAG GTC CTC GCT AAG AAG        418
Glu Arg Phe Gly Val Leu Gly Ser Ser Lys Val Leu Ala Lys Lys
         50                  55                  60
GAG CTG CTC TAC GTG CCC CTC ATC GGC TGG ACG TGG TAC TTT CTG        463
Glu Leu Leu Tyr Val Pro Leu Ile Gly Trp Thr Trp Tyr Phe Leu
         65                  70                  75
GAG ATT GTG TTC TGC AAG CGG AAG TGG GAG GAG GAC CGG GAC ACC        508
Glu Ile Val Phe Cys Lys Arg Lys Trp Glu Glu Asp Arg Asp Thr
         80                  85                  90
GTG GTC GAA GGG CTG AGG CGC CTG TCG GAC TAC CCC GAG TAC ATG        553
Val Val Glu Gly Leu Arg Arg Leu Ser Asp Tyr Pro Glu Tyr Met
         95                  100                 105
TGG TTT CTC CTG TAC TGC GAG GGG ACG CGC TTC ACG GAG ACC AAG        598
Trp Phe Leu Leu Tyr Cys Glu Gly Thr Arg Phe Thr Glu Thr Lys
        110                 115                 120
CAC CGC GTT AGC ATG GAG GTG GCG GCT GCT AAG GGG CTT CCT GTC        643
His Arg Val Ser Met Glu Val Ala Ala Ala Lys Gly Leu Pro Val
        125                 130                 135
CTC AAG TAC CAC CTG CTG CCG CGG ACC AAG GGC TTC ACC ACC GCA        688
Leu Lys Tyr His Leu Leu Pro Arg Thr Lys Gly Phe Thr Thr Ala
        140                 145                 150
GTC AAG TGC CTC CGG GGG ACA GTC GCA GCT GTC TAT GAT GTA ACC        733
Val Lys Cys Leu Arg Gly Thr Val Ala Ala Val Tyr Asp Val Thr
        155                 160                 165
CTG AAC TTC AGA GGA AAC AAG AAC CCG TCC CTG CTG GGG ATC CTC        778
Leu Asn Phe Arg Gly Asn Lys Asn Pro Ser Leu Leu Gly Ile Leu
        170                 175                 180
TAC GGG AAG AAG TAC GAG GCG GAC ATG TGC GTG AGG AGA TTT CCT        823
Tyr Gly Lys Lys Tyr Glu Ala Asp Met Cys Val Arg Arg Phe Pro
        185                 190                 195
CTG GAA GAC ATC CCG CTG GAT GAA AAG GAA GCA GCT CAG TGG CTT        868
Leu Glu Asp Ile Pro Leu Asp Glu Lys Glu Ala Ala Gln Trp Leu
        200                 205                 210
CAT AAA CTG TAC CAG GAG AAG GAC GCG CTC CAG GAG ATA TAT AAT        913
His Lys Leu Tyr Gln Glu Lys Asp Ala Leu Gln Glu Ile Tyr Asn
        215                 220                 225
CAG AAG GGC ATG TTT CCA GGG GAG CAG TTT AAG CCT GCC CGG AGG        958
Gln Lys Gly Met Phe Pro Gly Glu Gln Phe Lys Pro Ala Arg Arg
        230                 235                 240
CCG TGG ACC CTC CTG AAC TTC CTG TCC TGG GCC ACC ATT CTC CTG       1003
Pro Trp Thr Leu Leu Asn Phe Leu Ser Trp Ala Thr Ile Leu Leu
        245                 250                 255
TCT CCC CTC TTC AGT TTT GTC TTG GGC GTC TTT GCC AGC GGA TCA       1048
Ser Pro Leu Phe Ser Phe Val Leu Gly Val Phe Ala Ser Gly Ser
```

FIG. 10B

```
            260                         265                         270
CCT CTC CTG ATC CTG ACT TTC TTG GGG TTT GTG GGA GCA GCT TCC            1093
Pro Leu Leu Ile Leu Thr Phe Leu Gly Phe Val Gly Ala Ala Ser
            275                         280                         285
TTT GGA GTT CGC AGA CTG ATA GGA GTA ACT GAG ATA GAA AAA GGC            1138
Phe Gly Val Arg Arg Leu Ile Gly Val Thr Glu Ile Glu Lys Gly
            290                         295                         300
TCC AGC TAC GGA AAC CAA GAG TTT AAG AAA AAG GAA TAA TTAATGGC           1185
Ser Ser Tyr Gly Asn Gln Glu Phe Lys Lys Lys Glu ***
            305                         310
TGTGACTGAACACACGCGGCCCTGACGGTGGTATCCAGTTAACTCAAAACCAACACACAG          1245
AGTGCAGGAAAAGACAATTAGAAACTATTTTTCTTATTAACTGGTGACTAATATTAACAA          1305
AACTTGAGCCAAGAGTAAAGAATTCAGAAGGCCTGTCAGGTGAAGTCTTCAGCCTCCCAC          1365
AGCGCAGGGTCCCAGCATCTCCACGCGCGCCCGTGGGAGGTGGGTCCGGCCGGAGAGGCC          1425
TCCCGCGGACGCCGTCTCTCCAGAACTCCGCTTCCAAGAGGGACCTTTGGCTGCTTTCTC         1485
TCCTTAAACTTAGATCAAATTTTAAAAAAAAAAAAAAA                                1523
```

FIG. 11A
Translated sequence of human LPAAT-δ

```
TGAACCCAGCCGGCTCCATCTCAGCTTCTGGTTTCTAAGTCCATGTGCCAAAGGCTGCCAG        61
GAAGGAGACGCCTTCCTGAGTCCTGGATCTTTCTTCCTTCTGGAAATCTTTGACTGTGGG       121
TAGTTATTTATTTCTGAATAAGAGCGTCCACGCATC ATG GAC CTC GCG GGA CTG       175
                                     Met Asp Leu Ala Gly Leu
                                                           5
CTG AAG TCT CAG TTC CTG TGC CAC CTG GTC TTC TGC TAC GTC TTT        220
Leu Lys Ser Gln Phe Leu Cys His Leu Val Phe Cys Tyr Val Phe
            10              15                  20
ATT GCC TCA GGG CTA ATC ATC AAC ACC ATT CAG CTC TTC ACT CTC        265
Ile Ala Ser Gly Leu Ile Ile Asn Thr Ile Gln Leu Phe Thr Leu
            25              30                  35
CTC CTC TGG CCC ATT AAC AAG CAG CTC TTC CGG AAG ATC AAC TGC        310
Leu Leu Trp Pro Ile Asn Lys Gln Leu Phe Arg Lys Ile Asn Cys
            40              45                  50
AGA CTG TCC TAT TGC ATC TCA AGC CAG CTG GTG ATG CTG CTG GAG        355
Arg Leu Ser Tyr Cys Ile Ser Ser Gln Leu Val Met Leu Leu Glu
            55              60                  65
TGG TGG TCG GGC ACG GAA TGC ACC ATC TTC ACG GAC CCG CGC GCC        400
Trp Trp Ser Gly Thr Glu Cys Thr Ile Phe Thr Asp Pro Arg Ala
            70              75                  80
TAC CTC AAG TAT GGG AAG GAA AAT GCC ATC GTG GTT CTC AAC CAC        445
Tyr Leu Lys Tyr Gly Lys Glu Asn Ala Ile Val Val Leu Asn His
            85              90                  95
AAG TTT GAA ATT GAC TTT CTG TGT GGC TGG AGC CTG TCC GAA CGC        490
Lys Phe Glu Ile Asp Phe Leu Cys Gly Trp Ser Leu Ser Glu Arg
            100             105                 110
TTT GGG CTG TTA GGG GGC TCC AAG GTC CTG GCC AAG AAA GAG CTG        535
Phe Gly Leu Leu Gly Gly Ser Lys Val Leu Ala Lys Lys Glu Leu
            115             120                 125
GCC TAT GTC CCA ATT ATC GGC TGG ATG TGG TAC TTC ACC GAG ATG        580
Ala Tyr Val Pro Ile Ile Gly Trp Met Trp Tyr Phe Thr Glu Met
            130             135                 140
GTC TTC TGT TCG CGC AAG TGG GAG CAG GAT CGC AAG ACG GTT GCC        625
Val Phe Cys Ser Arg Lys Trp Glu Gln Asp Arg Lys Thr Val Ala
            145             150                 155
ACC AGT TTG CAG CAC CTC CGG GAC TAC CCC GAG AAG TAT TTT TTC        670
Thr Ser Leu Gln His Leu Arg Asp Tyr Pro Glu Lys Tyr Phe Phe
            160             165                 170
CTG ATT CAC TGT GAG GGC ACA CGG TTC ACG GAG AAG AAG CAT GAG        715
Leu Ile His Cys Glu Gly Thr Arg Phe Thr Glu Lys Lys His Glu
            175             180                 185
ATC AGC ATG CAG GTG GCC CGG GCC AAG GGG CTG CCT CGC CTC AAG        760
Ile Ser Met Gln Val Ala Arg Ala Lys Gly Leu Pro Arg Leu Lys
            190             195                 200
CAT CAC CTG TTG CCA CGA ACC AAG GGC TTC GCC ATC ACC GTG AGG        805
His His Leu Leu Pro Arg Thr Lys Gly Phe Ala Ile Thr Val Arg
            205             210                 215
AGC TTG AGA AAT GTA GTT TCA GCT GTA TAT GAC TGT ACA CTC AAT        850
Ser Leu Arg Asn Val Val Ser Ala Val Tyr Asp Cys Thr Leu Asn
            220             225                 230
TTC AGA AAT AAT GAA AAT CCA ACA CTG CTG GGA GTC CTA AAC GGA        895
Phe Arg Asn Asn Glu Asn Pro Thr Leu Leu Gly Val Leu Asn Gly
            235             240                 245
AAG AAA TAC CAT GCA GAT TTG TAT GTT AGG AGG ATC CCA CTG GAA        940
Lys Lys Tyr His Ala Asp Leu Tyr Val Arg Arg Ile Pro Leu Glu
            250             255                 260
GAC ATC CCT GAA GAC GAT GAC GAG TGC TCG GCC TGG CTG CAC AAG        985
Asp Ile Pro Glu Asp Asp Asp Glu Cys Ser Ala Trp Leu His Lys
            265             270                 275
```

FIG. 11B

```
CTC TAC CAG GAG AAG GAT GCC TTT CAG GAG GAG TAC TAC AGG ACG      1030
Leu Tyr Gln Glu Lys Asp Ala Phe Gln Glu Glu Tyr Tyr Arg Thr
            280                 285                 290
GGC ACC TTC CCA GAG ACG CCC ATG GTG CCC CCC CGG CGG CCC TGG      1075
Gly Thr Phe Pro Glu Thr Pro Met Val Pro Pro Arg Arg Pro Trp
            295                 300                 305
ACC CTC GTG AAC TGG CTG TTT TGG GCC TCG CTG GTG CTC TAC CCT      1120
Thr Leu Val Asn Trp Leu Phe Trp Ala Ser Leu Val Leu Tyr Pro
            310                 315                 320
TTC TTC CAG TTC CTG GTC AGC ATG ATC AGG AGC GGG TCT TCC CTG      1165
Phe Phe Gln Phe Leu Val Ser Met Ile Arg Ser Gly Ser Ser Leu
            325                 330                 335
ACG CTG GCC AGC TTC ATC CTC GTC TTC TTT GTG GCC TCC GTG GGA      1210
Thr Leu Ala Ser Phe Ile Leu Val Phe Phe Val Ala Ser Val Gly
            340                 345                 350
GTT CGA TGG ATG ATT GGT GTG ACG GAA ATT GAC AAG GGC TCT GCC      1255
Val Arg Trp Met Ile Gly Val Thr Glu Ile Asp Lys Gly Ser Ala      366
            355                 360                 365
TAC GGC AAC TCT GAC AGC AAG CAG AAA CTG AAT GAC TGA CTCAGGG      1301
Tyr Gly Asn Ser Asp Ser Lys Gln Lys Leu Asn Asp ***
            370                 375
AGGTGTCACCATCCGAAGGGAACCTTGGGGAACTGGTGGCCTCTGCATATCCTCCTTAGT    1361
GGGACACGGTGACAAAGGCTGGGTGAGCCCCTGCTGGGCACGGCGGAAGTCACGACCTCT    1421
CCAGCCAGGGAGTCTGGTCTCAAGGCCGGATGGGGAGGAAGATGTTTTGTAATCTTTTTT    1481
TCCCCATGTGCTTTAGTGGGCTTTGGTTTTCTTTTTGTGCGAGTGTGTGTGAGAATGGCT    1541
GTGTGGTGAGTGTGAACTTTGTTCTGTGATCATAGAAAGGGTATTTTAGGCTGCAGGGGA    1601
GGGCAGGGCTGGGGACCGAAGGGGACAAGTTCCCCTTTCATCCTTTGGTGCTGAGTTTTC    1661
TGTAACCCTTGGTTGCCAGAGATAAAGTGAAAAGTGCTTTAGGTGAGATGACTAAATTAT    1721
GCCTCCAAGAAAAAAAATTAAAGTGCTTTTCTGGGTCAAAAAAAAAAAAAAA            1774
```

FIG. 12

```
             10          20          30          40          50
LPAAT-γ1   MGLLAFLKTQ  FVLHLLVGFV  FVVSGLVINF  VQ-LCTLALW  PVSKQLYRRL
LPAAT-γ2   ----------  ----------  ----------  ----------  ----------
LPAAT-δ    MDLAGLLKSQ  FLCHLVFCYV  FIASGLIINT  IQ-LFTLLLW  PINKQLFRKI 60          70          80          90         100
LPAAT-γ1   NCRLAYSLWS  QLVMLLEWWS  CTECTLFTDQ  ATVERFGKEH  AVIILNHNFE
LPAAT-γ2   ----------  ---MLLEWWS  CTECTLFTDQ  ATVERFGKEH  AVIILNHNFE
LPAAT-δ    NCRLSYCISS  QLVMLLEWWS  GTECTIFTDP  RAILKYGKEN  AIVVLNHKFE 110         120         130         140         150
LPAAT-γ1   IDFLCGWTMC  ERFGVLGSSK  VLAKKELLYV  PLIGWTWYFL  EIVFCKRKWE
LPAAT-γ2   IDFLCGWTMC  ERFGVLGSSK  VLAKKELLYV  PLIGWTWYFL  EIVFCKRKWE
LPAAT-δ    IDFLCGWSIS  ERFGLLGGSK  VLAKKELAYV  PIIGWMWYFT  EMVFCSRKWE 160         170         180         190         200
LPAAT-γ1   EDRDTVVEGL  RRLSDYPEYM  WFLLYCEGTR  FTETKHRVSM  EVAAAKGLPV
LPAAT-γ2   EDRDTVVEGL  RRLSDYPEYM  WFLLYCEGTR  FTETKHRVSM  EVAAAKGLPV
LPAAT-δ    QDRITVATSL  IHLRDYPEKY  FFLIHCEGTR  FTEKKHEISM  QVARAKGLPR 210         220         230         240         250
LPAAT-γ1   LKYHLLPRTK  GFTTAVKCLR  GTVAAVYDVT  LNF-RGNKNP  SLLGILYGKK
LPAAT-γ2   LKYHLLPRTK  GFTTAVKCLR  GTVAAVYDVT  LNF-RGNKNP  SLLGILYGKK
LPAAT-δ    LKHHLLPRTK  GFAITVRSLR  NVVSAVYDCT  LNF-RNNENP  ILLGVLNGKK 260         270         280         290         300
LPAAT-γ1   YEADMCVRRF  PLEDIPLDEK  EAAQWLHKLY  QEKDALQEIY  NQKGMFPGEQ
LPAAT-γ2   YEADMCVRRF  PLEDIPLDEK  EAAQWLHKLY  QEKDALQEIY  NQKGMFPGEQ
LPAAT-δ    YHADLYVRRI  PLEDIPEDDD  ECSAWLHKLY  QEKDAFQEEY  YRIGTFPETP 310         320         330         340         350
LPAAT-γ1   FKPARRPWTL  LNFLSWATIL  LSPLFSFVLG  VFASGSPLLI  ---LTFLGFV
LPAAT-γ2   FKPARRPWTL  LNFLSWATIL  LSPLFSFVLG  VFASGSPLLI  ---LTFLGFV
LPAAT-δ    MVPPRRPWTL  VNWLFWASIV  LYPFFQFLVS  MIRSGSSLTL  ---ASFILVF 360         370         380
LPAAT-γ1   GAASFGVRRL  IGVTEIEKGS  SYGNQEF--K  KKE*
LPAAT-γ2   GAASFGVRRL  IGVTEIEKGS  SYGNQEF--K  KKE*
LPAAT-δ    FVASVGVRWM  IGVTEIDKGS  AYGNSDSKQK  LND*
```

US 6,300,487 B1

MAMMALIAN LYSOPHOSPHATIDIC ACID ACYLTRANSFERASE

This is a continuation-in-part of U.S. application Ser. No. 08/618,651, filed Mar. 19, 1996, now abandoned.

TECHNICAL FIELD OF THE INVENTION

The present invention provides polypeptides having lysophosphatidic acid acyltransferase (LPAAT) activity and polynucleotides encoding polypeptides having LPAAT activity. The present invention further provides for isolation and production of polypeptides involved in phosphatidic acid metabolism and signaling in mammalian cells, in particular, the production of purified forms of LPAAT.

BACKGROUND OF THE INVENTION

LPAAT, also referred to as 1-acyl sn-glycerol-3-phosphate acyltransferase (EC 2.3.1.51), is known to catalyze the acylation of lysophosphatidic acid (LPA) to phosphatidic acid (PA) by acylating the sn-2 position of LPA with a fatty acid acyl-chain moiety. LPA and PA, while originally identified as intermediates in lipid biosynthesis (Kent, *Anal. Rev. Biochem.* 64:315–343, 1995), have more recently been identified as phospholipid signaling molecules that affect a wide range of biological responses (McPhail et al., *Proc. Natl. Acad. Sci. USA* 92:7931–7935, 1995; Williger et al., *J. Biol. Chem.* 270:29656–29659, 1995; Moolenaar, *Curr. Opin. Cell Biol.* 7:203–210, 1995).

Cellular activation in monocytic and lymphoid cells is associated with rapid upregulation of synthesis of phospholipids (PL) that includes PA, diacylglycerol (DAG) and glycan phosphatidylinositol (PI). PAs are a molecularly diverse group of phospholipid second messengers coupled to cellular activation and mitogenesis (Singer et al., *Exp. Opin. Invest. Drugs* 3:631–643, 1994). PA can be generated through hydrolysis of phosphatidylcholine (PC) (Exton, *Biochim. Biophys. Acta* 1212:26–42, 1994) or glycan PI (Eardley et al., *Science* 251:78–81, 1991; Merida et al., *DNA Cell Biol.* 12:473–479, 1993), through phosphorylation of DAG by DAG kinase (Kanoh et al., *Trends Biochem. Sci.* 15:47–50, 1990) or through acylation of LPA at the SN2 position (Bursten et al., *Am. J. Physiol.* 266:C1093–C1104, 1994).

Compounds that block PA generation and hence diminish lipid biosynthesis and the signal involved in cell activation are therefore of therapeutic interest in, for example, the areas of inflammation and oncology as well as obesity treatment. Therefore, compounds that block LPAAT activity have a similar therapeutic value.

The genes coding for LPAAT have been isolated in bacteria (Coleman, *Mol. Gen. Genet.* 232:295–303, 1992), in yeast (Nagiec et al., *J. Biol. Chem.* 268:22156–22163, 1993) and in plants (Brown et al., *Plant Mol. Biol.* 26:211–223, 1994; and Hanke et al., *Eur J. Biochem.* 232:806–810, 1995; Knutzon, et al., *Plant Physiol.* 109: 999–1006, 1995). Moreover, two human isoforms of LPAAT have been reported (West, et al., *DNA Cell Biol.* 6: 691–701, 1997). These isoforms are denominated LPAATα and LPAATβ (West, et al., *DNA Cell Biol.* 6: 691–701, 1997) and are described herein. There remains, however, a need for the isolation of additional mammalian LPAATs, which can be used, for example, to screen for compounds that inhibit LPAAT activity.

SUMMARY OF THE INVENTION

The present invention provides cDNA sequences, polypeptide sequences, and transformed cells for producing isolated recombinant mammalian LPAAT. The present invention provides four polypeptides corresponding to human LPAAT isoforms. These polypeptides are designated hLPAATα, hLPAATβ, hLPAATγ1, hLPAATγ2, and hLPAATδ. The invention further provides fragments of these polypeptides which are biologically active, i.e., which retain LPAAT activity. LPAAT activity is defined catalyzing acylation of lysophosphatidic acid (LPA) to phosphatidic acid (PA), specifically by acylating the sn-2 position of LPA with a fatty acid acyl-chain moiety.

The present invention further provides nucleic acid sequences encoding hLPAATα, HLPAATβ, hLPAATγ1, hLPAATγ2, and hLPAATδ and polynucleotides coding for biologically active fragments of hLPAATα, hLPAATβ, hLPAATγ1, hLPAATγ2, and hLPAATδ. The invention further provides "biologically active" polynucleotide fragments, which connotes polynucleotide fragments which encode polypeptides having LPAAT activity. The invention further provides purified LPAATs and antisense oligonucleotides for modulation of expression of the genes coding for LPAAT polypeptides. Assays for screening test compounds for their ability to inhibit LPAATs are also provided.

The present invention includes the following polynucleotides coding for hLPAATα, hLPAATβ, hLPAATγ1, hLPAATγ2, and hLPAATδ. The invention provides the DNA sequences of: SEQ ID NO. 1 which encodes for hLPAATα; SEQ ID NO. 6, which encodes hLPAATδ; FIG. 9, which encodes hLPAATγ1 FIG. 10, which encodes hLPAATγ2; and FIG. 11, which encodes and hLPAATδ.

The invention further includes the polypeptides for hLPAATα, hLPAATβ, hLPAATγ1, hLPAATγ2, and hLPAATδ, specifically, the amino acid sequences of: SEQ ID NO. 2, which represents hLPAATα; SEQ ID NO. 7, which represents hLPAATβ; FIG. 9, which represents hLPAATγ1; FIG. 10, which represents hLPAATγ2; and FIG. 11, which represents hLPAATδ.

The invention further comprises biologically active fragments of the amino acid sequences of SEQ ID NO. 2, SEQ ID NO. 7, FIG. 9, FIG. 10, and FIG. 11 or nucleotide fragments of SEQ ID NO. 1, SEQ ID NO. 6, FIG. 9, FIG. 10, and FIG. 11 which encode biologically active LPAAT. The invention further includes polynucleotides which due to the degeneracy of the genetic code encode a polypeptide of SEQ ID NO. 2, SEQ. ID NO. 7, FIG. 9, FIG. 10, and FIG. 11. The invention further includes polynucleotides capable of hybridizing to the nucleic acid sequences of SEQ ID NO. 1, SEQ ID NO. 6, FIG. 9, FIG. 10, and FIG. 11, under high stringency conditions, and which are biologically active.

Also provided by the present invention are vectors containing a DNA sequence encoding a mammalian LPAAT enzyme in operative association with an expression control sequence. Host cells, transformed with such vectors for use in producing recombinant LPAAT, are also provided with the present invention. The inventive vectors and transformed cells are employed in a process for producing recombinant mammalian LPAAT. In this process, a cell line transformed with a DNA sequence encoding LPAAT in operative association with an expression control sequence, is cultured. The claimed process may employ a number of known cells as host cells for expression of the LPAAT polypeptide, including, for example, mammalian cells, yeast cells, insect cells and bacterial cells. The present invention further provides transformed cells that expresses active mammalian LPAAT.

The present invention further provides methods for identifying compounds that increase or decrease LPAAT activity, i.e., acylation of LPA to PA. Because PA concentration is involved in numerous cellular pathways, compounds that increase or decrease acylation of LPA to PA are useful in regulating a number of cellular pathways. Such compounds can be used, for example, to augment trilineage hematopoiesis after cytoreductive therapy or to inhibit inflammation following hypoxia and reoxygenation injury (e.g., sepsis, trauma, and ARDS). Moreover, the present invention contemplates the use of such compounds in an in vitro or in vivo context.

The present invention further includes: An isolated polynucleotide encoding a polypeptide having Lysophosphatidic Acid Acyltransferase (LPAAT) activity, comprising a nucleotide sequence selected from the group consisting of:

(a) the DNA sequence of FIG. 9, FIG. 10, or FIG. 11 and biologically active fragments thereof; and (b) a DNA sequence which encodes the polypeptide of FIG. 9, FIG. 10, or FIG. 11 and biologically active fragments thereof.

An isolated polypeptide having LPAAT activity, comprising the amino acid sequence of FIG. 9, FIG. 10, or FIG. 11 and biologically active fragments thereof.

A method for screening one or more compounds to determine whether the one or more compounds increases or decreases LPAAT activity, comprising:

(a) contacting the polypeptide of the present invention with one or more substrates for the polypeptide and with the one or more compounds; and (b) measuring whether the LPAAT activity of the polypeptide is increased or decreased by the one or more compounds.

A method of expressing the polypeptide of the present invention, comprising:

(a) introducing into a cell a polynucleotide comprising a nucleotide sequence selected from the group consisting of:

(i) the DNA sequence of FIG. 9, FIG. 10, or FIG. 11 and biologically active fragments thereof; and (ii) a DNA sequence which encodes the polypeptide of FIG. 9, FIG. 10, or FIG. 11 and biologically active fragments thereof, wherein the polynucleotide is operably linked to a promoter; and (b) maintaining or growing said cell under conditions that result in the expression of the polypeptide.

An isolated polynucleotide encoding a polypeptide having Lysophosphatidic Acid Acyltransferase (LPAAT) activity, comprising a DNA sequence capable of hybridizing under high stringency conditions to the complement of the DNA sequences, (a) or (b), described above, and which encodes a polypeptide having LPAAT activity.

BRIEF DESCRIPTION OF THE DRAWINGS

FIG. 1 shows the DNA sequence of the cDNA insert of pZplat.11 encoding hLPAATα (SEQ ID NO: 1).

FIG. 2 shows amino acid sequence alignment of the human LPAATα coding sequence (SEQ ID NO: 3), the yeast LPAAT coding sequence (SEQ ID NO: 3), E. coli LPAAT coding sequence (SEQ ID NO: 4), and the maize LPAAT coding sequence (SEQ ID NO: 5). This comparison shows that human LPAATα has the greatest extended homology with yeast or E. coli LPAAT than with the plant LPAAT.

FIG. 3 shows the DNA sequence of the cDNA insert pSP.LPAT3 encoding hLPAATβ (SEQ ID NO: 6). The nucleotide sequence analysis and restriction mapping of the cDNA clone revealed a 5' untranslated region of 39 base pairs and an open reading frame encoding a 278 amino acid polypeptide that spans positions 40–876. It also shows a 3' untranslated region of 480 base pairs from pSP.LPAT3. The initiation site for translation was localized at nucleotide positions 40–42 and fulfilled the requirement for an adequate initiation site (Kozak, *Critical Rev. Biochem. Mol. Biol.* 27:385–402, 1992).

FIG. 4 shows the sequence (SEQ ID NOS: 1 and 2) of the hLPAATβ 278 amino acid open reading frame. The amino acid sequence was used as the query sequence to search for homologous sequences in protein databases. Search of the database based on Genbank Release 92 database from the National Center for Biotechnology Information (NCBI) using the blastp program showed that this protein was most homologous to yeast, bacterial and plant LPAATs.

FIG. 6 shows a comparison of LPAAT activity in A549 cells transfected with pCE9.LPAAT1 DNA, or no DNA using a TLC (thin layer chromatography) assay. These data are described in more detail in examples 3 and 4.

FIGS. 7 and 8 show a comparison of the production of TNF (FIG. 7) and IL-6 (FIG. 8) between A549 cells transfected with pCE9.LPAAT1 and control A549 cells after stimulation with IL-1β and murine TNF. These data show A549 overexpressing LPAAT produces>5 fold more TNF and>10 fold more IL-6 relative to untransfected A549 cells, suggesting that over expression of LPAAT enhances the cytokine signaling response in cells.

FIG. 9 shows the DNA and the translated sequence of LPAATγ1 (SEQ ID NOS: 12 and 13).

FIG. 10 shows the DNA and the translated sequence of LPAATγ2 (SEQ ID NOS: 14 and 15).

FIG. 11 shows the DNA and the translated sequence of LPAATδ (SEQ ID NOS: 16 and 17).

FIG. 12 shows the LPAAT amino acid sequence alignment for human LPAAT γ1, γ2, and δ (SEQ ID NOS: 13, 15, and 17 respectively).

DETAILED DESCRIPTION OF THE INVENTION

Figure 5A:
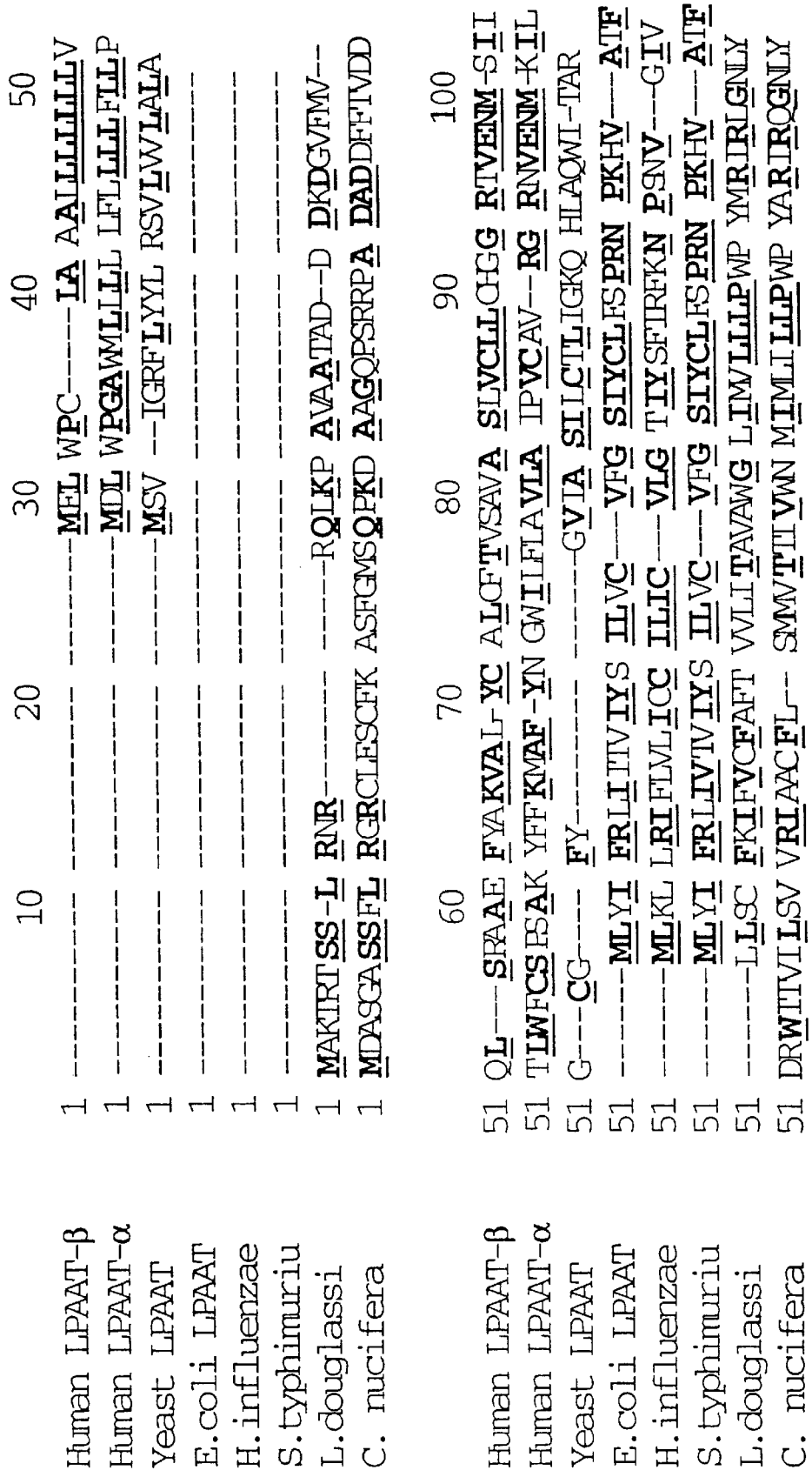
FIG. 5 shows amino acid sequences alignment of human LPAATβ coding sequence (SEQ ID NO: 7), human LPAATα coding sequence (SEQ ID NO: 2), yeast LPAAT coding sequence (SEQ ID NO: 3), bacterial (*E. coli, H. influenzae*, and *S. typhimurium*) LPAAT coding sequences (SEQ ID NOS: 4, 8 and 9), and plant (*L. douglassi* and *C. nucifera*) LPAAT coding sequences (SEQ ID NOS: 10 and 11), revealing that the human LPAAT coding sequences have a much more extended homology with the yeast or the bacterial LPAAT than with the plant LPAAT.

The present invention provides isolated LPAAT polypeptides and isolated polynucleotides encoding LPAAT polypeptides. The term "isolated," in this context, denotes a polypeptide or polynucleotide essentially free of other polypeptides or nucleic acid sequences, respectively, or of other contaminants normally found in nature.

The invention includes biologically active LPAAT and biologically active fragments thereof. As used herein, the term "biologically active" in the context of LPAAT activity refers to the ability to catalyze the acylation of lysophosphatidic acid (LPA) to phosphatidic acid (PA) by acylating the sn-2 position of LPA with a fatty acid acyl-chain moiety.

The term "expression product" as used throughout the specification refers to materials produced by recombinant DNA techniques.

The present invention contemplates modification of the hLPAATα, hLPAATβ, hLPAATγ1, hLPAATγ2, and hLPAATδ polypeptide sequences. Such modifications may be deliberate, as by site-directed mutagenesis, or may be spontaneous. All of the polypeptides produced by these modifications are included herein as long as the acyltransferase activity of LPAAT is present.

For example, the present invention contemplates the deletion of one or more amino acids from the polypeptide sequence of the hLPAATα, hLPAATβ, hLPAATγ1, hLPAATγ2, and hLPAATδ to create deletion variants. This deletion can be of one or more amino or carboxy terminal amino acids or one or more internal amino acids. The present invention further contemplates one or more amino acid substitutions to the polypeptide sequence of hLPAATα, hLPAATβ, hLPAATγ1, hLPAATγ2, and hLPAAT to create subsititutional variants. The present invention contemplates that such substitutional variants would contain certain functional alterations, such as stabilizing against proteolytic cleavage. Yet, it is understood that such variants retain their acyltransferase activity.

Substitutions preferably are conservative, that is, one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The present invention further contemplates the insertion of one or more amino acids to the polypeptide sequences of hLPAATα, hLPAATβ, hLPAATγ1, hLPAATγ2, and hLPAATδ to create an insertional variant. Examples of such insertional variants include fusion proteins such as those used to allow rapid purification of the polypeptide and also can include hybrid polypeptides containing sequences from other proteins and polypeptides which are homologues of the inventive polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptides. These typically are smaller insertions than the fusion proteins described above and are introduced, for example, to disrupt a protease cleavage site.

Polypeptides of the present invention can be synthesized by such commonly used methods as t-BOC or FMOC protection of alpha-amino groups. Both methods involve step-wise syntheses whereby a single amino acid is added at each step starting from the C terminus of the peptide (Coligan et al., Current Protocols in Immunology, Wiley Interscience, Unit 9, 1991). In addition, polypeptide of the present invention can also be synthesized by solid phase synthesis methods (e.g., Merrifield, J. Am. Chem. Soc. 85:2149, 1962; and Steward and Young, Solid Phase Peptide Synthesis, Freeman, San Francisco pp. 27–62, 1969) using copolyol (styrene-divinylbenzene) containing 0.1–1.0 mM amines/g polymer. On completion of chemical synthesis, the polypeptides can be deprotected and cleaved from the polymer by treatment with liquid HF 10% anisole for about 15–60 min at 0° C. After evaporation of the reagents, the peptides are extracted from the polymer with 1% acetic acid solution, which is then lyophilized to yield crude material. This can normally be purified by such techniques as gel filtration of Sephadex G-15 using 5% acetic acid as a solvent. Lyophilization of appropriate fractions of the column will yield a homogeneous polypeptide or polypeptide derivatives, which are characterized by such standard techniques as amino acid analysis, thin layer chromatography, high performance liquid chromatography, ultraviolet absorption spectroscopsy, molar rotation, solubility and quantitated by solid phase Edman degradation.

The invention also provides polynucleotides which encode the hLPAAT polypeptides of the invention. As used herein, "polynucleotide" refers to a polymer of deoxyribonucleotides or ribonucleotides in the form of a separate fragment or as a component of a larger construct.

Polynucleotide sequences of the invention include DNA, RNA and cDNA sequences. Preferably, the polynucleotide sequences encoding hLPAAT are the sequences of: SEQ ID NO. 1 for hLPAATα; SEQ ID NO. 6 for LPAATβ; FIG. 9 for hLPAATγ1; FIG. 10 for hLPAATγ2; and FIG. 11 for hLPAATδ. DNA sequences of the present invention can be obtained by several methods. For example, the DNA can be isolated using hybridization procedures which are known in the art. Such hybridization procedures include, for example, hybridization of probes to genomic or cDNA libraries to detect shared nucleotide sequences, antibody screening of expression libraries to detect shared structural features, such as a common antigenic epitope, and synthesis by the polymerase chain reaction (PCR).

Hybridization procedures are useful for screening of recombinant clones by using labeled mixed synthetic oligonucleotide probes, wherein each probe is potentially the complete complement of a specific DNA sequence in a hybridization sample which includes a heterogeneous mixture of denatured double-stranded DNA. For such screening, hybridization is preferably performed on either single-stranded DNA or denatured double-stranded DNA. Hybridization is particularly useful for detection of cDNA clones derived from sources where an extremely low amount of mRNA sequences relating to the polypeptide of interest are present. Using stringent hybridization conditions directed to avoid non-specific binding, it is possible to allow an autoradiographic visualization of a specific cDNA clone by the hybridization of the target DNA to that single probe in the mixture, which is its complement (Wallace et al. Nucl. Acid Res. 9:879, 1981). Stringent conditions preferably include high stringency conditions. See, for example, Maniatis et al, Molecular Cloning (A Laboratory Manual), Cold Spring Harbor Laboratory, pages 387–389, 1982. One such high stringency hybridization condition is, for example, 4×SSC at 65° C., followed by washing in 0.1×SSC at 65° C. for thirty minutes. Alternatively, another high stringency hybridization condition is in 50% formamide, 4×SSC at 42° C.

The development of specific DNA sequences encoding hLPAAT can also be obtained by isolation of double-stranded DNA sequences from the genomic DNA, chemical manufacture of a DNA sequence to provide the necessary codons for the polypeptide of interest, and in vitro synthesis of a double-stranded DNA sequence by reverse transcription of mRNA isolated for a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently a method that is preferred when the entire sequence of amino acids residues of the desired polypeptide product is known. When the entire sequence of amino acid residues of the desired polypeptide is not known, direct synthesis of DNA sequences is not possible and it is desirable to synthesize cDNA sequences. cDNA sequence isolation can be done, for example, by formation of plasmid- or phage-carrying cDNA libraries which are derived from reverse transcription of mRNA. mRNA is abundant in donor cells that have high levels of genetic expression. In the event of lower levels of expression, PCR techniques are preferred. When a significant portion of the amino acid sequence is known, production of labeled single or double stranded DNA or RNA probe sequences duplicating a sequence putatively present in the target cDNA may be employed in DNA/DNA hybridization procedures, carried out on cloned copies of the cDNA (denatured into a single-stranded form) (Jay et al., *Nucl. Acid Res.* 11:2325, 1983).

A cDNA expression library, such as lambda gt11, can be screened for hLPAATα, hLPAATβ, hLPAATγ1, hLPAATγ2, and hLPAATδ polypeptides using antibodies specific for hLPAATα, hLPAATβ, hLPAATγ1, hLPAATγ2, and hLPAATδ. Such antibodies can be either polyclonally or monoclonally derived.

The polynucleotides of this invention include sequences that are degenerate as a result of the genetic code. The genetic code is described as degenerate because more than one nucleotide triplet, called a codon, can code for a single amino acid. The present invention contemplates the degeneracy of the genetic code and includes all degenerate nucleotide sequences which encode hLPAATα, hLPAATβ, hLPAATγ1, hLPAATγ2, and hLPAATδ.

The present invention also includes polynucleotide sequences complementary to the polynucleotides encoding hLPAATα, hLPAATβ, hLPAATγ1, hLPAATγ2, and hLPAATδ. Specifically, the present invention includes antisense polynucleotides. An antisense polynucleotide is a DNA or RNA molecule complementary to at least a portion of a specific mRNA molecule (Weintraub, *Sci. Amer.* 262:40, 1990). The invention embraces all antisense polynucleotides capable of inhibiting the expression of hLPAATα, hLPAATβ, hLPAATγ1, hLPAATγ2, or hLPAATδ. In a cell, the antisense polynucleotides hybridize to the corresponding mRNA, forming a double-stranded molecule. The antisense polynucleotides interfere with the translation of mRNA since the cell cannot translate mRNA that is double-stranded. Antisense oligomers of about 15 nucleotides are preferred, since they are easily synthesized and are less likely to cause problems than larger molecules when introduced into the target of hLPAATα, hLPAATPβ, hLPAATγ1, hLPAATγ2, or hLPAATδ-producing cell. The use of antisense methods to inhibit translation of genes is known (e.g., Marcus-Sakura, *Anal. Biochem.* 172:289, 1988).

The present invention further includes allelic variations, i.e., naturally-occurring base changes in a species population which may or may not result in an amino acid change, to the polynucleotide sequences encoding hLPAATα, hLPAATPβ, hLPAATγ1, hLPAATγ2, or hLPAATδ. The inventive polynucleotide sequences further comprise those sequences which hybridize under high stringency conditions (see, for example, Maniatis et al, *Molecular Cloning (A Laboratory Manual)*, Cold Spring Harbor Laboratory, pages 387–389, 1982) to the coding regions or to the complement of the coding regions of hLPAATα, hLPAATβ, hLPAATγ1, hLPAATγ2, or hLPAATδ. One such high stringency hybridization condition is, for example, 4×SSC at 65° C., followed by washing in 0.1×SSC at 65° C. for thirty minutes. Alternatively, another high stringency hybridization condition is in 50% formamide, 4×SSC at 42° C.

In addition, ribozyme nucleotide sequences that cleave hLPAATα, hLPAATβ, hLPAATγ1, hLPAATγ2, and hLPAATδ are included in this invention. Ribozymes are RNA molecules possessing an ability to specifically cleave other single-stranded RNA in a manner analogous to DNA restriction endonucleases. Through the modification of nucleotide sequences which transcribe such RNAs, it is possible to engineer molecules that recognize specific nucleotide sequences in an RNA molecule and cleave it (Cech, *J. Amer. Med. Assn.* 260:3030, 1988).

There are two basic types of ribozymes, tetrahymena-type (Hasselhoff, *Nature* 334:585, 1988) and "hammerhead-type". Tetrahymena-type ribozymes recognize sequences which are four bases in length, while "hammerhead-type" ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species.

Production of Polypeptides

Polynucleotide sequences encoding hLPAATα, hLPAATβ, hLPAATγ1, hLPAATγ2, and hLPAATδ polypeptides of the invention can be expressed in either prokaryotes or eukaryotes. Hosts can include microbial (bacterial), yeast, insect and mammalian organisms. Methods of expressing DNA sequences inserted downstream of prokaryotic or viral regulatory sequences in prokaryotes are known in the art (Makrides, *Microbio. Rev.* 60:512, 1996). Biologically functional viral and plasmid DNA vectors capable of expression and replication in a eukaryotic host are known in the art (Cachianes, *Biotechniques* 15:255, 1993). Such vectors are used to incorporate DNA sequences of the invention. DNA sequences encoding the inventive polypeptides can be expressed in vitro by DNA transfer into a suitable host using known methods of transfection.

hLPAATα, hLPAATβ, hLPAATγ1, hLPAATγ2, and hLPAATδ sequences may be inserted into a recombinant expression vector. The term "recombinant expression vector" refers to a plasmid, virus or other vehicle that has been manipulated by inserting or incorporating genetic sequences. Such expression vectors contain a promoter sequence which facilitates efficient transcription of the inserted genetic sequence of the host. The expression vector typically contains an origin of replication and a promoter, as well as specific genes which allow phenotypic selection of the transformed cells. The DNA segment can be present in the vector, operably linked to regulatory elements, for example, a promoter (e.g., T7, metallothionein I, or polyhedren promoters). Vectors suitable for use in the present invention include, for example, bacterial expression vectors, with bacterial promoter and ribosome binding sites, for expression in bacteria (Gold, *Meth. Enzymol.* 185:11, 1990), expression vector with animal promoter and enhancer for expression in mammalian cells (Kaufman, *Meth. Enzymol.* 185:487, 1990) and baculovirus-derived vectors for expression in insect cells (Luckow et al., *J. Virol.*67:4566, 1993).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoriboseyltransferase (XGPRT, gpt).

In another preferred embodiment, the expression system used is one driven by the baculovirus polyhedrin promoter. The polynucleotide encoding LPAAT can be manipulated by standard techniques in order to facilitate cloning into the baculovirus vector. See Ausubel et al., supra. A preferred baculovirus vector is the pBlueBac vector (Invitrogen, Sorrento, Calif.). The vector carrying a polynucleotide encoding LPAAT is transfected into *Spodoptera frugiperda* (Sf9) cells by standard protocols, and the cells are cultured and processed to produce the recombinant polypeptide. See Summers et al., A Manual for Methods of Baculovirus Vectors and Insect Cell Culture Procedures, Texas Agricultural Experimental Station.

The polynucleotides of the present invention can be expressed in any number of different recombinant DNA expression systems to generate large amounts of polypeptide. Included within the present invention are LPAAT polypeptides having native glycosylation sequences, and deglycosylated or unglycosylated polypeptides prepared by the methods described below. Examples of expression systems known to the skilled practitioner in the art include bacteria such as *E. coli*, yeast such as *Pichia pastoris*, baculovirus, and mammalian expression systems such as in Cos or CHO cells.

The polynucleotides of the present invention can be inserted into an expression vector by standard subcloning techniques. In a preferred embodiment, an *E. coli* expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the thiofusion system (Invitrogen, San Diego, Calif.), the Strep-tag II system (Genosys, Woodlands, Tex.), the FLAG system (IBI, New Haven, Conn.), and the 6×His system (Qiagen, Chatsworth, Calif.). Some of these systems produce recombinant polypeptides bearing only a small number of additional amino acids, which are unlikely to affect the LPAAT ability of the recombinant polypeptide. For example, both the FLAG system and the 6×His system add only short sequences, both of which are known to be poorly antigenic and which do not adversely affect folding of the polypeptide to its native conformation. Other fusion systems produce proteins where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.) or enterokinase (Invitrogen, San Diego, Calif.).

In an embodiment of the present invention, the polynucleotides encoding LPAAT are analyzed to detect putative transmembrane sequences. Such sequences are typically very hydrophobic and are readily detected by the use of standard sequence analysis software, such as MacDNASIS (Hitachi, San Bruno, Calif.). The presence of transmembrane sequences is often deleterious when a recombinant protein is synthesized in many expression systems, especially in *E. coli*, as it leads to the production of insoluble aggregates which are difficult to renature into the native conformation of the polypeptide.

Accordingly, deletion of one or more of the transmembrane sequences may be desirable. Deletion of transmembrane sequences typically does not significantly alter the conformation or activity of the remaining polypeptide structure. However, one can determine whether deletion of one or more of the transmembrane sequences has effected the biological activity of the LPAAT protein by, for example, assaying the activity of the LPAAT protein containing one or more deleted sequences and comparing this activity to that of unmodified LPAAT. Assaying LPAAT activity can be accomplished by, for example, contacting the LPAAT protein of interest with the substrates LPA and fatty acyl-CoA and measuring the generation of PA or CoA, or, alternatively, measuring the formation of free CoA. Such assays for determining LPAAT activity are described in more detail below in the section describing screening assays.

Moreover, transmembrane sequences, being by definition embedded within a membrane, are inaccessible as antigenic determinants to a host immune system. Antibodies to these sequences will not, therefore, provide immunity to the host and, hence, little is lost in terms of generating monoclonal or polyclonal antibodies by omitting such sequences from the recombinant polypeptides of the invention. Deletion of transmembrane-encoding sequences from the polynucleotide used for expression can be achieved by standard techniques. See Ausubel et al., supra, Chapter 8. For example, fortuitously-placed restriction enzyme sites can be used to excise the desired gene fragment, or the PCR can be used to amplify only the desired part of the gene.

Transformation of a host cell with recombinant DNA may be carried out by conventional techniques. When the host is prokaryotic, such as *E. coli*, competent cells which are capable of DNA uptake can be prepared from cells harvested after exponential growth phases and subsequently treated by a $CaCl_2$ method using standard procedures. Alternatively, $MgCl_2$ or RbCl can be used. Transformation can also be performed after forming a protoplast of the host cell or by electroporation.

When the host is a eukaryote, methods of transfection of DNA, such as calcium phosphate co-precipitates, conventional mechanical procedures, (e.g., microinjection), electroporation, liposome-encased plasmids, or virus vectors may be used. Eukaryotic cells can also be cotransformed with DNA sequences encoding hLPAATα, hLPAATβ, hLPAATγ1, hLPAATγ2, and hLPAATδ polypeptides of the invention, and a second foreign DNA molecule encoding a selectable phenotype, such as the herpes simplex thymidine kinase gene. Another method uses a eukaryotic viral vector, such as simian virus 40 (SV40) or bovine papilloma virus to transiently infect or transform eukaryotic cells and express the hLPAATα, hLPAATβ, hLPAATγ1, hLPAATγ2, and hLPAATδ polypeptides.

Expression vectors that are suitable for production of LPAAT polypeptides preferably contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. LPAAT polypeptides of the present invention preferably are expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273,1982); the TK promoter of Herpes virus (McKnight, *Cell* 31: 355, 1982); the SV40 early promoter (Benoist et al., *Nature* 290:304, 1981); the Rous sarcoma virus promoter (Gonnan et al., *Proc. Nat'l. Acad. Sci. USA* 79:6777, 1982); and the cytomegalovirus promoter (Foecking et al., *Gene* 45:101, 1980). Alternatively, a prokaryotic promoter, such as the bacteriophage T3 RNA polymerase promoter, can be used to control fusion gene expression if the prokaryotic promoter is regulated by a eukaryotic promoter (Zhou et al., *Mol. Cell. Biol.* 10:4529, 1990; Kaufman et al., *Nucl. Acids Res.* 19:4485, 1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), *Gene Transfer and Expression Protocols* (Humana Press 1991). Examples of mammalian host cells include COS, BHK, 293 and CHO cells.

Purification of Recombinant Polypeptides

The LPAAT polypeptide expressed in any of a number of different recombinant DNA expression systems can be obtained in large amounts and tested for biological activity. The recombinant bacterial cells, for example *E. coli*, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8 M) or chaotropic agents such as guanidine hydrochloride in the presence of reducing agents such as β-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, biologically active hLPAATα, hLPAATβ, hLPAATγ1, hLPAATγ2, and hLPAATδ useful for screening compounds for, e.g., trilineage hematopoietic and anti-inflammatory therapeutic applications, and developing antibodies for therapeutic, diagnostic and research use.

Screening Assays

The hLPAATα, hLPAATβ, hLPAATγ1, hLPAATγ2, and hLPAATδ polypeptides of the present invention are also useful in a screening methodology for identifying compounds or compositions which affect cellular signaling of an inflammatory response. Such compounds or compositions to be tested can be selected from a combinatorial chemical library or any other suitable source (Hogan, Jr., *Nat. Biotechnology* 15:328, 1997).

This method comprises, for example, contacting hLPAATα, hLPAATβ, hLPAATγ1, hLPAATγ2, and/or hLPAATδ in the presence of compound and substrate for LPAAT, namely LPA and fatty acyl-CoA. These hLPAAT proteins can either be purified prior to incubation or can be contained in extracts from a cell line or cell lines (for example, Sf9, ECV304, A549) transfected with cDNA encoding these polypeptides (West et al., *DNA Cell Biol.* 16:691, 1997). Alternatively, hLPAAT protein can be purified from transfected cells, and the protein, being a transmembrane protein, can then be reconstituted in a lipid bilayer to form liposomes for delivery into cells (Weiner, *Immunomethods* 4:201, 1994).

The effect of a compound or composition on hLPAATα, hLPAATβ, hLPAATγ1, hLPAATγ2, or hLPAATδ activity can be determined, for example, by measuring the generation of PA and CoA. PA can be measured by, for example, TLC methods described in Examples 3 and 7, found below. Alternatively, LPAAT activity can be assayed by detecting the formation of free CoA in reaction. CoA, which contains a free sulfhydryl-group, can be measured either by, for example, colorimetric or fluorescenic methods with sulfhydryl-specific reagents, such as, 5,5'-dithiobis-(2-nitrobenzoic acid) (DTNB) or ThioGlo (Covalent Associates, Woburn, Mass.). The observed effect on hLPAATα, hLPAATβ, hLPAATγ1, hLPAATγ2, and hLPAATδ may be either inhibitory or stimulatory.

Peptide Sequencing

Purified polypeptides prepared by the methods described above can be sequenced using methods well known in the art, for example using a gas phase peptide sequencer (Applied Biosystems, Foster City, Calif.). Because the proteins of the present invention may be glycosylated, it is preferred that the carbohydrate groups are removed from the proteins prior to sequencing. This can be achieved by using glycosidase enzymes. Preferably, glycosidase F (Boehringer-Mannheim, Indianapolis, Ind.) is used. To determine as much of the polypeptide sequence as possible, it is preferred that the polypeptides of the present invention be cleaved into smaller fragments more suitable for gas-phase sequence analysis. This can be achieved by treatment of the polypeptides with selective peptidases, and in a particularly preferred embodiment, with endoproteinase lys-C (Boehringer). The fragments so produced can be separated by reversed-phase HPLC chromatography.

Antibodies Directed to LPAAT

Antibodies to human LPAAT can be obtained using the product of an LPAAT expression vector or synthetic peptides derived from the LPAAT coding sequence coupled to a carrier (Pasnett et al., *J. Biol. Chem.* 263:1728, 1988) as an antigen. The preparation of polyclonal antibodies is well-known to those of skill in the art. See, for example, Green et al., "Production of Polyclonal Antisera," in *Immunochemical Protocols* (Manson, ed.), pages 1–5 (Humana Press 1992). Alternatively, an LPAAT antibody of the present invention may be derived from a rodent monoclonal antibody (MAb). Rodent monoclonal antibodies to specific antigens may be obtained by methods known to those skilled in the art. See, for example, Kohler and Milstein, *Nature* 256:495, 1975, and Coligan et al. (eds.), *Current Protocols in Immunology*, 1:2.5.1–2.6.7 (John Wiley & Sons 1991). Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in *Methods in Molecular Biology*, 10:79–104 Humana Press, Inc. 1992. An LPAAT antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46:310, 1990.

Alternatively, a therapeutically useful LPAAT antibody may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l. Acad. Sci. USA* 86:3833, 1989. Techniques for producing humanized MAbs are described, for example, by Jones et al., *Nature* 321:522, 1986, Riechmann et al., *Nature* 332:323, 1988, Verhoeyen et al., *Science* 239:1534, 1988, Carter et al., *Proc. Nat'l Acad. Sci. USA* 89:4285, 1992, Sandhu, *Crit. Rev. Biotech.* 12: 437, 1992, and Singer et al., *J. Immun.* 150:2844, 1993, each of which is hereby incorporated by reference.

As an alternative, an LPAAT antibody of the present invention may be derived from human antibody fragments isolated from a combinatorial immunoglobulin library. See, for example, Barbas et al., *METHODS: A Companion to Methods in Enzymology* 2:119 1991, and Winter et al., *Ann. Rev. Immunol.* 12:433, 1994, which are incorporated by reference. Cloning and expression vectors that are useful for producing a human immunoglobulin phage library can be obtained, for example, from STRATAGENE Cloning Systems (La Jolla, Calif.). In addition, an LPAAT antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994, and Taylor et al., *Int. Immun.* 6:579, 1994.

hLPAATα and hLPAATβ hLPAATα

Search of the Genbank database of expressed sequence tag (dbest) using either the yeast or plant LPAAT protein sequences as probe came up with several short stretches of cDNA sequences with homology to the yeast or plant LPAAT protein sequence. These cDNA sequences of interest were derived from single-run partial sequencing of random human cDNA clones projects carried out by either the WashU-Merck EST or the Genexpress-Genethon program. An example of the amino acids sequence homology between the yeast LPAAT and a human cDNA clone (dbest #102250) is shown below by comparing SEQ ID NO. 18 (top amino acid sequence) with SEQ ID NO 19 (bottom amino acid sequence):

```
PFKKGAFHLAQQGKIPIVPVVVSNTSTLVSPKYGVFNRGCMIVRILKPISTE
* ****** * **** * *        *  *  *  ** * * **
PSNCGAFHLAVQAQVPIVPIVMSSYQDFYCKKERRFTSGQCQVRVLPPVPTE
```

The top line refers to the yeast LPAAT sequence from amino acids 169 to 220 and the bottom line refers to the homologous region from the dbest clone #102250. Identical amino acids between these two sequences are shown in block letters with asterisks in between Accordingly, a synthetic oligonucleotide (o.BLPAT.2R), 5'-TGCAAGATGGAAGGCGCC-3' (SEQ ID NO. 20), was made based on the complement sequence of the conserved amino acids region, GAFHLA (SEQ ID NO. 21), of clone #102250. o.BPLAT.2R was radiolabeled at its 5'-end using γ-$^{32}$P-ATP and T4 polynucleotide kinase as a probe in screening a λzap human brain cDNA library (Stratagene).

Screening of the cDNA library was accomplished by filter hybridization using standard methods (*Current Protocols in Molecular Biology*, John Wiley & Sons, Inc., 1995). Duplicate filters containing DNA derived from λ phage plagues were prehybridized at 60° C. for 2 hr in 6×SSC (1×SSC is 0.15 M NaCl, 0.015 M sodium citrate, pH 7.0), 5×Denhardt's solution (1×Denhardt's solution is 0.02% Ficoll, 0.02% bovine serum albumin, and 0.02% polyvinylpyrrolidone), 0.1% sodium dodecyl sulfate (SDS), 50 mg/ml sonicated and denatured salmon sperm DNA. Hybridization was carried out in the same buffer as used for prehybridzation. After hybridization, the filters were washed in 6×SSC at 42° C., and autoradiographed.

Of the approximately 1×10$^6$ clones from the human brain cDNA library that were screened, twelve clones were identified that hybridized with the probe in duplicate filters. Eleven out twelve clones were enriched and recovered after a secondary screen. Ten enriched phage samples were then converted to plasmid transformed cells by co-infecting *E. coli* XL1-Blue with the helper phage R408 using Stratagene's recommended procedure. Colony filter hybridization was performed and identified those colonies that "lit up" with the probe. Seven out of the ten pools of colonies contained positive clones. Two out of these seven clones, pZlpat.10 and pZlpat.11, contained inserts>2 kb. Restriction mapping using a combination of Sst I, Pst I and BamHI digests showed these two clones contained many common fragments with respect to each other.

Nucleotide sequencing of the cDNA inserts in pZlpat.10 and pZlpat.11 was performed. FIG. 1 shows the DNA sequence of the cDNA insert of pZplat.11. The nucleotide sequence analysis and restriction mapping of the cDNA clone revealed a 5'-untranslated region of>300 bp, an open reading frame capable of encoding a 283 amino acid polypeptide, and a 3'-untranslated region of>800 bp. The initiation site for translation was localized at nucleotide positions 319–321 and fulfilled the requirement for an adequate initiation site according to Kozak (Kozak, *Critical Rev. Biochem. Mol. Biol.* 27:385–402, 1992). There was another upstream ATG at positions 131–133 with an in-phase stop codon at positions 176–178. Except with a shorter 5'-untranslated region, the cDNA insert of pZplat.10 has the same DNA sequence as that of pZplat.11.

The sequence of the 283 amino acid open reading frame in pZplat.11 was used as the query sequence to search for homologous sequences in protein databases. Search of the database based on Genbank Release 90 from the National Center for Biotechnology Information (NCBI) using the blastp program showed that the protein encoded by pZplat.11 was most homologous to the yeast and bacterial LPAATs. FIG. 2 shows amino acid sequences alignment of the putative human LPAATα coding sequence, the yeast LPAAT coding sequence, the *E. coli* LPAAT coding sequence, and the maize LPAAT coding sequence, revealing that human LPAATα has a much more extended homology with the yeast or the *E. coli* LPAAT than with the plant LPAAT.

hLPAATβ

Search of the Genbank database (Boguski, et al., *Science* 265:1993–1994, 1994) of expressed sequence tag (dbEST) using either the yeast or plant LPAAT protein sequences as probe came up with several short stretches of cDNA sequences with homology to the yeast or plant LPAAT protein sequence. These cDNA sequences of interest were derived from single-run partial sequencing of random human cDNA clones projects carried out mainly by I.M.A.G.E. Consortium [LLNL] cDNA clones program. An example of the amino acids sequence homology between the yeast LPAAT and a human cDNA clone (dbEST #363498) is shown below:

```
        180       190       200       210       220       230
QQGKIPIVPVVVSNTSTLVSPKYGVFNRGCMIVRILKPISTENLTKDKIGEFAEKVRDQM
....::::::: :. :..  ..:   :..: ..:..:..:..:..:: ... ..
VRENVPIVPVVYSSFSSFYNTKKKFFTSGTVTVQVLEAIPTSGLTAADVPALRGTPATGP
        120       70        80        90       100       110
```

The top line refers to the yeast LPAAT sequence from amino acids 171 to 230 (SEQ ID NO. 22) and the bottom line refers to the homologous region from the dbest clone #363498 using the +1 reading frame (SEQ ID NO. 23). Identical and conserved amino acids between these two sequences are shown with double dots and single dot, respectively, in between. In order to find out if such cDNA clones with limited homology to yeast LPAAT sequence indeed encode human LPAATβ sequence, it was necessary to isolate the full-length cDNA clone, insert it into an expression vector, and to test if cells transformed or transfected with the cDNA expression vector produced more LPAAT activity.

Accordingly, two synthetic oligonucleotides, 5'-CCTCAAAGTG TGGATCTATC-3' (o.LPAT3.F) (SEQ ID NO. 24) and 5'-GGAAGAGTAC ACCACGGGGA C-3' (o.LPAT3.R), (SEQ ID NO. 25) were ordered (Life Technologies, Gaithersburg, Md.) based on, respectively, the coding and the complement sequence of clone #363498. o.LPAT3.R was used in combination with a forward vector primer (o.sport.1), 5'-GACTCTAGCC TAGGCTTTTG C-3' (SEQ ID NO. 26) for amplification of the 5'-region, while o.LPAT3.F was used in combination with a reverse vector primer (o.sport.1R), 5'-CTAGCTTATA ATACGACTCA C-3' (SEQ ID NO. 27), for amplification of the 3'-region of potential LPAATβ sequences from a pCMV.SPORT human leukocyte cDNA library (Life Technologies, Gaithersburg, Md.). A 700 bp PCR fragment derived from o.sport.1 and o.LPAT3.R amplification was cut with EcoR I before inserting in between the Sma I and EcoR I of pBluescript(II)SK(−) (Stratagene, LaJolla, Calif.) to generate pLPAT3.5'. A 900 bp PCR fragment derived from o.sport.1R and o.LPAT3.F amplification was cut with Xba I before inserting in between the Sma I and Xba I of pBluescript(II)SK(−) (Stratagene, LaJolla, Calif.) to generate pLPAT3.3'. Nucleotide sequencing analysis of the cDNA inserts from these two plasmids showed they contained overlapping sequences with each other, sequences that matched with the dbEST #363498 as well as extensive homology with the yeast LPAAT amino acids sequence (Nagiec et al., *J. Biol. Chem.* 268:22156–22163, 1993). To assemble the two halves of the cDNA into a full-length clone, the 560 bp Nco I-Nar I fragment from pLPAT3.5' and the 780 bp Nar I-Xba I fragment from pLPAT3.3' were inserted into the Nco I/Xba I vector prepared from pSP−luc+ (Promega, Madison, Wis.) via a three-part ligation to generate pSP.LPAT3.

FIG. 3 shows the DNA sequence ID of the cDNA insert of pSP.LPAT3. The nucleotide sequence analysis and restriction mapping of the cDNA clone revealed a 5'-untranslated region of 39 bp, an open reading frame capable of encoding a 278 amino acids polypeptide that spans nucleotide positions 40 to 876 and a 3'-untranslated region of 480 bp (FIG. 3). The initiation site for translation was localized at nucleotide positions 40–42 and fulfilled the requirement for an adequate initiation site according to Kozak (Kozak, *Critical Rev. Biochem. Mol. Biol.* 27:385–402, 1992).

The sequence of the 278 amino acid open reading frame (FIG. 4) was used as the query sequence to search for homologous sequences in protein databases. Search of the database based on Genbank Release 92 from the National Center for Biotechnology Information (NCBI) using the blastp program showed that this protein was most homologous to the yeast, bacterial and plant LPAATs. FIG. 5 shows amino acid sequences alignment of this putative human LPAATβ coding sequence, human LPAATα coding, the yeast LPAAT coding sequence, the bacterial (*E. coli, H. influenzae,* and *S. typhimurium*) LPAAT coding sequences, and the plant (*L. douglassi* and *C. nucifera*) LPAAT coding sequences, revealing that the human LPAAT coding sequences have a much more extended homology with the yeast or the bacterial LPAAT than with the plant LPAAT.

hLPAATγ1, hLPAATγ2 or hLPAATδ

Described below is the isolation of human LPAAT isoforms hLPAATγ1, hLPAATγ2, or hLPAATδ, which are distinct from hLPAATα and hLPAATPβ.

Search of the Genbank database (Boguski, et al., *Science* 265:1993–1994, 1994) of expressed sequence tag (dbEST) using the maize form-I LPAAT protein (Brown, et al., *Plant Mol. Biol.* 26: 211–223, 1994) sequences as probes resulted in the identification of several short stretches of human cDNA sequences with homology to the maize LPAAT protein sequence. These cDNA sequences of interest were derived from single-run partial sequencing of random human cDNA clones projects carried out mainly by I.M.A.G.E. Consortium [LLNL] cDNA clones program. An example of the amino acids sequence homology between the maize LPAAT and a human cDNA clone (GenBank #T55627) is shown below:

```
150 GLQRLKDFPRPFWLALFVEGTRF 172
    ::.::.:.:  .:. :. :::::
    GLRRLSDYPEYMWFLLYCEGTRF
```

The top line refers to the maize LPAAT sequence from amino acids 150 to 172 (SEQ ID NO: 28) and the bottom line refers to the homologous region from the dbEST clone with GenBank #T55627(SEQ ID NO: 30). Identical and conserved amino acids between these two sequences are shown as double dots and single dots, respectively, in the row in between. In order to determine if these human cDNA clones with homology to maize LPAAT but distinct from human LPAATα or LPAATβ indeed encoded human LPAAT, it was undertaken to isolate the full-length cDNA clone, insert it into an expression vector, and to test if cells transformed or transfected with the cDNA expression vector produced more LPAAT activity.

Accordingly, a synthetic oligonucleotides, 5'-GACTACCCC GAGTACATG TGGTTTCTC-3' (oLPTg__1F) (SEQ ID NO: 30) was ordered (Life Technologies, Gaithersburg, Md.) based on the coding region corresponding to amino acids DYPEYMWFL of clone (SEQ ID NO: 31) GenBank #T55627. oLPTg__1F was used in combination with a reverse vector primer (o.sport.1R), 5'-CTAGCTTATA ATACGACTCA C-3', for (SEQ ID NO: 27) amplification of the 3'-region of potential LPAAT sequences from a pCMV.SPORT human leukocyte cDNA library (Life Technologies, Gaithersburg, Md.). A 1,000 bp PCR fragment derived from o.sport.1R and oLPTg__1F amplification was cut with Xho I before inserting in between the Sma I and Xho I of pBluescript(II)SK(−) (Stratagene, LaJolla, Calif.) to generate the plasmid pLPTγ__3'. Nucleotide sequencing (performed by the Seattle Biomedical Research Institute sequencing service) analysis of the cDNA inserts from plasmid pLPTg__3' showed it contained sequences that matched with the clone GenBank #T55627 as well as extensive homology with the C-terminal end of the maize LPAAT amino acids sequence (Brown, et al., *Plant Mol. Biol.* 26: 211–223, 1994). To isolate the 5'-portion of this putative LPAAT clone, a synthetic oligonucleotide, 5'-CACATGTCCG CCTCGTACTT CTTC-3' (oLPTg__1R) (SEQ ID NO: 32), complementary to a region just downstream of the Bam HI site of the cDNA within generate the plasmid pLPTg__3' was used in combination with a forward vector primer (o.sport.1), 5'-GACTCTAGCC TAGGCTTTTG C-3' for (SEQ ID NO: 26) amplification of the 5'-region from a pCMV.SPORT human leukocyte cDNA library (Life Technologies, Gaithersburg, Md.). The PCR fragments generated were cut with Acc65 I and BamH I before inserting in between the Acc65 I and BamH I of pBluescript(II)SK(−) (Stratagene, LaJolla, Calif.). DNA sequence analysis of two cDNA clones containing, respectively, a 980 bp and a 770 bp Acc65 I-BamH I inserts showed they contained sequences that overlapped with the cDNA insert of pLPTγ__3' as well as extensive homology with the N-terminal end of the maize LPAAT amino acids sequence. The DNA sequence of these two cDNA clones diverged at the 5'-regions, suggesting the presence of two alternatively spliced variants with one variant (pLPγ1__5') containing an additional 62 amino acids at the N-terminus relative to the other one (pLPγ2__5'). To assemble the two halves of each cDNA into full-length clones, the 980 bp Acc65 I-BamH I fragment from pLPγ1__5' or the 770 bp Acc65 I-BamH I fragment from pLPγ2__5' were inserted into the Acc65 I/Xho I vector prepared from pBluescript(II)SK(−) (Stratagene, LaJolla, Calif.) along with the 870 bp Bam HI-Xho I fragment from pLPTγ_3' via a three-part ligation to generate pSK_LPγ1 and pSK_LPγ2, respectively.

FIG. 9 shows the DNA and the translated sequence (LPAAT-γ1) of the cDNA insert of pSK_LPγ1. The nucleotide sequence analysis and restriction mapping of the cDNA clone revealed a 5'-untranslated region of 183 bp with two ATGs and an in-phase stop codon, an open reading frame capable of encoding a 376 amino acids polypeptide that spans nucleotide positions 184 to 1314 and a 3'-untranslated region of 345 bp. The initiation site for translation was localized at nucleotide positions 184–186 and fulfilled the requirement for an adequate initiation site (Kozak, *Critical Rev. Biochem. Mol. Biol.* 27:385–402, 1992).

FIG. 10 shows the DNA and the translated sequence (hLPAATγ2) of the cDNA insert of pSK_LPγ2. The nucleotide sequence analysis and restriction mapping of the cDNA clone revealed a 5'-untranslated region of 232 bp with two upstream ATGs with in-phase stop codons, an open reading frame capable of encoding a 314 amino acids polypeptide that spans nucleotide positions 133 to 1177 and a 3'-untranslated region of 346 bp. The initiation site for translation was localized at nucleotide positions 233–235 and fulfilled the requirement for an adequate initiation site (Kozak, *Critical Rev. Biochem. Mol. Biol.* 27:385–402, 1992).

The sequence of the 376 amino acid open reading frame of hLPAATγ1 (FIG. 9) was used as the query sequence to search for homologous sequences in protein databases. Search of the Genbank database from the National Center for Biotechnology Information (NCBI) using the tblastn program showed that this protein was distinct but homologous to a human EST sequence with GenBank #H18562. Shown below is the amino acid sequences alignment of LPAAT-γ1 with this putative human LPAAT coding sequence (LPAAT-δ):

```
LPAAT-γ1  MGLLAFLKTQFVLHLLVGFVFVVSGLVINFVQLCTLALWPVSKQLY   46
          : :  ::.::. ::.  .::. :::.:: .:: :: :::. :::.
LPAAT-δ   MDLAGLLKSQFLCHLVFCYVFIASGLIINTIQLFTLLLWPINKQLF  340
```

The top line refers to the human LPAAT-γ1 sequence from amino acids 1 to 46 (SEQ ID NO: 33) and the bottom line refers to the homologous region from the dbEST clone with GenBank #H18562 (SEQ ID NO: 34). Identical and conserved amino acids between these two sequences are shown as double dots and single dots, respectively, in the row in between. The cDNA for this putative LPAAT-δ clone (Genome Systems Inc., St. Louis, Mo.) was isolated for further analysis.

FIG. 11 shows the DNA and the translated sequence (LPAAT-δ) of this cDNA insert. Nucleotide sequence analysis and restriction mapping revealed a 5'-untranslated region of 157 bp with an upstream ATG and stop codons in all three reading frames, an open reading frame capable of encoding a 378 amino acids polypeptide that spans nucleotide positions 158 to 1294 and a 3'-untranslated region of 480 bp. The initiation site for translation was localized at nucleotide positions 158–160 and fulfilled the requirement for an adequate initiation site (Kozak, *Critical Rev. Biochem. Mol. Biol.* 27:385–402, 1992).

FIG. 12 shows the LPAAT amino acid sequence alignment from the human isoforms γ1, γ2, and δ. Amino acids identical in at least two sequences are highlighted. LPAAT-γ1 and LPAAT-δ have an overall amino acid match of 54% with respect to each other.

EXAMPLE 1

This example illustrates an experiment to determine if the human LPAATα clone encodes a protein with LPAAT activity, an *E. coli* vector expressing the human LPAATα as a fusion protein with β-galactosidase was transformed into a LPAAT minus strain of *E. coli* to see if it would complement the defect in *E. coli*. Specifically, the 840 bp Bgl II-Nco I fragment, which spans the coding region of human LPAATα from amino acid 68 to beyond the stop codon, derived from pZplat.11 was inserted into a Bgl II/Nco I digested cloning vector pLitmus28 (Evans et al., *BioTechniques* 19:130–135, 1995) to generate the plasmid p28BgN. This plasmid is expected to express the human LPAATα as a fusion protein containing the first 16 amino acids of β-galactosidase and the last 216 residues of the human LPAATα coding sequence using the lac promoter in pLitmus28. This plasmid was transformed into the *E. coli* strain JC201 (obtained from Dr. Jack Coleman, Louisiana State University). JC201 (Coleman, *Mol. Gen. Genet.* 232:295–303, 1992; Nagiec et al., *J. Biol. Chem.* 268:22156–22163, 1993; and Brown et al., *Plant Mol. Biol.* 26:211–223, 1994) is deficient in LPAAT activity due to mutation in the plsC locus. This mutation leads to a temperature-sensitive phenotype that causes JC201 to grow slowly at 37° C., almost not at all at 42° C., and not at all at 44° C. JC201 transformed with p28BgN was able to grow normally at 44° C. when compared to the wild type strain JC200 (plsC⁺), while JC201 transformed with pLitmus28 vector was not able to support growth at 44° C. These data suggest that the putative human LPAATα cDNA isolated here does possess LPAAT activity, as the last 216 amino acids of this cDNA is sufficient to complement the defective LPAAT gene (plsC) in JC201.

EXAMPLE 2

To see if the putative human LPAATβ clone encodes a protein with LPAAT activity, an *E. coli* vector expressing this human LPAATβ as a direct product was transformed into a LPAAT minus strain of *E. coli* to see if it would complement the defect in *E. coli*. Specifically, the 1350 bp Nco I-Xba I fragment from pSP.LPAT3, which spans the entire coding region from amino acid 1 to beyond the stop codon, was inserted into a Nco I/Xba I digested cloning vector pKK388-1 (Clontech, Palo Alto, Calif.) to generate the plasmid pTrc.LPAT3. This plasmid was transformed into the *E. coli* strain JC201 (obtained from Dr. Jack Coleman, Louisiana State University). JC201 (Coleman, *Mol. Gen. Genet.* 232:295–303, 1992) is deficient in LPAAT activity due to mutation in the plsC locus. This mutation leads to a temperature-sensitive phenotype that causes JC201 to grow slowly at 37° C., almost not at all at 42° C., and not at all at 44° C. JC201 transformed with pTrc.LPAT3 was able to grow normally at 44° C. when compared to the wild type strain JC200 (plsC⁺), while JC201 transformed with pKK388-1 vector was not able to support growth at 44° C. These data suggest that the putative human LPAATβ cDNA isolated here does possess LPAAT activity, as the putative protein product of this cDNA is able to complement the defective LPAAT gene (plsC) in JC201.

EXAMPLE 3

This example illustrates a group of experiments to see if overexpression of this human LPAATα would have any effect on mammalian cells. The entire cDNA insert (~2,300 bp) from pZplat.11 was cleaved with Asp718 I and Xho I for insertion into the mammalian expression vector pCE9 to generate pCE9.LPAAT1. pCE9 was derived from pCE2 with two modifications. The 550 bp BstY I fragment within the elongation factor-1a (EF-1a) intron of pCE2 was deleted. The multiple cloning region of pCE2 between the Asp718 I and BamH I site was replaced with the multiple cloning region spanning the Asp718 I and Bgl II sites from pLitmus28. The plasmid pCE2 was derived from pREP7b (Leung, et al., *Proc. Natl. Acad. Sci. USA*, 92: 4813–4817, 1995) with the RSV promoter region replaced by the CMV enhancer and the elongation factor-1a (EF-1a) promoter and intron. The CMV enhancer came from a 380 bp Xba I-Sph I fragment produced by PCR from pCEP4 (Invitrogen, San Diego, Calif.) using the primers 5'-GGCTCTAGAT ATTAATAGTA ATCAATTAC-3' (SEQ ID NO: 35) and 5'-CCTCACGCAT GCACCATGGT AATAGC-3' (SEQ ID NO: 36). The EF-1a promoter and intron (Uetsuki, et al., *J. Biol. Chem.*, 264: 5791–5798, 1989) came from a 1200 bp Sph I-Asp718 I fragment produced by PCR from human genomic DNA using the primers 5'-GGTGCATGCG TGAGGCTCCG GTGC-3' (SEQ ID NO: 37) and 5'-GTAGTTTTCA CGGTACCTGA AATGGAAG-3' (SEQ ID NO: 38). These 2 fragments were ligated into a Xba I/Asp718 I digested vector derived from pREP7b to generate pCE2.

pCE9.LPAAT1 DNA was transfected into several mammalian cell lines, including A549 cells, ECV304 cells (American Type Culture Collection, Rockville, Md.), two human cell line that would produce IL-6 and TNF upon stimulation with IL-1b and murine TNF and 293-EBNA cells (Invitrogen, San Diego, Calif.). pCE9.LPAAT1 was digested with BspH I before electroporating into these cell lines with a Cell-Porator™ (Life Technologies, Gaithersburg, Md.) using conditions described previously (Cachianes, et al., *Biotechniques* 15:255–259, 1993). After adherence of the transfected cells 24 hours later, the cells were grown in the presence of 200 µg/ml Hygromycin B (Hyg) (Calbiochem, La Jolla, Calif.) to select for cells that had incorporated both plasmids. Hyg-resistant clones that expressed LPAAT mRNA at a level more than 20 fold higher relative to untransfected cells based on Northern Blot analysis (Kroczek, et al., *Anal. Biochem.* 184: 90–95, 1990) were selected for further study.

FIG. 6 compares the LPAAT activity in A549 cells and in A549 cells transfected with pCE9.LPAAT1 DNA using a TLC assay. This screening assay for LPAAT activity in cell extracts was based on a fluorecent assay using fluorescent lipid substrates (Ella, et al., *Anal. Biochem.* 218: 136–142, 1994). Instead of using the PC-substrate, BPC (Molecular Probes, Eugene, Oreg.), a synthetic PC that contains an ether linkage at the SN1 position with a fluorescent Bodipy moiety incorporated into the end of the alkyl-chain at the SN1 position, BPC was converted to Bodipy-PA using cabbage phospholipase D (Sigma, St. Louis, Mo.). Bodipy-PA was then converted to Bodipy-LPA using snake venom phospholipase A2. The Bodipy-LPA obtained was purified by preparative TLC for use in the LPAAT assay. The assay was carried out in total cell extracts resuspended in lysis buffer (Ella, et al., *Anal. Biochem.* 218: 136–142, 1994) supplemented with 0.5 mM ATP, 0.3 mM $MgCl_2$, 100 µM oleoyl-CoA and 10 µM Bodipy LPA. The samples were incubated for 30 min before loading onto TLC plates.

Lane 1 refers to Bodipy LPA incubated with buffer only without any cell extract added. Lane 9 refers to BPC treated with cabbage phospholipase D for generating a Bodipy-PA marker. Lanes 2 and 4 refer to Bodipy LPA incubated with control A549 cell extracts with or without lipid A, respectively. Lanes 3 and 5 refer to Bodipy LPA incubated with A549 cell extracts transfected with pCE9.LPAAT1 DNA with or without lipid A, respectively. FIG. 3 shows A549 cells transfected with the LPAAT cDNA (lanes 3 and 5) contain much more LPAAT activity than those of control cells (lanes 2 and 4) as evidenced by the increased conversion of Bodipy-LPA to Bodipy-PA. Addition of lipid A to the cell extracts has little effect on LPAAT activity (lanes 2 vs 4 and 3 vs 5). A549 cell extract also contains a phosphohydrolase activity that converts Bodipy-LPA to Bodipy-monoalkylglycerol (lanes 2 to 5). Interestingly, A549 cells overexpressing LPAAT (lanes 3 and 5) have less of this activity compared to control cells (lanes 2 and 4), suggesting this phosphohydrolase prefers LPA to PA as substrate. There is also an increase of DAG in transfected cells (lanes 3 and 5) compared to control cells (lanes 2 and 4) possibly due to partial conversion of the PA formed to DAG from this endogenous phosphohydrolase.

EXAMPLE 4

To see if the expressed LPAAT cDNA clone described here would also use other glycerol-lipids that contain a free-hydroxyl group at the SN2 position, the cell extracts were incubated with the substrates NBD-lysoPC (lanes 6 and 7) and NBD-monoacylglycerol (MAG) (lanes 10 and 11) to see if there is increased conversion to lysoPC and DAG, respectively. Lane 8 and 12 refer, respectively, to NBD-lysoPC and NBD-MAG incubated with buffer only without any cell extract added. TLC analysis shows little difference in the lipid profile between the transfected and control cells (lanes 7 vs 6, lanes 11 vs 10), suggesting the cloned LPAAT enzyme uses LPA as the preferred substrate. It is likely that the acyltransferases for lysoPC (Fyrst, et al., *Biochem. J.* 306:793–799, 1995) and for MAG (Bhat, et al., *Biochemistry* 34: 11237–11244, 1995) represent different enzymes from the LPAAT described here.

EXAMPLE 5 pCE9.LPAAT1 DNA was transfected into A549 cells (American Type Culture Collection, Rockville, Md.), a human cell line that would produce IL-6 and TNF upon stimulation with IL-1 β and murine TNF. pCE9.LPAAT1 was digested with BspH I before electroporating into A549 cells with a Cell-Porator™ (Life Technologies, Gaithersburg, Md.) using conditions described previously (Cachianes, et al., *Biotechniques* 15:255–259, 1993). After adherence of the transfected cells 24 hours later, the cells were grown in the presence of 200 µg/ml Hygromycin B (Hyg) (Calbiochem, La Jolla, Calif.) to select for cells that had incorporated both plasmids. A Hyg-resistant clone that expressed LPAAT mRNA at a level more than 20 fold higher relative to untransfected A549 cells based on Northern Blot analysis (Kroczek et al., *Anal. Biochem.* 184:90–95, 1990) was selected for further study.

Figure 7:
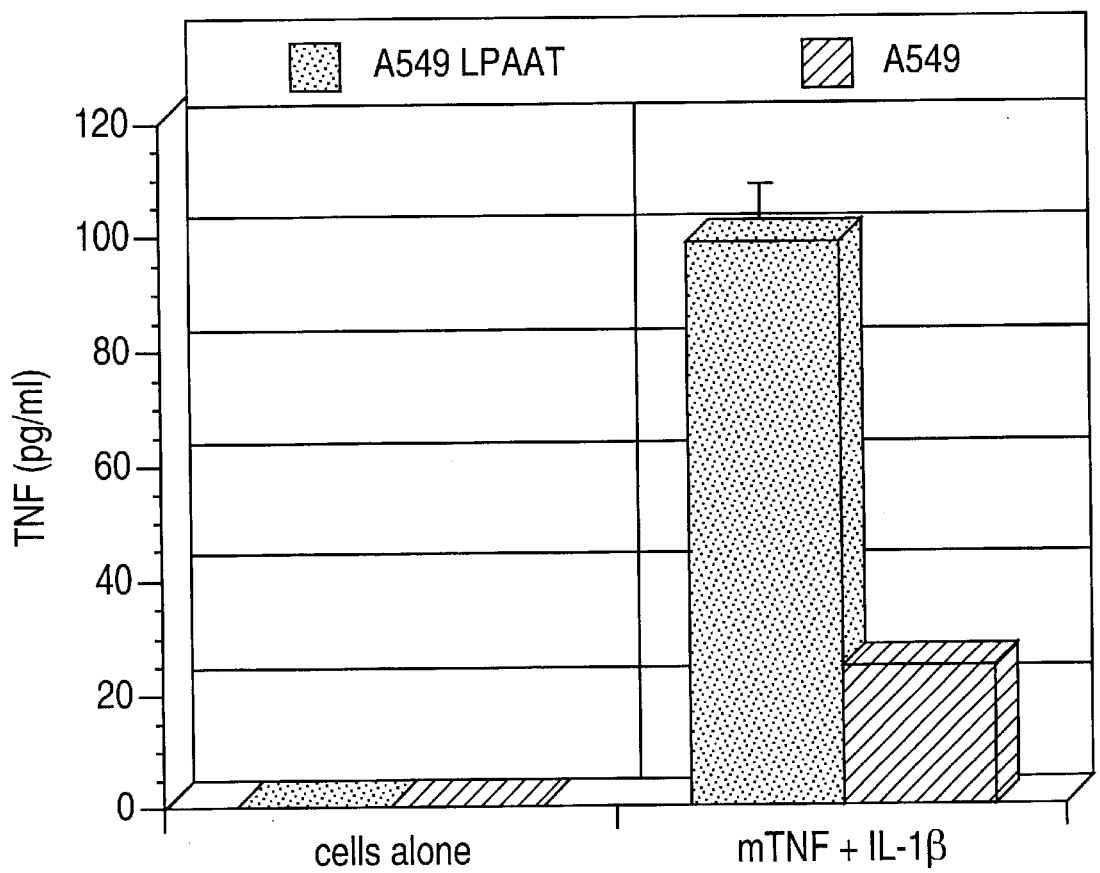

A comparison of the production of TNF (FIG. 7) and IL-6 (FIG. 8) between A549 cells transfected with pCE9.LPAAT1 and control A549 cells after stimulation with IL-1β and murine TNF shows A549 overexpressing LPAAT produces>5 fold more TNF and>10 fold more IL-6 relative to untransfected A549 cells, suggesting that overexpression of LPAAT would enhance the cytokine signaling response in cells. Development of compounds that would modulate LPAAT activity should therefore be of therapeutic interest in the field of inflammation.

EXAMPLE 6

Construction of pC9LPTγ1 and pC2LPTδ: The primers 5'-ggcccggtacc ATGGGCCTG CTGGCCTTC C-3' (oLPγ1_1F) (SEQ ID NO: 39) and 5'-taactcCTCGAG TTATTCCTT TTTCTTAAA CTC-3' (oLPγ1_1R) (SEQ ID NO: 40) were used to amplify the 1100 bp Acc65 I-XhoI fragment by PCR from the template pSK_LPg1. The fragment generated was then inserted into a Acc65 I/Xho I digested pCE9 (West, et al., *DNA Cell Biol.* 6: 691–701, 1997) expression vector to make pC9LPTγ1. Similarly, the primers 5'-atggtggtaccacc ATGGACCTC GCGGGACTG CTG-3' (oLPTδ_1F) (SEQ ID NO: 41) and 5'-GGAgGATATc tAGAgGCCAC CAGTTC-3' (oLPTδ_1R) (SEQ ID NO: 42) were used to amplify the 1100 bp Acc65 I-XBa I fragment by PCR from the template #H18562. The fragment generated was then inserted into a Acc65 I/Nhe I digested pCE2 (West, et al., *DNA Cell Biol.* 6: 691–701, 1997) expression vector to make pC2LPTδ.

EXAMPLE 7

Expression of hLPAATγ1 and hLPAATδ in mammalian cells. Plasmids pC9LPTγ1 or pC2LPTδ were stably transfected into endothelial ECV304 cells (American Type Culture Collection, Rockville, Md.). Specifically, pC9LPTγ1 or pC2LPTδ were digested with BspH I before electroporating into these cell lines with a Cell-Porator™ (Life Technologies, Gaithersburg, Md.). After adherence of the transfected cells 24 hours later, the cells were grown in the presence of 500 μg/ml Hygromycin B (Hyg) (Calbiochem, La Jolla, Calif.) to select for cells that had incorporated plasmids. Hyg-resistant clones that expressed LPAAT-γ1 or LPAAT-δ mRNA at a level more than 10 fold higher than that of cells transfected with pCE9 or pCE2 vector, based on Northern Blot analysis, were selected for further study.

Figure 13:
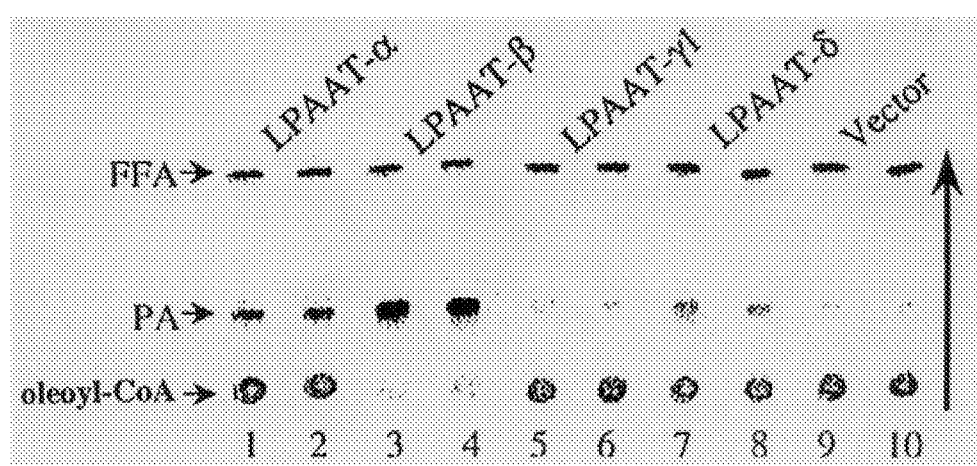
FIG. 13 compares the LPAAT activity in ECV304 cells stably transfected with the expression plasmids for LPAATα (pCE9.LPAAT-α), LPAATβ (pCE9.LPAAT-β) DNA, LPAATγ1 (pC9LPTγγ1), LPAATδ (pC2LPTδ), or the control vector (pCE9).

FIG. 13 compares the LPAAT activity in ECV304 cells stably transfected with the expression plasmids for LPAAT-α (pCE9.LPAAT-α), LPAAT-β (pCE9.LPAAT-β) DNA, LPAAT-γ1 (pC9LPTγ1), LPAAT-δ (pC2LPTδ), or the control vector (pCE9). This screening assay for LPAAT activity in cell extracts was based on the conversion of [$^{14}$C]oleoyl-CoA to [$^{14}$C]PA using a TLC assay. The assay was carried out in total cell extracts resuspended in lysis buffer (Ella, et al., *Anal. Biochem.* 218: 136–142, 1994) supplemented with 50 μM [$^{14}$C]oleoyl-CoA and 200 μM LPA. The samples were incubated for 10 min, extracted from chloroform, before loading onto TLC plates. Lanes 1 and 2 refer to [$^{14}$C]oleoyl-CoA and LPA incubated with cell extract transfected with LPAAT-α plasmid; lanes 3 and 4, with LPAAT-β plasmid; lanes 5 and 6, with LPAAT-γ1 plasmid; lanes 7 and 8, with LPAAT-δ plasmid; and lanes 9 and 10, with control vector. ECV304 cells transfected with LPAAT-α or -β cDNA (lanes 1 to 4) contain more than 3 and 20 times, respectively, LPAAT activity when compared to those of control cells (lanes 9 and 10) as evidenced by the increased conversion of [$^{14}$C]oleoyl-CoA to [$^{14}$C]PA. Cells transfected with LPAAT-δ cDNA (lanes 7 and 8) contain about 2.5 times more LPAAT activity than those of control cells (lanes 9 and 10), whereas cells transfected with LPAAT-δ cDNA show no increase in activity when compared to those of control cells (lanes 9 and 10).

---

We claim:

1. An isolated polynucleotide encoding a polypeptide having Lysophosphatidic Acid Acyltransferase (LPAAT) activity, comprising a nucleotide sequence selected from the group consisting of:
   (a) the DNA sequence (SEQ ID NO: 12, 14 or 16, respectively) of FIG. 9, FIG. 10, or FIG. 11; and
   (b) a polynucleotide sequence which encodes the polypeptide (SEQ ID NO: 13, 15 or 17, respectively) of FIG. 9, FIG. 10, or FIG. 11 and enzymatically active fragments thereof.

2. A method of expressing a polypeptide encoded by the DNA sequence of claim 1, comprising:
   (a) introducing into a cell a polynucleotide comprising a nucleotide sequence selected from the group consisting of:
      (i) the DNA sequence (SEQ ID NO: 12, 14 or 16, respectively) of FIG. 9, FIG. 10, or FIG. 11; and
      (ii) a polynucleotide sequence which encodes the polypeptide (SEQ ID NO: 13, 15 or 17, respectively) of FIG. 9, FIG. 10, or FIG. 11 and enzymatically active fragments thereof,
   wherein said polynucleotide is operably linked to a promoter; and
   (b) maintaining or growing said cell under conditions that result in the expression of said polypeptide.

3. The isolated polynucleotide of claim 1, wherein said polynucleotide comprises the DNA sequence (SEQ ID NO: 12) of FIG. 9 or a DNA sequence encoding the polypeptide (SEQ ID NO: 13) of FIG. 9.

4. The isolated polynucleotide of claim 1, wherein said polynucleotide comprises the DNA sequence (SEQ ID NO: 14) of FIG. 10 or a DNA sequence encoding the polypeptide (SEQ ID NO: 15) of FIG. 10.

5. The isolated polynucleotide of claim 1, wherein said polynucleotide comprises the DNA sequence (SEQ ID NO: 16) of FIG. 11 or a DNA sequence encoding the polypeptide (SEQ ID NO: 17) of FIG. 11.

6. An isolated polynucleotide encoding a polypeptide having Lysophosphatidic Acid Acyltransferase (LPAAT) activity, comprising a DNA sequence capable of hybridizing under high stringency conditions to the complement of (a) or (b) of claim 1 and which encodes a polypeptide having LPAAT activity, wherein the high stringency conditions are characterized by an ionic strength equivalent to 4×SSC at a temperature of 65° C.

7. A method of expressing a polypeptide having LPAAT activity, comprising:

(a) introducing into a cell the isolated polynucleotide of claim 12, 16, or 18.

8. An isolated polynucleotide encoding a polypeptide having Lysophosphatidic Acid Acyltransferase (LPAAT) activity, comprising a nucleotide sequence selected from the group consisting of:

(a) the polynucleotide sequence (SEQ ID NO: 12, 14 or 16, respectively) of FIG. 9, FIG. 10, or FIG. 11 which encode polypeptides able to catalyze acylation of lysophosphatidic acid (LPA) to phosphatidic acid (PA); and (b) a polynucleotide sequence which encodes the polypeptide (SEQ ID NO: 13, 15 or 17, respectively) of FIG. 9, FIG. 10, or FIG. 11.

9. An isolated polynucleotide encoding a polypeptide having Lysophosphatidic Acid Acyltransferase (LPAAT) activity, comprising a DNA sequence capable of hybridizing under high stringency conditions to the complement of (a) or (b) of claim 1 and which encodes a polypeptide having LPAAT activity, wherein the high stringency conditions are characterized by an ionic strength equivalent to 4×SSC at a temperature of 42° C. in the presence of 50% formamide.

10. An isolated polynucleotide encoding a polypeptide having Lysophosphatidic Acid Acyltransferase (LPAAT) activity, comprising a DNA sequence capable of hybridizing under high stringency conditions to the complement of (a) or (b) of claim 1 and which encodes a polypeptide having LPAAT activity, wherein the high stringency conditions are characterized by an ionic strength equivalent to 6×SSC at a temperature of 60° C.

* * * * *

SEQUENCE LISTING

<160> NUMBER OF SEQ ID NOS: 42

<210> SEQ ID NO 1
<211> LENGTH: 2242
<212> TYPE: DNA
<213> ORGANISM: Homo sapiens
<220> FEATURE:
<221> NAME/KEY: CDS
<222> LOCATION: (319)..(1167)

<400> SEQUENCE: 1

```
ggaagtcagc aggcgttggg gaggggtggc gggggaatag cggcggcagc agccccagcc      60
ctcagagaga cagcagaaag ggagggaggg agggtgctgg ggggacagcc ccccaccatt     120
cctaccgcta tgggcccaac ctcccactcc cacctcccct ccatcggccg gggctaggac     180 accccaaat cccgtcgccc ccttggcacc gacaccccga cagagacaga gacacagcca     240
tccgccacca ccgctgccgc agcctggctg gggagggggc cagcccccca ggccccctac     300
ccctctgagg tggccagaa atg gat ttg tgg cca ggg gca tgg atg ctg ctg      351
                     Met Asp Leu Trp Pro Gly Ala Trp Met Leu Leu
                      1               5                  10 ctg ctg ctc ttc ctg ctg ctc ttc ctg ctg ccc acc ctg tgg ttc           399
Leu Leu Leu Phe Leu Leu Leu Leu Phe Leu Leu Pro Thr Leu Trp Phe
             15                  20                  25 tgc agc ccc agt gcc aag tac ttc ttc aag atg gcc ttc tac aat ggc       447
Cys Ser Pro Ser Ala Lys Tyr Phe Phe Lys Met Ala Phe Tyr Asn Gly
         30                  35                  40 tgg atc ctc ttc ctg gct gtg ctc gcc atc cct gtg tgt gcc gtg cga       495
Trp Ile Leu Phe Leu Ala Val Leu Ala Ile Pro Val Cys Ala Val Arg
```

```
                 45                     50                      55
gga cgc aac gtc gag aac atg aag atc ttg cgt cta atg ctg ctc cac         543
Gly Arg Asn Val Glu Asn Met Lys Ile Leu Arg Leu Met Leu Leu His
 60                     65                      70                  75 atc aaa tac ctg tac ggg atc cga gtg gag gtg cga ggg gct cac cac         591
Ile Lys Tyr Leu Tyr Gly Ile Arg Val Glu Val Arg Gly Ala His His
                 80                      85                      90 ttc cct ccc tcg cag ccc tat gtt gtt gtc tcc aac cac cag agc tct         639
Phe Pro Pro Ser Gln Pro Tyr Val Val Val Ser Asn His Gln Ser Ser
                     95                     100                     105 ctc gat ctg ctt ggg atg atg gag gta ctg cca ggc cgc tgt gtg ccc         687
Leu Asp Leu Leu Gly Met Met Glu Val Leu Pro Gly Arg Cys Val Pro
            110                     115                     120 att gcc aag cgc gag cta ctg tgg gct ggc tct gcc ggg ctg gcc tgc         735
Ile Ala Lys Arg Glu Leu Leu Trp Ala Gly Ser Ala Gly Leu Ala Cys
        125                     130                     135 tgg ctg gca gga gtc atc ttc atc gac cgg aag cgc acg ggg gat gcc         783
Trp Leu Ala Gly Val Ile Phe Ile Asp Arg Lys Arg Thr Gly Asp Ala
140                     145                     150                     155 atc agt gtc atg tct gag gtc gcc cag acc ctg ctc acc cag gac gtg         831
Ile Ser Val Met Ser Glu Val Ala Gln Thr Leu Leu Thr Gln Asp Val
                160                     165                     170 agg gtc tgg gtg ttt cct gag gga acg aga aac cac aat ggc tcc atg         879
Arg Val Trp Val Phe Pro Glu Gly Thr Arg Asn His Asn Gly Ser Met
            175                     180                     185 ctg ccc ttc aaa cgt ggc gcc ttc cat ctt gca gtg cag gcc cag gtt         927
Leu Pro Phe Lys Arg Gly Ala Phe His Leu Ala Val Gln Ala Gln Val
        190                     195                     200 ccc att gtc ccc ata gtc atg tcc tcc tac caa gac ttc tac tgc aag         975
Pro Ile Val Pro Ile Val Met Ser Ser Tyr Gln Asp Phe Tyr Cys Lys
    205                     210                     215 aag gag cgt cgc ttc acc tcg gga caa tgt cag gtg cgg gtg ctg ccc        1023
Lys Glu Arg Arg Phe Thr Ser Gly Gln Cys Gln Val Arg Val Leu Pro
220                     225                     230                     235 cca gtg ccc acg gaa ggg ctg aca cca gat gac gtc cca gct ctg gct        1071
Pro Val Pro Thr Glu Gly Leu Thr Pro Asp Asp Val Pro Ala Leu Ala
                240                     245                     250 gac aga gtc cgg cac tcc atg ctc act gtt ttc cgg gaa atc tcc act        1119
Asp Arg Val Arg His Ser Met Leu Thr Val Phe Arg Glu Ile Ser Thr
            255                     260                     265 gat ggc cgg ggt ggt ggt gac tat ctg aag aag cct ggg ggc ggt ggg        1167
Asp Gly Arg Gly Gly Gly Asp Tyr Leu Lys Lys Pro Gly Gly Gly Gly
        270                     275                     280 tgaaccctgg ctctgagctc tcctcccatc tgtccccatc ttcctcccca cacctaccca      1227
cccagtgggc cctgaagcag ggccaaaccc tcttccttgt ctccctctc cccacttatt       1287 ctcctctttg gaatcttcaa cttctgaagt gaatgtggat acagcgccac tcctgccccc      1347
tcttggcccc atccatggac tcttgcctcg gtgcagtttc cactcttgac ccccacctcc     1407
tactgtcttg tctgtgggac agttgcctcc ccctcatctc cagtgactca gcctacacaa     1467
gggaggggaa cattccatcc ccagtggagt ctcttcctat gtggtcttct ctaccctct       1527 accccacat tggccagtgg actcatccat tcttggaac aaatccccc ccactccaaa         1587 gtccatggat tcaatggact catccatttg tgaggaggac ttctcgccct ctggctggaa     1647
gctgatacct gaagcactcc caggctcatc ctgggagctt tcctcagcac cttcaccttc     1707
cctcccagtg tagcctcctg tcagtggggg ctggaccctt ctaattcaga ggtctcatgc     1767
ctgcccttgc ccagatgccc agggtcgtgc actctctggg ataccagttc agtctccaca    1827
```

-continued

```
tttctggttt tctgtcccca tagtacagtt cttcagtgga catgacccca cccagccccc    1887
tgcagccctg ctgaccatct caccagacac aagggaaga agcagacatc aggtgctgca    1947
ctcacttctg ccccctgggg agttggggaa aggaacgaac cctggctgga ggggatagga    2007
gggcttttaa tttatttctt tttctgttga ggcttccccc tctctgagcc agttttcatt    2067
tcttcctggt ggcattagcc actccctgcc tctcactcca gacctgttcc cacaactggg    2127
gaggtaggct gggagcaaaa ggagagggtg ggacccagtt ttgcgtggtt ggttttattt    2187
aattatctgg ataacagcaa aaaaactgaa ataaagaga gagagaaaaa aaaaa         2242
```

<210> SEQ ID NO 2
<211> LENGTH: 283
<212> TYPE: PRT
<213> ORGANISM: Homo sapiens

<400> SEQUENCE: 2

```
Met Asp Leu Trp Pro Gly Ala Trp Met Leu Leu Leu Leu Phe Leu
 1               5                  10                  15

Leu Leu Leu Phe Leu Leu Pro Thr Leu Trp Phe Cys Ser Pro Ser Ala
                20                  25                  30

Lys Tyr Phe Phe Lys Met Ala Phe Tyr Asn Gly Trp Ile Leu Phe Leu
            35                  40                  45

Ala Val Leu Ala Ile Pro Val Cys Ala Val Arg Gly Arg Asn Val Glu
        50                  55                  60

Asn Met Lys Ile Leu Arg Leu Met Leu Leu His Ile Lys Tyr Leu Tyr
65                  70                  75                  80

Gly Ile Arg Val Glu Val Arg Gly Ala His His Phe Pro Pro Ser Gln
                85                  90                  95

Pro Tyr Val Val Val Ser Asn His Gln Ser Ser Leu Asp Leu Leu Gly
            100                 105                 110

Met Met Glu Val Leu Pro Gly Arg Cys Val Pro Ile Ala Lys Arg Glu
        115                 120                 125

Leu Leu Trp Ala Gly Ser Ala Gly Leu Ala Cys Trp Leu Ala Gly Val
    130                 135                 140

Ile Phe Ile Asp Arg Lys Arg Thr Gly Asp Ala Ile Ser Val Met Ser
145                 150                 155                 160

Glu Val Ala Gln Thr Leu Leu Thr Gln Asp Val Arg Val Trp Val Phe
                165                 170                 175

Pro Glu Gly Thr Arg Asn His Asn Gly Ser Met Leu Pro Phe Lys Arg
            180                 185                 190

Gly Ala Phe His Leu Ala Val Gln Ala Gln Val Pro Ile Val Pro Ile
        195                 200                 205

Val Met Ser Ser Tyr Gln Asp Phe Tyr Cys Lys Lys Glu Arg Arg Phe
    210                 215                 220

Thr Ser Gly Gln Cys Gln Val Arg Val Leu Pro Pro Val Pro Thr Glu
225                 230                 235                 240

Gly Leu Thr Pro Asp Asp Val Pro Ala Leu Ala Asp Arg Val Arg His
                245                 250                 255

Ser Met Leu Thr Val Phe Arg Glu Ile Ser Thr Asp Gly Arg Gly Gly
            260                 265                 270

Gly Asp Tyr Leu Lys Lys Pro Gly Gly Gly Gly
        275                 280
```

<210> SEQ ID NO 3

<211> LENGTH: 303
<212> TYPE: PRT
<213> ORGANISM: Yeast

<400> SEQUENCE: 3

```
Met Ser Val Ile Gly Arg Phe Leu Tyr Tyr Leu Arg Ser Val Leu Val
  1               5                  10                  15

Val Leu Ala Leu Ala Gly Cys Gly Phe Tyr Gly Val Ile Ala Ser Ile
                 20                  25                  30

Leu Cys Thr Leu Ile Gly Lys Gln His Leu Ala Gln Trp Ile Thr Ala
             35                  40                  45

Arg Cys Phe Tyr His Val Met Lys Leu Met Leu Gly Leu Asp Val Lys
         50                  55                  60

Val Val Gly Glu Glu Asn Leu Ala Lys Lys Pro Tyr Ile Met Ile Ala
 65                  70                  75                  80

Asn His Gln Ser Thr Leu Asp Ile Phe Met Leu Gly Arg Ile Phe Pro
                 85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
            115                 120                 125

Lys Arg Gln Glu Ala Ile Asp Thr Leu Asn Lys Gly Leu Glu Asn Val
130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
            180                 185                 190

Thr Ser Thr Leu Val Ser Pro Lys Tyr Gly Val Phe Asn Arg Gly Cys
            195                 200                 205

Met Ile Val Arg Ile Leu Lys Pro Ile Ser Thr Glu Asn Leu Thr Lys
210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
            275                 280                 285

Asp Val Asn Thr His Asn Glu Gly Ser Ser Val Lys Lys Met His
            290                 295                 300
```

<210> SEQ ID NO 4
<211> LENGTH: 245
<212> TYPE: PRT
<213> ORGANISM: E. coli

<400> SEQUENCE: 4

```
Met Leu Tyr Ile Phe Arg Leu Ile Ile Thr Val Ile Tyr Ser Ile Leu
  1               5                  10                  15

Val Cys Val Phe Gly Ser Ile Tyr Cys Leu Phe Ser Pro Arg Asn Pro
                 20                  25                  30

Lys His Val Ala Thr Phe Gly His Met Phe Gly Arg Leu Ala Pro Leu
             35                  40                  45
```

-continued

```
Phe Gly Leu Lys Val Glu Cys Arg Lys Pro Thr Asp Ala Glu Ser Tyr
             50                  55                  60

Gly Asn Ala Ile Tyr Ile Ala Asn His Gln Asn Asn Tyr Asp Met Val
 65                  70                  75                  80

Thr Ala Ser Asn Ile Val Gln Pro Pro Thr Val Thr Val Gly Lys Lys
                 85                  90                  95

Ser Leu Leu Trp Ile Pro Phe Phe Gly Gln Leu Tyr Trp Leu Thr Gly
                100                 105                 110

Asn Leu Leu Ile Asp Arg Asn Asn Arg Thr Lys Ala His Gly Thr Ile
            115                 120                 125

Ala Glu Val Val Asn His Phe Lys Lys Arg Ile Ser Ile Trp Met
        130                 135                 140

Phe Pro Glu Gly Thr Arg Ser Arg Gly Arg Gly Leu Leu Pro Phe Lys
145                 150                 155                 160

Thr Gly Ala Phe His Ala Ala Ile Ala Ala Gly Val Pro Ile Ile Pro
                165                 170                 175

Val Cys Val Ser Thr Thr Ser Asn Lys Ile Asn Leu Asn Arg Leu His
                180                 185                 190

Asn Gly Leu Val Ile Val Glu Met Leu Pro Pro Ile Asp Val Ser Gln
            195                 200                 205

Tyr Gly Lys Asp Gln Val Arg Glu Leu Ala Ala His Cys Arg Ser Ile
        210                 215                 220

Met Glu Gln Lys Ile Ala Glu Leu Asp Lys Glu Val Ala Glu Arg Glu
225                 230                 235                 240

Ala Ala Gly Lys Val
                245

<210> SEQ ID NO 5
<211> LENGTH: 374
<212> TYPE: PRT
<213> ORGANISM: Maize

<400> SEQUENCE: 5

Met Ala Ile Pro Leu Val Leu Val Leu Pro Leu Gly Leu Leu Phe
 1               5                  10                  15

Leu Leu Ser Gly Leu Ile Val Asn Ala Ile Gln Ala Val Leu Phe Val
                 20                  25                  30

Thr Ile Arg Pro Phe Ser Lys Ser Phe Tyr Arg Arg Ile Asn Arg Phe
             35                  40                  45

Leu Ala Glu Leu Leu Trp Leu Gln Leu Val Trp Val Asp Trp Trp
     50                  55                  60

Ala Gly Val Lys Val Gln Leu His Ala Asp Glu Thr Tyr Arg Ser
 65                  70                  75                  80

Met Gly Lys Glu His Ala Leu Ile Ile Ser Asn His Arg Ser Asp Ile
                 85                  90                  95

Asp Trp Leu Ile Gly Trp Ile Leu Ala Gln Arg Ser Gly Cys Leu Gly
            100                 105                 110

Ser Thr Leu Ala Val Met Lys Lys Ser Ser Lys Phe Leu Pro Val Ile
        115                 120                 125

Gly Trp Ser Met Trp Phe Ala Glu Tyr Leu Phe Leu Glu Arg Ser Trp
    130                 135                 140

Ala Lys Asp Glu Lys Thr Leu Lys Trp Gly Leu Gln Arg Leu Lys Asp
145                 150                 155                 160

Phe Pro Arg Pro Phe Trp Leu Ala Leu Phe Val Glu Gly Thr Arg Phe
```

```
                         165                 170                 175
Thr Pro Ala Lys Leu Ala Ala Gln Glu Tyr Ala Ala Ser Gln Gly
                180                 185                 190

Leu Pro Ala Pro Arg Asn Val Leu Ile Pro Arg Thr Lys Gly Phe Val
            195                 200                 205

Ser Ala Val Ser Ile Met Arg Asp Phe Val Pro Ala Ile Tyr Asp Thr
210                 215                 220

Thr Val Ile Val Pro Lys Asp Ser Pro Gln Pro Thr Met Leu Arg Ile
225                 230                 235                 240

Leu Lys Gly Gln Ser Ser Val Ile His Val Arg Met Lys Arg His Ala
                245                 250                 255

Met Ser Glu Met Pro Lys Ser Asp Glu Asp Val Ser Lys Trp Cys Lys
            260                 265                 270

Asp Ile Phe Val Ala Lys Asp Ala Leu Leu Asp Lys His Leu Ala Thr
        275                 280                 285

Gly Thr Phe Asp Glu Glu Ile Arg Pro Ile Gly Arg Pro Val Lys Ser
    290                 295                 300

Leu Leu Val Thr Leu Phe Trp Ser Cys Leu Leu Phe Gly Ala Ile
305                 310                 315                 320

Glu Phe Phe Lys Trp Thr Gln Leu Leu Ser Thr Trp Arg Gly Val Ala
                325                 330                 335

Phe Thr Ala Ala Gly Met Ala Leu Val Thr Gly Val Met His Val Phe
            340                 345                 350

Ile Met Phe Ser Gln Ala Glu Arg Ser Ser Ala Arg Ala Ala Arg
        355                 360                 365

Asn Arg Val Lys Lys Glu
    370

<210> SEQ ID NO 6
<211> LENGTH: 1383
<212> TYPE: DNA
<213> ORGANISM: Homo sapiens
<220> FEATURE:
<221> NAME/KEY: CDS
<222> LOCATION: (40)..(876)

<400> SEQUENCE: 6
ggagcgagct ggcggcgccg tcgggcgccg ggccgggcc atg gag ctg tgg ccg      54
                                            Met Glu Leu Trp Pro
                                              1               5 tgt ctg gcc gcg gcg ctg ctg ttg ctg ctg ctg gtg cag ctg agc       102
Cys Leu Ala Ala Ala Leu Leu Leu Leu Leu Leu Val Gln Leu Ser
              10                  15                  20 cgc gcg gcc gag ttc tac gcc aag gtc gcc ctg tac tgc gcg ctg tgc   150
Arg Ala Ala Glu Phe Tyr Ala Lys Val Ala Leu Tyr Cys Ala Leu Cys
              25                  30                  35 ttc acg gtg tcc gcc gtg gcc tcg ctc gtc tgc ctg ctg tgc cac ggc   198
Phe Thr Val Ser Ala Val Ala Ser Leu Val Cys Leu Leu Cys His Gly
          40                  45                  50 ggc cgg acg gtg gag aac atg agc atc atc ggc tgg ttc gtg cga agc   246
Gly Arg Thr Val Glu Asn Met Ser Ile Ile Gly Trp Phe Val Arg Ser
      55                  60                  65 ttc aag tac ttt tac ggg ctc cgc ttc gag gtg cgg gac ccg cgc agg   294
Phe Lys Tyr Phe Tyr Gly Leu Arg Phe Glu Val Arg Asp Pro Arg Arg
 70                  75                  80                  85 ctg cag gag gcc cgt ccc tgt gtc atc gtc tcc aac cac cag agc atc   342
Leu Gln Glu Ala Arg Pro Cys Val Ile Val Ser Asn His Gln Ser Ile
              90                  95                 100
```

```
ctg gac atg atg ggc ctc atg gag gtc ctt ccg gag cgc tgc gtg cag      390
Leu Asp Met Met Gly Leu Met Glu Val Leu Pro Glu Arg Cys Val Gln
        105                 110                 115 atc gcc aag cgg gag ctg ctc ttc ctg ggg ccc gtg ggc ctc atc atg      438
Ile Ala Lys Arg Glu Leu Leu Phe Leu Gly Pro Val Gly Leu Ile Met
            120                 125                 130 tac ctc ggg ggc gtc ttc ttc atc aac cgg cag cgc tct agc act gcc      486
Tyr Leu Gly Gly Val Phe Phe Ile Asn Arg Gln Arg Ser Ser Thr Ala
    135                 140                 145 atg aca gtg atg gcc gac ctg ggc gag cgc atg gtc agg gag aac ctc      534
Met Thr Val Met Ala Asp Leu Gly Glu Arg Met Val Arg Glu Asn Leu
150                 155                 160                 165 aaa gtg tgg atc tat ccc gag ggt act cgc aac gac aat ggg gac ctg      582
Lys Val Trp Ile Tyr Pro Glu Gly Thr Arg Asn Asp Asn Gly Asp Leu
                170                 175                 180 ctg cct ttt aag aag ggc gcc ttc tac ctg gca gtc cag gca cag gtg      630
Leu Pro Phe Lys Lys Gly Ala Phe Tyr Leu Ala Val Gln Ala Gln Val
            185                 190                 195 ccc atc gtc ccc gtg gtg tac tct tcc ttc tcc tcc ttc tac aac acc      678
Pro Ile Val Pro Val Val Tyr Ser Ser Phe Ser Ser Phe Tyr Asn Thr
    200                 205                 210 aag aag aag ttc ttc act tca gga aca gtc aca gtg cag gtg ctg gaa      726
Lys Lys Lys Phe Phe Thr Ser Gly Thr Val Thr Val Gln Val Leu Glu
215                 220                 225 gcc atc ccc acc agc ggc ctc act gcg gcg gac gtc cct gcg ctc gtg      774
Ala Ile Pro Thr Ser Gly Leu Thr Ala Ala Asp Val Pro Ala Leu Val
230                 235                 240                 245 gac acc tgc cac cgg gcc atg agg acc acc ttc ctc cac atc tcc aag      822
Asp Thr Cys His Arg Ala Met Arg Thr Thr Phe Leu His Ile Ser Lys
                250                 255                 260 acc ccc cag gag aac ggg gcc act gcg ggg tct ggc gtg cag ccg gcc      870
Thr Pro Gln Glu Asn Gly Ala Thr Ala Gly Ser Gly Val Gln Pro Ala
            265                 270                 275 cag tag cccagaccac ggcagggcat gacctgggga gggcaggtgg aagccgatgg       926
Gln ctggaggatg ggcagagggg actcctcccg gcttccaaat accactctgt ccggctcccc    986
cagctctcac tcagcccggg aagcaggaag ccccttctgt cactggtctc agacacaggc   1046
ccctggtgtc ccctgcaggg ggctcagctg gaccctcccc gggctcgagg gcagggactc   1106
gcgcccacgg cacctctggg ngctggggntg ataaagatga ggcttgcggc tgtgcccgc   1166 tggtgggctg agccacaagg ccccccgatgg cccaggagca gatgggagga ccccgaggcc   1226
aggagtccca gactcacgca ccctgggcca caggagccg ggaatcgggg cctgctgctc   1286
ctgctggcct gaagaatctg tggggtcagc actgtactcc gttgctgttt tttataaac   1346 acactcttgg aaaaaaaaaa aaaaaaaaa aaaaaaa                             1383

<210> SEQ ID NO 7
<211> LENGTH: 278
<212> TYPE: PRT
<213> ORGANISM: Homo sapiens

<400> SEQUENCE: 7

Met Glu Leu Trp Pro Cys Leu Ala Ala Ala Leu Leu Leu Leu Leu Leu
1               5                   10                  15

Leu Val Gln Leu Ser Arg Ala Ala Glu Phe Tyr Ala Lys Val Ala Leu
            20                  25                  30

Tyr Cys Ala Leu Cys Phe Thr Val Ser Ala Val Ala Ser Leu Val Cys
```

```
                35                   40                  45
Leu Leu Cys His Gly Gly Arg Thr Val Glu Asn Met Ser Ile Ile Gly
    50                  55                  60

Trp Phe Val Arg Ser Phe Lys Tyr Phe Tyr Gly Leu Arg Phe Glu Val
 65                  70                  75                  80

Arg Asp Pro Arg Leu Gln Glu Ala Arg Pro Cys Val Ile Val Ser
                 85                  90                  95

Asn His Gln Ser Ile Leu Asp Met Met Gly Leu Met Glu Val Leu Pro
                100                 105                 110

Glu Arg Cys Val Gln Ile Ala Lys Arg Glu Leu Leu Phe Leu Gly Pro
                115                 120                 125

Val Gly Leu Ile Met Tyr Leu Gly Gly Val Phe Phe Ile Asn Arg Gln
    130                 135                 140

Arg Ser Ser Thr Ala Met Thr Val Met Ala Asp Leu Gly Glu Arg Met
145                 150                 155                 160

Val Arg Glu Asn Leu Lys Val Trp Ile Tyr Pro Glu Gly Thr Arg Asn
                165                 170                 175

Asp Asn Gly Asp Leu Leu Pro Phe Lys Lys Gly Ala Phe Tyr Leu Ala
                180                 185                 190

Val Gln Ala Gln Val Pro Ile Val Pro Val Val Tyr Ser Ser Phe Ser
    195                 200                 205

Ser Phe Tyr Asn Thr Lys Lys Lys Phe Phe Thr Ser Gly Thr Val Thr
    210                 215                 220

Val Gln Val Leu Glu Ala Ile Pro Thr Ser Gly Leu Thr Ala Ala Asp
225                 230                 235                 240

Val Pro Ala Leu Val Asp Thr Cys His Arg Ala Met Arg Thr Thr Phe
                245                 250                 255

Leu His Ile Ser Lys Thr Pro Gln Glu Asn Gly Ala Thr Ala Gly Ser
                260                 265                 270

Gly Val Gln Pro Ala Gln
            275

<210> SEQ ID NO 8
<211> LENGTH: 248
<212> TYPE: PRT
<213> ORGANISM: H. influenzae

<400> SEQUENCE: 8

Met Leu Lys Leu Leu Arg Ile Phe Leu Val Leu Ile Cys Cys Ile Leu
 1               5                  10                  15

Ile Cys Val Leu Gly Thr Ile Tyr Ser Phe Ile Arg Phe Lys Asn Pro
                20                  25                  30

Ser Asn Val Gly Ile Val Ala Arg Trp Phe Gly Arg Leu Phe Thr Tyr
            35                  40                  45

Pro Leu Phe Gly Leu Lys Val Glu His Arg Ile Pro Gln Asp Gln Lys
    50                  55                  60

Gln Ile Ser Arg Ala Ile Tyr Ile Gly Asn His Gln Asn Asn Tyr Asp
 65                  70                  75                  80

Met Val Thr Ile Ser Tyr Met Val Gln Pro Arg Thr Val Ser Val Gly
                85                  90                  95

Lys Lys Ser Leu Ile Trp Ile Pro Phe Phe Thr Gly Ile Leu Tyr
                100                 105                 110

Trp Val Thr Gly Asn Ile Phe Leu Asp Arg Glu Asn Arg Thr Lys Ala
            115                 120                 125
```

```
His Asn Thr Met Ser Gln Leu Ala Arg Arg Ile Asn Glu Asp Asn Leu
        130                 135                 140

Ser Ile Trp Met Phe Pro Glu Gly Thr Arg Asn Arg Gly Arg Gly Leu
145                 150                 155                 160

Leu Pro Phe Lys Thr Gly Ala Phe Thr Phe His Ala Ala Ile Ser Ala
                165                 170                 175

Gly Val Pro Ile Ile Pro Val Val Cys Ser Ser Thr His Asn Lys Ile
                180                 185                 190

Asn Leu Asn Arg Trp Asp Asn Gly Lys Val Ile Cys Glu Ile Met Asp
                195                 200                 205

Pro Ile Asp Val Ser Gly Tyr Thr Lys Asp Asn Val Arg Asp Leu Ala
                210                 215                 220

Ala Tyr Cys His Phe Thr Asp Leu Met Glu Lys Arg Ile Ala Glu Leu
225                 230                 235                 240

Asp Glu Glu Ile Ala Lys Gly Asn
                245

<210> SEQ ID NO 9
<211> LENGTH: 253
<212> TYPE: PRT
<213> ORGANISM: S. typhimuriu

<400> SEQUENCE: 9

Met Leu Tyr Ile Phe Arg Leu Ile Val Thr Val Ile Tyr Ser Ile Leu
1                   5                   10                  15

Val Cys Val Phe Gly Ser Ile Tyr Cys Leu Phe Ser Pro Arg Asn Pro
                20                  25                  30

Lys His Val Ala Thr Phe Gly His Met Phe Gly Arg Leu Phe Thr Ala
                35                  40                  45

Pro Leu Phe Gly Leu Lys Val Glu Cys Arg Lys Pro Ala Asp Ala Glu
            50                  55                  60

Asn Tyr Gly Asn Ala Ile Tyr Ile Ala Asn His Gln Asn Asn Tyr Asp
65                  70                  75                  80

Met Val Thr Ala Ala Asn Ile Val Gln Pro Pro Thr Val Thr Val Gly
                85                  90                  95

Lys Lys Ser Leu Leu Trp Ile Pro Phe Phe Thr Gly Gln Leu Tyr
                100                 105                 110

Trp Leu Thr Gly Asn Leu Leu Ile Asp Arg Asn Asn Arg Ala Lys Ala
                115                 120                 125

His Ser Thr Ile Ala Ala Val Val Asn His Phe Lys Lys Arg Arg Ile
        130                 135                 140

Ser Ile Trp Met Phe Pro Glu Gly Thr Arg Ser Arg Gly Arg Gly Leu
145                 150                 155                 160

Leu Pro Phe Lys Thr Gly Ala Phe Thr Phe His Ala Ala Ile Ala Ala
                165                 170                 175

Gly Val Pro Ile Ile Pro Val Cys Val Ser Asn Thr Ser Asn Lys Val
                180                 185                 190

Asn Leu Asn Arg Leu Asn Asn Gly Leu Val Ile Val Glu Met Leu Pro
                195                 200                 205

Pro Val Asp Val Ser Glu Tyr Gly Lys Asp Gln Val Arg Glu Leu Ala
                210                 215                 220

Ala His Cys Arg Phe Thr Ala Leu Met Glu Gln Lys Ile Ala Glu Leu
225                 230                 235                 240

Asp Lys Glu Val Ala Glu Arg Glu Ala Thr Gly Lys Val
                245                 250
```

```
<210> SEQ ID NO 10
<211> LENGTH: 289
<212> TYPE: PRT
<213> ORGANISM: L. douglassi

<400> SEQUENCE: 10

Met Ala Lys Thr Arg Thr Ser Ser Leu Arg Asn Arg Arg Gln Leu Lys
 1               5                  10                  15

Pro Ala Val Ala Ala Thr Ala Asp Asp Asp Lys Asp Gly Val Phe Met
            20                  25                  30

Val Leu Leu Ser Cys Phe Lys Ile Phe Val Cys Phe Ala Phe Thr Val
        35                  40                  45

Val Leu Ile Thr Ala Val Ala Trp Gly Leu Ile Met Val Leu Leu Leu
    50                  55                  60

Pro Trp Pro Tyr Met Arg Ile Arg Leu Gly Asn Leu Tyr Gly His Ile
65                  70                  75                  80

Ile Gly Gly Leu Val Ile Trp Ile Tyr Gly Ile Pro Ile Lys Ile Gln
                85                  90                  95

Gly Ser Glu His Thr Lys Lys Arg Ala Ile Phe Thr Tyr Ile Ser Asn
            100                 105                 110

His Ala Ser Pro Ile Asp Ala Phe Phe Val Met Trp Leu Ala Pro Ile
        115                 120                 125

Gly Thr Val Gly Val Ala Lys Lys Glu Val Ile Trp Tyr Pro Leu Leu
    130                 135                 140

Gly Gln Leu Tyr Thr Leu Ala His His Ile Arg Ile Asp Arg Ser Asn
145                 150                 155                 160

Pro Ala Ala Ala Ile Gln Ser Phe Thr Met Lys Glu Ala Val Arg Val
                165                 170                 175

Ile Thr Glu Lys Asn Leu Ser Leu Ile Met Phe Pro Glu Gly Thr Arg
            180                 185                 190

Ser Gly Asp Gly Arg Leu Leu Pro Phe Lys Lys Gly Phe Val His Leu
        195                 200                 205

Ala Leu Gln Ser His Leu Pro Ile Val Pro Met Ile Leu Thr Gly Thr
    210                 215                 220

His Leu Ala Trp Phe Thr Arg Lys Gly Thr Phe Arg Val Arg Pro Val
225                 230                 235                 240

Pro Ile Thr Val Lys Tyr Leu Pro Pro Ile Asn Thr Asp Asp Trp Thr
                245                 250                 255

Val Asp Lys Ile Asp Asp Tyr Val Lys Met Ile His Asp Ile Tyr Val
            260                 265                 270

Arg Asn Leu Pro Ala Ser Gln Lys Pro Leu Gly Ser Thr Asn Arg Ser
        275                 280                 285

Lys

<210> SEQ ID NO 11
<211> LENGTH: 318
<212> TYPE: PRT
<213> ORGANISM: C. nucifera

<400> SEQUENCE: 11

Met Asp Ala Ser Gly Ala Ser Ser Phe Leu Arg Gly Arg Cys Leu Glu
 1               5                  10                  15

Ser Cys Phe Lys Ala Ser Phe Gly Met Ser Gln Pro Lys Asp Ala Ala
            20                  25                  30
```

-continued

```
Gly Gln Pro Ser Arg Arg Pro Ala Asp Ala Asp Phe Phe Thr Val
        35                  40                  45

Asp Asp Asp Arg Trp Ile Thr Val Ile Leu Ser Val Val Arg Ile Ala
 50                  55                  60

Ala Cys Phe Leu Ser Met Met Val Thr Thr Ile Val Trp Asn Met Ile
 65                  70                  75                  80

Met Leu Ile Leu Leu Pro Trp Pro Tyr Ala Arg Ile Arg Gln Gly Asn
                 85                  90                  95

Leu Tyr Gly His Val Thr Gly Arg Met Leu Phe Thr Met Trp Ile Leu
            100                 105                 110

Gly Asn Pro Ile Thr Ile Glu Gly Ser Glu Phe Ser Asn Thr Arg Ala
            115                 120                 125

Ile Tyr Ile Cys Asn His Ala Ser Leu Val Asp Ile Phe Leu Ile Met
            130                 135                 140

Trp Leu Ile Pro Lys Gly Thr Val Thr Ile Ala Lys Lys Glu Ile Ile
145                 150                 155                 160

Trp Tyr Pro Leu Phe Gly Gln Phe Thr Leu Tyr Val Leu Ala Asn His
                165                 170                 175

Gln Arg Ile Asp Arg Ser Asn Pro Ser Ala Ala Ile Glu Ser Ile Lys
                180                 185                 190

Glu Val Ala Arg Ala Val Val Lys Lys Asn Leu Ser Leu Ile Ile Phe
            195                 200                 205

Pro Glu Gly Thr Arg Ser Lys Thr Gly Arg Leu Leu Pro Phe Lys Lys
            210                 215                 220

Gly Phe Ile His Phe Thr Ile Ala Leu Gln Thr Arg Leu Pro Ile Val
225                 230                 235                 240

Pro Met Val Leu Thr Gly Thr His Leu Ala Trp Arg Lys Asn Ser Leu
                245                 250                 255

Arg Val Arg Pro Ala Pro Ile Thr Val Lys Tyr Phe Ser Pro Ile Lys
                260                 265                 270

Thr Asp Asp Trp Glu Glu Glu Lys Ile Asn His Tyr Val Glu Met Ile
            275                 280                 285

His Phe Thr Ala Leu Tyr Val Asp His Leu Pro Glu Ser Gln Lys Pro
            290                 295                 300

Leu Val Ser Lys Gly Arg Asp Ala Ser Gly Arg Ser Asn Ser
305                 310                 315
```

```
<210> SEQ ID NO 12
<211> LENGTH: 1660
<212> TYPE: DNA
<213> ORGANISM: Homo sapiens
<220> FEATURE:
<221> NAME/KEY: CDS
<222> LOCATION: (184)..(1311)

<400> SEQUENCE: 12
tctatgaaac caacatacat ggcgtttgca tcacagttgg agtcagatgt gagcccggag     60
ggcaggtgtc tggcttgtcc acccggaagc cctgagggca gctgttccca ctggctctgc    120
tgaccttgtg ccttggacgg ctgtcctcag cgagggccg tgcacccgct cctgagcagc    180 gcc atg ggc ctg ctg gcc ttc ctg aag acc cag ttc gtg ctg cac ctg    228
    Met Gly Leu Leu Ala Phe Leu Lys Thr Gln Phe Val Leu His Leu
     1               5                  10                  15 ctg gtc ggc ttt gtc ttc gtg gtg agt ggt ctg gtc atc aac ttc gtc    276
Leu Val Gly Phe Val Phe Val Val Ser Gly Leu Val Ile Asn Phe Val
                 20                  25                  30
```

-continued

```
cag ctg tgc acg ctg gcg ctc tgg ccg gtc agc aag cag ctc tac cgc      324
Gln Leu Cys Thr Leu Ala Leu Trp Pro Val Ser Lys Gln Leu Tyr Arg
         35                  40                  45 cgc ctc aac tgc cgc ctc gca tac tca ctc tgg agc caa ctg gtc atg      372
Arg Leu Asn Cys Arg Leu Ala Tyr Ser Leu Trp Ser Gln Leu Val Met
     50                  55                  60 ctg ctg gag tgg tgg tcc tgc acg gag tgt aca ctg ttc acg gac cag      420
Leu Leu Glu Trp Trp Ser Cys Thr Glu Cys Thr Leu Phe Thr Asp Gln
 65                  70                  75 gcc acg gta gag cgc ttt ggg aag gag cac gca gtc atc atc ctc aac      468
Ala Thr Val Glu Arg Phe Gly Lys Glu His Ala Val Ile Ile Leu Asn
 80                  85                  90                  95 cac aac ttc gag atc gac ttc ctc tgt ggg tgg acc atg tgt gag cgc      516
His Asn Phe Glu Ile Asp Phe Leu Cys Gly Trp Thr Met Cys Glu Arg
             100                 105                 110 ttc gga gtg ctg ggg agc tcc aag gtc ctc gct aag aag gag ctg ctc      564
Phe Gly Val Leu Gly Ser Ser Lys Val Leu Ala Lys Lys Glu Leu Leu
         115                 120                 125 tac gtg ccc ctc atc ggc tgg acg tgg tac ttt ctg gag att gtg ttc      612
Tyr Val Pro Leu Ile Gly Trp Thr Trp Tyr Phe Leu Glu Ile Val Phe
     130                 135                 140 tgc aag cgg aag tgg gag gag gac cgg gac acc gtg gtc gaa ggg ctg      660
Cys Lys Arg Lys Trp Glu Glu Asp Arg Asp Thr Val Val Glu Gly Leu
145                 150                 155 agg cgc ctg tcg gac tac ccc gag tac atg tgg ttt ctc ctg tac tgc      708
Arg Arg Leu Ser Asp Tyr Pro Glu Tyr Met Trp Phe Leu Leu Tyr Cys
160                 165                 170                 175 gag ggg acg cgc ttc acg gag acc aag cac cgc gtt agc atg gag gtg      756
Glu Gly Thr Arg Phe Thr Glu Thr Lys His Arg Val Ser Met Glu Val
             180                 185                 190 gcg gct gct aag ggg ctt cct gtc ctc aag tac cac ctg ctg ccg cgg      804
Ala Ala Ala Lys Gly Leu Pro Val Leu Lys Tyr His Leu Leu Pro Arg
         195                 200                 205 acc aag ggc ttc acc acc gca gtc aag tgc ctc cgg ggg aca gtc gca      852
Thr Lys Gly Phe Thr Thr Ala Val Lys Cys Leu Arg Gly Thr Val Ala
     210                 215                 220 gct gtc tat gat gta acc ctg aac ttc aga gga aac aag aac ccg tcc      900
Ala Val Tyr Asp Val Thr Leu Asn Phe Arg Gly Asn Lys Asn Pro Ser
225                 230                 235 ctg ctg ggg atc ctc tac ggg aag aag tac gag gcg gac atg tgc gtg      948
Leu Leu Gly Ile Leu Tyr Gly Lys Lys Tyr Glu Ala Asp Met Cys Val
240                 245                 250                 255 agg aga ttt cct ctg gaa gac atc ccg ctg gat gaa aag gaa gca gct      996
Arg Arg Phe Pro Leu Glu Asp Ile Pro Leu Asp Glu Lys Glu Ala Ala
             260                 265                 270 cag tgg ctt cat aaa ctg tac cag gag aag gac gcg ctc cag gag ata     1044
Gln Trp Leu His Lys Leu Tyr Gln Glu Lys Asp Ala Leu Gln Glu Ile
         275                 280                 285 tat aat cag aag ggc atg ttt cca ggg gag cag ttt aag cct gcc cgg     1092
Tyr Asn Gln Lys Gly Met Phe Pro Gly Glu Gln Phe Lys Pro Ala Arg
     290                 295                 300 agg ccg tgg acc ctc ctg aac ttc ctg tcc tgg gcc acc att ctc ctg     1140
Arg Pro Trp Thr Leu Leu Asn Phe Leu Ser Trp Ala Thr Ile Leu Leu
305                 310                 315 tct ccc ctc ttc agt ttt gtc ttg ggc gtc ttt gcc agc gga tca cct     1188
Ser Pro Leu Phe Ser Phe Val Leu Gly Val Phe Ala Ser Gly Ser Pro
320                 325                 330                 335 ctc ctg atc ctg act ttc ttg ggg ttt gtg gga gca gct tcc ttt gga     1236
Leu Leu Ile Leu Thr Phe Leu Gly Phe Val Gly Ala Ala Ser Phe Gly
             340                 345                 350
```

-continued

```
gtt cgc aga ctg ata gga gta act gag ata gaa aaa ggc tcc agc tac    1284
Val Arg Arg Leu Ile Gly Val Thr Glu Ile Glu Lys Gly Ser Ser Tyr
            355                 360                 365 gga aac caa gag ttt aag aaa aag gaa taattaatgg ctgtgactga           1331
Gly Asn Gln Glu Phe Lys Lys Lys Glu
        370                 375 acacacgcgg ccctgacggt ggtatccagt taactcaaaa ccaacacaca gagtgcagga   1391
aaagacaatt agaaactatt tttcttatta actggtgact aatattaaca aaacttgagc   1451
caagagtaaa gaattcagaa ggcctgtcag gtgaagtctt cagcctccca cagcgcaggg   1511
tcccagcatc tccacgcgcg cccgtgggag gtgggtccgg ccggagaggc ctcccgcgga   1571
cgccgtctct ccagaactcc gcttccaaga gggacctttg gctgctttct ctccttaaac   1631
ttagatcaaa ttttaaaaaa aaaaaaaaa                                    1660
```

<210> SEQ ID NO 13
<211> LENGTH: 376
<212> TYPE: PRT
<213> ORGANISM: Homo sapiens

<400> SEQUENCE: 13

```
Met Gly Leu Leu Ala Phe Leu Lys Thr Gln Phe Val Leu His Leu Leu
 1               5                  10                  15

Val Gly Phe Val Phe Val Val Ser Gly Leu Val Ile Asn Phe Val Gln
                20                  25                  30

Leu Cys Thr Leu Ala Leu Trp Pro Val Ser Lys Gln Leu Tyr Arg Arg
            35                  40                  45

Leu Asn Cys Arg Leu Ala Tyr Ser Leu Trp Ser Gln Leu Val Met Leu
        50                  55                  60

Leu Glu Trp Trp Ser Cys Thr Glu Cys Thr Leu Phe Thr Asp Gln Ala
 65                  70                  75                  80

Thr Val Glu Arg Phe Gly Lys Glu His Ala Val Ile Ile Leu Asn His
                85                  90                  95

Asn Phe Glu Ile Asp Phe Leu Cys Gly Trp Thr Met Cys Glu Arg Phe
            100                 105                 110

Gly Val Leu Gly Ser Ser Lys Val Leu Ala Lys Lys Glu Leu Leu Tyr
        115                 120                 125

Val Pro Leu Ile Gly Trp Thr Trp Tyr Phe Leu Glu Ile Val Phe Cys
    130                 135                 140

Lys Arg Lys Trp Glu Glu Asp Arg Asp Thr Val Val Glu Gly Leu Arg
145                 150                 155                 160

Arg Leu Ser Asp Tyr Pro Glu Tyr Met Trp Phe Leu Leu Tyr Cys Glu
                165                 170                 175

Gly Thr Arg Phe Thr Glu Thr Lys His Arg Val Ser Met Glu Val Ala
            180                 185                 190

Ala Ala Lys Gly Leu Pro Val Leu Lys Tyr His Leu Leu Pro Arg Thr
        195                 200                 205

Lys Gly Phe Thr Thr Ala Val Lys Cys Leu Arg Gly Thr Val Ala Ala
    210                 215                 220

Val Tyr Asp Val Thr Leu Asn Phe Arg Gly Asn Lys Asn Pro Ser Leu
225                 230                 235                 240

Leu Gly Ile Leu Tyr Gly Lys Lys Tyr Glu Ala Asp Met Cys Val Arg
                245                 250                 255

Arg Phe Pro Leu Glu Asp Ile Pro Leu Asp Glu Lys Glu Ala Ala Gln
            260                 265                 270
```

```
Trp Leu His Lys Leu Tyr Gln Glu Lys Asp Ala Leu Gln Glu Ile Tyr
            275                 280                 285

Asn Gln Lys Gly Met Phe Pro Gly Glu Gln Phe Lys Pro Ala Arg Arg
        290                 295                 300

Pro Trp Thr Leu Leu Asn Phe Leu Ser Trp Ala Thr Ile Leu Leu Ser
305                 310                 315                 320

Pro Leu Phe Ser Phe Val Leu Gly Val Phe Ala Ser Gly Ser Pro Leu
                325                 330                 335

Leu Ile Leu Thr Phe Leu Gly Phe Val Gly Ala Ala Ser Phe Gly Val
            340                 345                 350

Arg Arg Leu Ile Gly Val Thr Glu Ile Glu Lys Gly Ser Ser Tyr Gly
            355                 360                 365

Asn Gln Glu Phe Lys Lys Lys Glu
        370                 375

<210> SEQ ID NO 14
<211> LENGTH: 1523
<212> TYPE: DNA
<213> ORGANISM: Homo sapiens
<220> FEATURE:
<221> NAME/KEY: CDS
<222> LOCATION: (233)..(1174)

<400> SEQUENCE: 14
```

| | |
|---|---|
| cacgctggcg ctctggccgg tcagcaagca gctctaccgc cgcctcaact gccgcctcgc | 60 |
| ctactcactc tggagcctag cacaaaacta gaagcaaccc aagcacctgt cactggagac | 120 |
| taattatgcg gcacccatac agggaccctc tgcggccatc atggagagcc ttcatcttgc | 180 |
| ccgtacagtt ttaagcgaaa aggaagtat acaacaaagt ccataactgg tc atg ctg | 238 |

```
                                                         Met Leu
                                                           1 ctg gag tgg tgg tcc tgc acg gag tgt aca ctg ttc acg gac cag gcc       286
Leu Glu Trp Trp Ser Cys Thr Glu Cys Thr Leu Phe Thr Asp Gln Ala
        5                   10                  15 acg gta gag cgc ttt ggg aag gag cac gca gtc atc atc ctc aac cac       334
Thr Val Glu Arg Phe Gly Lys Glu His Ala Val Ile Ile Leu Asn His
    20                  25                  30 aac ttc gag atc gac ttc ctc tgt ggg tgg acc atg tgt gag cgc ttc       382
Asn Phe Glu Ile Asp Phe Leu Cys Gly Trp Thr Met Cys Glu Arg Phe
35                  40                  45                  50 gga gtg ctg ggg agc tcc aag gtc ctc gct aag aag gag ctg ctc tac       430
Gly Val Leu Gly Ser Ser Lys Val Leu Ala Lys Lys Glu Leu Leu Tyr
                55                  60                  65 gtg ccc ctc atc ggc tgg acg tgg tac ttt ctg gag att gtg ttc tgc       478
Val Pro Leu Ile Gly Trp Thr Trp Tyr Phe Leu Glu Ile Val Phe Cys
            70                  75                  80 aag cgg aag tgg gag gag gac cgg gac acc gtg gtc gaa ggg ctg agg       526
Lys Arg Lys Trp Glu Glu Asp Arg Asp Thr Val Val Glu Gly Leu Arg
        85                  90                  95 cgc ctg tcg gac tac ccc gag tac atg tgg ttt ctc ctg tac tgc gag       574
Arg Leu Ser Asp Tyr Pro Glu Tyr Met Trp Phe Leu Leu Tyr Cys Glu
    100                 105                 110 ggg acg cgc ttc acg gag acc aag cac cgc gtt agc atg gag gtg gcg       622
Gly Thr Arg Phe Thr Glu Thr Lys His Arg Val Ser Met Glu Val Ala
115                 120                 125                 130 gct gct aag ggg ctt cct gtc ctc aag tac cac ctg ctg ccg cgg acc       670
Ala Ala Lys Gly Leu Pro Val Leu Lys Tyr His Leu Leu Pro Arg Thr
                135                 140                 145
```

```
aag ggc ttc acc acc gca gtc aag tgc ctc cgg ggg aca gtc gca gct    718
Lys Gly Phe Thr Thr Ala Val Lys Cys Leu Arg Gly Thr Val Ala Ala
        150                 155                 160 gtc tat gat gta acc ctg aac ttc aga gga aac aag aac ccg tcc ctg    766
Val Tyr Asp Val Thr Leu Asn Phe Arg Gly Asn Lys Asn Pro Ser Leu
    165                 170                 175 ctg ggg atc ctc tac ggg aag aag tac gag gcg gac atg tgc gtg agg    814
Leu Gly Ile Leu Tyr Gly Lys Lys Tyr Glu Ala Asp Met Cys Val Arg
180                 185                 190 aga ttt cct ctg gaa gac atc ccg ctg gat gaa aag gaa gca gct cag    862
Arg Phe Pro Leu Glu Asp Ile Pro Leu Asp Glu Lys Glu Ala Ala Gln
195                 200                 205                 210 tgg ctt cat aaa ctg tac cag gag aag gac gcg ctc cag gag ata tat    910
Trp Leu His Lys Leu Tyr Gln Glu Lys Asp Ala Leu Gln Glu Ile Tyr
                215                 220                 225 aat cag aag ggc atg ttt cca ggg gag cag ttt aag cct gcc cgg agg    958
Asn Gln Lys Gly Met Phe Pro Gly Glu Gln Phe Lys Pro Ala Arg Arg
            230                 235                 240 ccg tgg acc ctc ctg aac ttc ctg tcc tgg gcc acc att ctc ctg tct    1006
Pro Trp Thr Leu Leu Asn Phe Leu Ser Trp Ala Thr Ile Leu Leu Ser
        245                 250                 255 ccc ctc ttc agt ttt gtc ttg ggc gtc ttt gcc agc gga tca cct ctc    1054
Pro Leu Phe Ser Phe Val Leu Gly Val Phe Ala Ser Gly Ser Pro Leu
    260                 265                 270 ctg atc ctg act ttc ttg ggg ttt gtg gga gca gct tcc ttt gga gtt    1102
Leu Ile Leu Thr Phe Leu Gly Phe Val Gly Ala Ala Ser Phe Gly Val
275                 280                 285                 290 cgc aga ctg ata gga gta act gag ata gaa aaa ggc tcc agc tac gga    1150
Arg Arg Leu Ile Gly Val Thr Glu Ile Glu Lys Gly Ser Ser Tyr Gly
                295                 300                 305 aac caa gag ttt aag aaa aag gaa taattaatgg ctgtgactga acacacgcgg   1204
Asn Gln Glu Phe Lys Lys Lys Glu
            310 ccctgacggt ggtatccagt taactcaaaa ccaacacaca gagtgcagga aaagacaatt   1264 agaaactatt tttcttatta actggtgact aatattaaca aaacttgagc caagagtaaa   1324 gaattcagaa ggcctgtcag gtgaagtctt cagcctccca cagcgcaggg tcccagcatc   1384 tccacgcgcg cccgtgggag gtgggtccgg ccggagaggc ctcccgcgga cgccgtctct   1444 ccagaactcc gcttccaaga gggacctttg gctgctttct ctccttaaac ttagatcaaa   1504 ttttaaaaaa aaaaaaaaa                                                1523

<210> SEQ ID NO 15
<211> LENGTH: 314
<212> TYPE: PRT
<213> ORGANISM: Homo sapiens

<400> SEQUENCE: 15

Met Leu Leu Glu Trp Trp Ser Cys Thr Glu Cys Thr Leu Phe Thr Asp
 1               5                  10                  15

Gln Ala Thr Val Glu Arg Phe Gly Lys Glu His Ala Val Ile Ile Leu
            20                  25                  30

Asn His Asn Phe Glu Ile Asp Phe Leu Cys Gly Trp Thr Met Cys Glu
        35                  40                  45

Arg Phe Gly Val Leu Gly Ser Ser Lys Val Leu Ala Lys Lys Glu Leu
    50                  55                  60

Leu Tyr Val Pro Leu Ile Gly Trp Thr Trp Tyr Phe Leu Glu Ile Val
65                  70                  75                  80
```

```
Phe Cys Lys Arg Lys Trp Glu Glu Asp Arg Asp Thr Val Val Glu Gly
                 85                  90                  95

Leu Arg Arg Leu Ser Asp Tyr Pro Glu Tyr Met Trp Phe Leu Leu Tyr
            100                 105                 110

Cys Glu Gly Thr Arg Phe Thr Glu Thr Lys His Arg Val Ser Met Glu
        115                 120                 125

Val Ala Ala Lys Gly Leu Pro Val Leu Lys Tyr His Leu Leu Pro
    130                 135                 140

Arg Thr Lys Gly Phe Thr Thr Ala Val Lys Cys Leu Arg Gly Thr Val
145                 150                 155                 160

Ala Ala Val Tyr Asp Val Thr Leu Asn Phe Arg Gly Asn Lys Asn Pro
                165                 170                 175

Ser Leu Leu Gly Ile Leu Tyr Gly Lys Lys Tyr Glu Ala Asp Met Cys
            180                 185                 190

Val Arg Arg Phe Pro Leu Glu Asp Ile Pro Leu Asp Glu Lys Glu Ala
        195                 200                 205

Ala Gln Trp Leu His Lys Leu Tyr Gln Glu Lys Asp Ala Leu Gln Glu
    210                 215                 220

Ile Tyr Asn Gln Lys Gly Met Phe Pro Gly Glu Gln Phe Lys Pro Ala
225                 230                 235                 240

Arg Arg Pro Trp Thr Leu Leu Asn Phe Leu Ser Trp Ala Thr Ile Leu
                245                 250                 255

Leu Ser Pro Leu Phe Ser Phe Val Leu Gly Val Phe Ala Ser Gly Ser
            260                 265                 270

Pro Leu Leu Ile Leu Thr Phe Leu Gly Phe Val Gly Ala Ala Ser Phe
        275                 280                 285

Gly Val Arg Arg Leu Ile Gly Val Thr Glu Ile Glu Lys Gly Ser Ser
    290                 295                 300

Tyr Gly Asn Gln Glu Phe Lys Lys Lys Glu
305                 310

<210> SEQ ID NO 16
<211> LENGTH: 1774
<212> TYPE: DNA
<213> ORGANISM: Homo sapiens
<220> FEATURE:
<221> NAME/KEY: CDS
<222> LOCATION: (158)..(1291)

<400> SEQUENCE: 16
tgaacccagc cggctccatc tcagcttctg gtttctaagt ccatgtgcca aaggctgcca      60
ggaaggagac gccttcctga gtcctggatc tttcttcctt ctggaaatct ttgactgtgg     120
gtagttattt atttctgaat aagagcgtcc acgcatc atg gac ctc gcg gga ctg     175
                                        Met Asp Leu Ala Gly Leu
                                          1               5 ctg aag tct cag ttc ctg tgc cac ctg gtc ttc tgc tac gtc ttt att      223
Leu Lys Ser Gln Phe Leu Cys His Leu Val Phe Cys Tyr Val Phe Ile
             10                  15                  20 gcc tca ggg cta atc atc aac acc att cag ctc ttc act ctc ctc ctc      271
Ala Ser Gly Leu Ile Ile Asn Thr Ile Gln Leu Phe Thr Leu Leu Leu
         25                  30                  35 tgg ccc att aac aag cag ctc ttc cgg aag atc aac tgc aga ctg tcc      319
Trp Pro Ile Asn Lys Gln Leu Phe Arg Lys Ile Asn Cys Arg Leu Ser
     40                  45                  50 tat tgc atc tca agc cag ctg gtg atg ctg ctg gag tgg tgg tcg ggc      367
Tyr Cys Ile Ser Ser Gln Leu Val Met Leu Leu Glu Trp Trp Ser Gly
 55                  60                  65                  70
```

```
acg gaa tgc acc atc ttc acg gac ccg cgc gcc tac ctc aag tat ggg      415
Thr Glu Cys Thr Ile Phe Thr Asp Pro Arg Ala Tyr Leu Lys Tyr Gly
             75                  80                  85 aag gaa aat gcc atc gtg gtt ctc aac cac aag ttt gaa att gac ttt      463
Lys Glu Asn Ala Ile Val Val Leu Asn His Lys Phe Glu Ile Asp Phe
         90                  95                 100 ctg tgt ggc tgg agc ctg tcc gaa cgc ttt ggg ctg tta ggg ggc tcc      511
Leu Cys Gly Trp Ser Leu Ser Glu Arg Phe Gly Leu Leu Gly Gly Ser
            105                 110                 115 aag gtc ctg gcc aag aaa gag ctg gcc tat gtc cca att atc ggc tgg      559
Lys Val Leu Ala Lys Lys Glu Leu Ala Tyr Val Pro Ile Ile Gly Trp
        120                 125                 130 atg tgg tac ttc acc gag atg gtc ttc tgt tcg cgc aag tgg gag cag      607
Met Trp Tyr Phe Thr Glu Met Val Phe Cys Ser Arg Lys Trp Glu Gln
135                 140                 145                 150 gat cgc aag acg gtt gcc acc agt ttg cag cac ctc cgg gac tac ccc      655
Asp Arg Lys Thr Val Ala Thr Ser Leu Gln His Leu Arg Asp Tyr Pro
            155                 160                 165 gag aag tat ttt ttc ctg att cac tgt gag ggc aca cgg ttc acg gag      703
Glu Lys Tyr Phe Phe Leu Ile His Cys Glu Gly Thr Arg Phe Thr Glu
        170                 175                 180 aag aag cat gag atc agc atg cag gtg gcc cgg gcc aag ggg ctg cct      751
Lys Lys His Glu Ile Ser Met Gln Val Ala Arg Ala Lys Gly Leu Pro
            185                 190                 195 cgc ctc aag cat cac ctg ttg cca cga acc aag ggc ttc gcc atc acc      799
Arg Leu Lys His His Leu Leu Pro Arg Thr Lys Gly Phe Ala Ile Thr
200                 205                 210 gtg agg agc ttg aga aat gta gtt tca gct gta tat gac tgt aca ctc      847
Val Arg Ser Leu Arg Asn Val Val Ser Ala Val Tyr Asp Cys Thr Leu
215                 220                 225                 230 aat ttc aga aat aat gaa aat cca aca ctg ctg gga gtc cta aac gga      895
Asn Phe Arg Asn Asn Glu Asn Pro Thr Leu Leu Gly Val Leu Asn Gly
            235                 240                 245 aag aaa tac cat gca gat ttg tat gtt agg agg atc cca ctg gaa gac      943
Lys Lys Tyr His Ala Asp Leu Tyr Val Arg Arg Ile Pro Leu Glu Asp
        250                 255                 260 atc cct gaa gac gat gac gag tgc tcg gcc tgg ctg cac aag ctc tac      991
Ile Pro Glu Asp Asp Asp Glu Cys Ser Ala Trp Leu His Lys Leu Tyr
            265                 270                 275 cag gag aag gat gcc ttt cag gag gag tac tac agg acg ggc acc ttc     1039
Gln Glu Lys Asp Ala Phe Gln Glu Glu Tyr Tyr Arg Thr Gly Thr Phe
        280                 285                 290 cca gag acg ccc atg gtg ccc ccc cgg cgg ccc tgg acc ctc gtg aac     1087
Pro Glu Thr Pro Met Val Pro Pro Arg Arg Pro Trp Thr Leu Val Asn
295                 300                 305                 310 tgg ctg ttt tgg gcc tcg ctg gtg ctc tac cct ttc ttc cag ttc ctg     1135
Trp Leu Phe Trp Ala Ser Leu Val Leu Tyr Pro Phe Phe Gln Phe Leu
            315                 320                 325 gtc agc atg atc agg agc ggg tct tcc ctg acg ctg gcc agc ttc atc     1183
Val Ser Met Ile Arg Ser Gly Ser Ser Leu Thr Leu Ala Ser Phe Ile
        330                 335                 340 ctc gtc ttc ttt gtg gcc tcc gtg gga gtt cga tgg atg att ggt gtg     1231
Leu Val Phe Phe Val Ala Ser Val Gly Val Arg Trp Met Ile Gly Val
            345                 350                 355 acg gaa att gac aag ggc tct gcc tac ggc aac tct gac agc aag cag     1279
Thr Glu Ile Asp Lys Gly Ser Ala Tyr Gly Asn Ser Asp Ser Lys Gln
        360                 365                 370 aaa ctg aat gac tgactcaggg aggtgtcacc atccgaaggg aaccttgggg         1331
Lys Leu Asn Asp
```

-continued

```
375
aactggtggc tctgcatat cctccttagt gggacacggt gacaaaggct gggtgagccc    1391
ctgctgggca cggcggaagt cacgacctct ccagccaggg agtctggtct caaggccgga    1451
tggggaggaa gatgttttgt aatctttttt tccccatgtg ctttagtggg ctttggtttt    1511 cttttgtgc gagtgtgtgt gagaatggct gtgtggtgag tgtgaacttt gttctgtgat     1571
catagaaagg gtattttagg ctgcagggga gggcagggct ggggaccgaa ggggacaagt    1631
tccccttcca tcctttggtg ctgagttttc tgtaacccct ggttgccaga gataaagtga    1691
aaagtgcttt aggtgagatg actaaattat gcctccaaga aaaaaaatt aaagtgcttt     1751 tctgggtcaa aaaaaaaaaa aaa                                            1774
```

<210> SEQ ID NO 17
<211> LENGTH: 378
<212> TYPE: PRT
<213> ORGANISM: Homo sapiens

<400> SEQUENCE: 17

```
Met Asp Leu Ala Gly Leu Leu Lys Ser Gln Phe Leu Cys His Leu Val
 1               5                  10                  15

Phe Cys Tyr Val Phe Ile Ala Ser Gly Leu Ile Ile Asn Thr Ile Gln
                20                  25                  30

Leu Phe Thr Leu Leu Leu Trp Pro Ile Asn Lys Gln Leu Phe Arg Lys
            35                  40                  45

Ile Asn Cys Arg Leu Ser Tyr Cys Ile Ser Ser Gln Leu Val Met Leu
        50                  55                  60

Leu Glu Trp Trp Ser Gly Thr Glu Cys Thr Ile Phe Thr Asp Pro Arg
 65                  70                  75                  80

Ala Tyr Leu Lys Tyr Gly Lys Glu Asn Ala Ile Val Val Leu Asn His
                85                  90                  95

Lys Phe Glu Ile Asp Phe Leu Cys Gly Trp Ser Leu Ser Glu Arg Phe
            100                 105                 110

Gly Leu Leu Gly Gly Ser Lys Val Leu Ala Lys Lys Glu Leu Ala Tyr
        115                 120                 125

Val Pro Ile Ile Gly Trp Met Trp Tyr Phe Thr Glu Met Val Phe Cys
    130                 135                 140

Ser Arg Lys Trp Glu Gln Asp Arg Lys Thr Val Ala Thr Ser Leu Gln
145                 150                 155                 160

His Leu Arg Asp Tyr Pro Glu Lys Tyr Phe Phe Leu Ile His Cys Glu
                165                 170                 175

Gly Thr Arg Phe Thr Glu Lys Lys His Glu Ile Ser Met Gln Val Ala
            180                 185                 190

Arg Ala Lys Gly Leu Pro Arg Leu Lys His His Leu Leu Pro Arg Thr
        195                 200                 205

Lys Gly Phe Ala Ile Thr Val Arg Ser Leu Arg Asn Val Val Ser Ala
    210                 215                 220

Val Tyr Asp Cys Thr Leu Asn Phe Arg Asn Asn Glu Asn Pro Thr Leu
225                 230                 235                 240

Leu Gly Val Leu Asn Gly Lys Lys Tyr His Ala Asp Leu Tyr Val Arg
                245                 250                 255

Arg Ile Pro Leu Glu Asp Ile Pro Glu Asp Asp Glu Cys Ser Ala
            260                 265                 270

Trp Leu His Lys Leu Tyr Gln Glu Lys Asp Ala Phe Gln Glu Glu Tyr
        275                 280                 285
```

```
Tyr Arg Thr Gly Thr Phe Pro Glu Thr Pro Met Val Pro Pro Arg Arg
    290                 295                 300
Pro Trp Thr Leu Val Asn Trp Leu Phe Trp Ala Ser Leu Val Leu Tyr
305                 310                 315                 320
Pro Phe Phe Gln Phe Leu Val Ser Met Ile Arg Ser Gly Ser Ser Leu
                325                 330                 335
Thr Leu Ala Ser Phe Ile Leu Val Phe Phe Val Ala Ser Val Gly Val
            340                 345                 350
Arg Trp Met Ile Gly Val Thr Glu Ile Asp Lys Gly Ser Ala Tyr Gly
        355                 360                 365
Asn Ser Asp Ser Lys Gln Lys Leu Asn Asp
    370                 375

<210> SEQ ID NO 18
<211> LENGTH: 52
<212> TYPE: PRT
<213> ORGANISM: Yeast

<400> SEQUENCE: 18

Pro Phe Lys Lys Gly Ala Phe His Leu Ala Gln Gln Gly Lys Ile Pro
1               5                   10                  15
Ile Val Pro Val Val Ser Asn Thr Ser Thr Leu Val Ser Pro Lys
            20                  25                  30
Tyr Gly Val Phe Asn Arg Gly Cys Met Ile Val Arg Ile Leu Lys Pro
        35                  40                  45
Ile Ser Thr Glu
    50

<210> SEQ ID NO 19
<211> LENGTH: 52
<212> TYPE: PRT
<213> ORGANISM: Homo sapiens

<400> SEQUENCE: 19

Pro Ser Asn Cys Gly Ala Phe His Leu Ala Val Gln Ala Gln Val Pro
1               5                   10                  15
Ile Val Pro Ile Val Met Ser Ser Tyr Gln Asp Phe Tyr Cys Lys Lys
            20                  25                  30
Glu Arg Arg Phe Thr Ser Gly Gln Cys Gln Val Arg Val Leu Pro Pro
        35                  40                  45
Val Pro Thr Glu
    50

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
tgcaagatgg aaggcgcc                                                    18

<210> SEQ ID NO 21
<211> LENGTH: 6
<212> TYPE: PRT
<213> ORGANISM: Homo sapiens

<400> SEQUENCE: 21
```

```
Gly Ala Phe His Leu Ala
 1               5
```

<210> SEQ ID NO 22
<211> LENGTH: 60
<212> TYPE: PRT
<213> ORGANISM: Yeast

<400> SEQUENCE: 22

```
Gln Gln Gly Lys Ile Pro Ile Val Pro Val Val Ser Asn Thr Ser
 1               5                  10                  15

Thr Leu Val Ser Pro Lys Tyr Gly Val Phe Asn Arg Gly Cys Met Ile
                20                  25                  30

Val Arg Ile Leu Lys Pro Ile Ser Thr Glu Asn Leu Thr Lys Asp Lys
            35                  40                  45

Ile Gly Glu Phe Ala Glu Lys Val Arg Asp Gln Met
        50                  55                  60
```

<210> SEQ ID NO 23
<211> LENGTH: 60
<212> TYPE: PRT
<213> ORGANISM: Homo sapiens

<400> SEQUENCE: 23

```
Val Arg Glu Asn Val Pro Ile Val Pro Val Val Tyr Ser Ser Phe Ser
 1               5                  10                  15

Ser Phe Tyr Asn Thr Lys Lys Lys Phe Phe Thr Ser Gly Thr Val Thr
                20                  25                  30

Val Gln Val Leu Glu Ala Ile Pro Thr Ser Gly Leu Thr Ala Ala Asp
            35                  40                  45

Val Pro Ala Leu Arg Gly Thr Pro Ala Thr Gly Pro
        50                  55                  60
```

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 24
cctcaaagtg tggatctatc                                          20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 25
ggaagagtac accacgggga c                                        21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 26

```
gactctagcc taggcttttg c                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 27
ctagcttata atacgactca c                                              21

<210> SEQ ID NO 28
<211> LENGTH: 23
<212> TYPE: PRT
<213> ORGANISM: Maize

<400> SEQUENCE: 28

Gly Leu Gln Arg Leu Lys Asp Phe Pro Arg Pro Phe Trp Leu Ala Leu
 1               5                  10                  15

Phe Val Glu Gly Thr Arg Phe
            20

<210> SEQ ID NO 29
<211> LENGTH: 23
<212> TYPE: PRT
<213> ORGANISM: Homo sapiens

<400> SEQUENCE: 29

Gly Leu Arg Arg Leu Ser Asp Tyr Pro Glu Tyr Met Trp Phe Leu Leu
 1               5                  10                  15

Tyr Cys Glu Gly Thr Arg Phe
            20

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 30
gactaccccg agtacatgtg gtttctc                                        27

<210> SEQ ID NO 31
<211> LENGTH: 9
<212> TYPE: PRT
<213> ORGANISM: Homo sapiens

<400> SEQUENCE: 31

Asp Tyr Pro Glu Tyr Met Trp Phe Leu
 1               5

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 32
cacatgtccg cctcgtactt cttc                                           24
```

<210> SEQ ID NO 33
<211> LENGTH: 46
<212> TYPE: PRT
<213> ORGANISM: Homo sapiens

<400> SEQUENCE: 33

Met Gly Leu Leu Ala Phe Leu Lys Thr Gln Phe Val Leu His Leu Leu
 1               5                  10                  15
Val Gly Phe Val Phe Val Val Ser Gly Leu Val Ile Asn Phe Val Gln
                20                  25                  30
Leu Cys Thr Leu Ala Leu Trp Pro Val Ser Lys Gln Leu Tyr
            35                  40                  45

<210> SEQ ID NO 34
<211> LENGTH: 46
<212> TYPE: PRT
<213> ORGANISM: Homo sapiens

<400> SEQUENCE: 34

Met Asp Leu Ala Gly Leu Leu Lys Ser Gln Phe Leu Cys His Leu Val
 1               5                  10                  15
Phe Cys Tyr Val Phe Ile Ala Ser Gly Leu Ile Ile Asn Thr Ile Gln
                20                  25                  30
Leu Phe Thr Leu Leu Leu Trp Pro Ile Asn Lys Gln Leu Phe
            35                  40                  45

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 35
ggctctagat attaatagta atcaattac                               29

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 36
cctcacgcat gcaccatggt aatagc                                  26

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 37
ggtgcatgcg tgaggctccg gtgc                                    24

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: primer

```
<400> SEQUENCE: 38
gtagttttca cggtacctga aatggaag                                              28

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 39
ggcccggtac catgggcctg ctggccttcc                                            30

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 40
taactcctcg agttattcct ttttcttaaa ctc                                        33

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 41
atggtggtac caccatggac ctcgcgggac tgctg                                      35

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 42
ggaggatatc tagaggccac cagttc                                                26
```